US010729820B2

(12) United States Patent
Jennings et al.

(10) Patent No.: US 10,729,820 B2
(45) Date of Patent: Aug. 4, 2020

(54) METHODS AND PROCESSES FOR APPLICATION OF DRUG DELIVERY POLYMERIC COATINGS

(71) Applicant: Ariste Medical, LLC, Memphis, TN (US)

(72) Inventors: Lisa K. Jennings, Memphis, TN (US); Jonathan D. McCanless, Memphis, TN (US); Xiaoping Chen, Germantown, TN (US); Michael Cole, Boulder, CO (US)

(73) Assignee: Ariste Medical, LLC, Memphis, TN (US)

( * ) Notice: Subject to any disclaimer, the term of this patent is extended or adjusted under 35 U.S.C. 154(b) by 0 days.

(21) Appl. No.: 14/941,446

(22) Filed: Nov. 13, 2015

(65) Prior Publication Data

US 2016/0101219 A1 Apr. 14, 2016

Related U.S. Application Data

(63) Continuation of application No. PCT/US2015/027135, filed on Apr. 22, 2015.
(Continued)

(51) Int. Cl.
*A61L 31/10* (2006.01)
*C09D 4/00* (2006.01)
(Continued)

(52) U.S. Cl.
CPC .............. *A61L 31/10* (2013.01); *A61L 31/08* (2013.01); *A61L 31/16* (2013.01); *C08F 222/10* (2013.01);
(Continued)

(58) Field of Classification Search
CPC .......... A61K 9/14; A61K 38/00; A61K 38/17; A61F 13/00; A61F 2/06; C08G 77/28;
(Continued)

(56) References Cited

U.S. PATENT DOCUMENTS 3,998,715 A 12/1976 Bohm et al.
4,016,306 A 4/1977 Miyagawa et al.
(Continued)

FOREIGN PATENT DOCUMENTS

CN 101198659 A 6/2008
CN 102472923 A 5/2012
(Continued)

OTHER PUBLICATIONS

Elbert, et al. Protein delivery from materials formed by self-selective conjugate addition reactions. J Control Release. Sep. 11, 2001;76(1-2):11-25.
(Continued)

*Primary Examiner* — Dah-Wei D. Yuan
*Assistant Examiner* — Andrew J Bowman
(74) *Attorney, Agent, or Firm* — Wilson Sonsini Goodrich & Rosati

(57) ABSTRACT

Polymeric coatings, their applications, and the methods of their preparation are described. The coatings may be used to confer desirable properties to the consumer and/or medical products. Also described are methods of loading therapeutic agents on the polymeric coatings and the applications of the drug eluting polymeric coatings thus obtained.

16 Claims, 15 Drawing Sheets

Related U.S. Application Data

(60) Provisional application No. 61/982,650, filed on Apr. 22, 2014.

(51) Int. Cl.
 *C08F 222/10* (2006.01)
 *A61L 31/08* (2006.01)
 *A61L 31/16* (2006.01)

(52) U.S. Cl.
 CPC .......... *C09D 4/00* (2013.01); *A61L 2300/204* (2013.01); *A61L 2300/406* (2013.01); *A61L 2300/606* (2013.01); *A61L 2420/02* (2013.01); *A61L 2420/06* (2013.01); *C08F 222/1025* (2020.02)

(58) Field of Classification Search
 CPC .......... C08G 18/75; G03G 9/097; B05C 3/09; A61L 31/10
 USPC .......... 424/487, 422, 486; 623/1.44; 528/28, 528/56, 85, 77, 81; 514/2; 522/75; 118/50; 427/2.1
 See application file for complete search history.

(56) References Cited

U.S. PATENT DOCUMENTS

| | | | |
|---|---|---|---|
| 4,368,300 A | 1/1983 | Nakano et al. | |
| 4,459,252 A | 7/1984 | MacGregor | |
| 4,713,244 A | 12/1987 | Bawa et al. | |
| 4,777,199 A | 10/1988 | Ishii et al. | |
| 4,869,198 A * | 9/1989 | Quillen | B05C 9/12 |
| | | | 118/50 |
| 4,886,062 A | 12/1989 | Wiktor | |
| 4,959,417 A | 9/1990 | Miyazono et al. | |
| 5,037,473 A | 8/1991 | Antonucci et al. | |
| 5,098,743 A | 3/1992 | Juday | |
| 5,176,692 A | 1/1993 | Wilk et al. | |
| 5,217,493 A | 6/1993 | Raad et al. | |
| 5,256,450 A | 10/1993 | Catena | |
| 5,290,217 A | 3/1994 | Campos | |
| 5,320,886 A | 6/1994 | Bowen | |
| 5,348,988 A | 9/1994 | Suh et al. | |
| 5,348,998 A | 9/1994 | Ito et al. | |
| 5,356,432 A | 10/1994 | Rutkow et al. | |
| 5,380,897 A | 1/1995 | Hoeschele et al. | |
| 5,409,915 A | 4/1995 | Farrell et al. | |
| 5,569,273 A | 10/1996 | Titone et al. | |
| 5,624,704 A | 4/1997 | Darouiche et al. | |
| 5,665,728 A | 9/1997 | Morris et al. | |
| 5,683,249 A | 11/1997 | Ibsen et al. | |
| 5,716,981 A | 2/1998 | Hunter et al. | |
| 5,767,170 A | 6/1998 | Ibsen et al. | |
| 5,788,979 A | 8/1998 | Alt et al. | |
| 5,824,049 A | 10/1998 | Ragheb et al. | |
| 5,824,082 A | 10/1998 | Brown | |
| 5,843,348 A | 12/1998 | Giordano | |
| 5,876,743 A | 3/1999 | Ibsen et al. | |
| 5,897,955 A | 4/1999 | Drumheller | |
| 5,902,283 A | 5/1999 | Darouiche et al. | |
| 6,154,064 A | 11/2000 | Proebsting et al. | |
| 6,156,064 A * | 12/2000 | Chouinard | A61F 2/07 |
| | | | 623/1.44 |
| 6,166,286 A | 12/2000 | Trabucco | |
| 6,273,913 B1 | 8/2001 | Wright et al. | |
| 6,306,166 B1 | 10/2001 | Barry et al. | |
| 6,326,417 B1 | 12/2001 | Jia | |
| 6,335,029 B1 | 1/2002 | Kamath et al. | |
| 6,391,983 B1 | 5/2002 | Bateman et al. | |
| 6,528,097 B1 | 3/2003 | Vaughn et al. | |
| 6,544,544 B2 | 4/2003 | Hunter et al. | |
| 6,551,710 B1 | 4/2003 | Chen et al. | |
| 6,558,686 B1 | 5/2003 | Darouiche | |
| 6,641,611 B2 | 11/2003 | Jayaraman | |
| 6,709,455 B1 | 3/2004 | Chouinard | |
| 6,726,923 B2 | 4/2004 | Iyer et al. | |
| 6,733,768 B2 | 5/2004 | Hossainy et al. | |
| 6,780,497 B1 | 8/2004 | Walter | |
| 6,800,082 B2 | 10/2004 | Rousseau | |
| 6,884,429 B2 | 4/2005 | Koziak et al. | |
| 6,890,546 B2 | 5/2005 | Mollison et al. | |
| 6,908,622 B2 | 6/2005 | Barry et al. | |
| 6,926,735 B2 | 8/2005 | Henderson | |
| 7,005,137 B1 | 2/2006 | Hossainy et al. | |
| 7,105,175 B2 | 9/2006 | Schwarz | |
| 7,166,570 B2 * | 1/2007 | Hunter | A61B 17/11 |
| | | | 514/21.92 |
| 7,176,261 B2 | 2/2007 | Tijsma et al. | |
| 7,223,286 B2 | 5/2007 | Wright et al. | |
| 7,247,313 B2 | 7/2007 | Roorda et al. | |
| 7,264,859 B2 | 9/2007 | Rouns et al. | |
| 7,297,159 B2 | 11/2007 | Hossainy et al. | |
| 7,300,662 B2 | 11/2007 | Falotico et al. | |
| 7,399,480 B2 | 7/2008 | Mollison et al. | |
| 7,442,721 B2 | 10/2008 | Cheng et al. | |
| 7,666,496 B2 | 2/2010 | Duran | |
| 8,008,364 B2 * | 8/2011 | Shimada | C09B 67/0033 |
| | | | 106/493 |
| 8,236,338 B2 * | 8/2012 | Abul-Khoudoud | A61L 27/16 |
| | | | 424/422 |
| 8,318,885 B2 * | 11/2012 | Matsukawa | C08G 18/44 |
| | | | 528/10 |
| 8,568,763 B2 | 10/2013 | Abul-Khoudoud et al. | |
| 9,125,970 B2 | 9/2015 | Abul-Khoudoud et al. | |
| 9,605,175 B2 | 3/2017 | Jennings et al. | |
| 10,314,912 B2 | 6/2019 | Jennings et al. | |
| 2002/0041899 A1 * | 4/2002 | Chudzik | A61L 27/34 |
| | | | 424/487 |
| 2003/0219533 A1 | 11/2003 | Chabrecek et al. | |
| 2003/0229392 A1 | 12/2003 | Wong | |
| 2003/0236342 A1 | 12/2003 | Walz et al. | |
| 2004/0039441 A1 | 2/2004 | Rowland et al. | |
| 2004/0148010 A1 | 7/2004 | Rush | |
| 2004/0193177 A1 | 9/2004 | Houghton et al. | |
| 2004/0197793 A1 | 10/2004 | Hassibi et al. | |
| 2004/0260318 A1 | 12/2004 | Hunter et al. | |
| 2005/0038455 A1 | 2/2005 | Bates et al. | |
| 2005/0058688 A1 | 3/2005 | Boerger et al. | |
| 2005/0177225 A1 | 8/2005 | Hunter et al. | |
| 2005/0220842 A1 | 10/2005 | DeWitt et al. | |
| 2005/0249776 A1 | 11/2005 | Chen et al. | |
| 2006/0039946 A1 | 2/2006 | Heruth et al. | |
| 2006/0052471 A1 | 3/2006 | Ashman et al. | |
| 2006/0052478 A1 | 3/2006 | Madsen et al. | |
| 2006/0067908 A1 | 3/2006 | Ding | |
| 2006/0121080 A1 | 6/2006 | Lye et al. | |
| 2006/0134218 A1 | 6/2006 | Abul-Khoudoud et al. | |
| 2006/0136051 A1 | 6/2006 | Furst et al. | |
| 2006/0153793 A1 | 7/2006 | Chrisstoffels et al. | |
| 2006/0182778 A1 | 8/2006 | Balar et al. | |
| 2006/0217797 A1 | 9/2006 | Wong | |
| 2006/0275338 A1 | 12/2006 | Flugelman | |
| 2007/0032864 A1 | 2/2007 | Furst et al. | |
| 2007/0134290 A1 | 6/2007 | Rowland et al. | |
| 2007/0244284 A1 | 10/2007 | Cheng et al. | |
| 2008/0008736 A1 | 1/2008 | Glauser | |
| 2008/0015322 A1 | 1/2008 | Kindt-Larsen et al. | |
| 2008/0132992 A1 | 6/2008 | Bates et al. | |
| 2008/0145516 A1 | 6/2008 | Herrmann et al. | |
| 2008/0167711 A1 | 7/2008 | Roorda | |
| 2008/0182921 A1 | 7/2008 | Suh et al. | |
| 2009/0130162 A2 | 5/2009 | Pathak et al. | |
| 2010/0247738 A1 | 9/2010 | Suh et al. | |
| 2010/0260922 A1 * | 10/2010 | Owens | A61F 2/07 |
| | | | 427/2.1 |
| 2011/0091515 A1 | 4/2011 | Zilberman et al. | |
| 2011/0238152 A1 | 9/2011 | Richter | |
| 2012/0115963 A1 | 5/2012 | Gruetzmacher et al. | |
| 2012/0157651 A1 * | 6/2012 | Chen | C08G 18/3876 |
| | | | 528/56 |
| 2013/0084543 A1 | 4/2013 | Liska et al. | |
| 2013/0189313 A1 | 7/2013 | Stewart et al. | |
| 2013/0261211 A1 | 10/2013 | Seeberger et al. | |

(56) References Cited

U.S. PATENT DOCUMENTS

| | | | |
|---|---|---|---|
| 2014/0112968 | A1 | 4/2014 | Abul-Khoudoud et al. |
| 2016/0206600 | A1 | 7/2016 | Abul-Khoudoud et al. |
| 2017/0246302 | A1 | 8/2017 | Jennings et al. |

FOREIGN PATENT DOCUMENTS

| | | |
|---|---|---|
| EP | 0652017 B1 | 9/1999 |
| EP | 1140242 B1 | 10/2002 |
| EP | 0652017 B2 | 1/2004 |
| GB | 1547801 A | 6/1979 |
| JP | S60120780 A | 6/1985 |
| JP | H05170705 A | 7/1993 |
| JP | H07101904 A | 4/1995 |
| JP | 2007101904 A | 4/2007 |
| WO | WO 91/12779 A1 | 9/1991 |
| WO | WO-0224247 A1 | 3/2002 |
| WO | WO-2004014447 A1 | 2/2004 |
| WO | WO-2005097227 A1 | 10/2005 |
| WO | WO-2005097787 A2 | 10/2005 |
| WO | WO-2005099787 A1 | 10/2005 |
| WO | WO-2006017275 A1 | 2/2006 |
| WO | WO-2007143997 A1 | 12/2007 |
| WO | WO-2008005439 A1 | 1/2008 |
| WO | WO-2009058079 A1 | 5/2009 |
| WO | WO 2012/012865 A1 | 2/2012 |
| WO | WO-2012024600 A1 | 2/2012 |
| WO | WO-2014/070792 A1 | 5/2014 |
| WO | WO-2015164524 A1 | 10/2015 |

OTHER PUBLICATIONS

Goyal, et al. A microfluidic platform for evaporation-based salt screening of pharmaceutical parent compounds. Lab Chip. May 7, 2013;13(9):1708-23. doi: 10.1039/c3lc41271g.
Hydroquinone and Hydroquinone Derivatives. Eastman Chemical Company. D-162E. Aug. 2009. 4 pages.
International search report and written report dated Jul. 10, 2015 for PCT/US2015/027135.
Li, et al. Polymer crystallization/melting induced thermal switching in a series of holographically patterned Bragg reflectors. Soft Matter. 2005; 1:238-242.
Lutolf, et al. Synthesis and physicochemical characterization of end-linked poly(ethylene glycol)-co-peptide hydrogels formed by Michael-type addition. Biomacromolecules. May-Jun. 2003;4(3):713-22.
Lutolf, et al. Systematic modulation of Michael-type reactivity of thiols through the use of charged amino acids. Bioconjug Chem. Nov.-Dec. 2001;12(6):1051-6.
Photoinitiator for UV curing. Ciba Specialty Chemicals. Oct. 2003. 8 pages.
Photoinitiators: classification. Aldrich. 2015. 15 pages.
International search report and written opinion dated Jul. 10, 2015 for PCT Application No. PCT/US15/27135.
Ferreira, et al. Photocrosslinkable polymers for biomedical applications. Biomedica engineering—Frontiers and Challenges. 2011; p. 55-74.
U.S. Appl. No. 15/457,310 Office Action dated May 8, 2018.
Acetylsalicylic acid. Product identification and general description. http://chemicalland21.com/lifescience/phar/ACETYLSALICYLIC%20ACID.htm. Mar. 19, 2009.
Allie, et al., Nitinol Stent Fractures in the SFA. Endovasc Today. 2004; 3:22-34.
Beyar. Novel approaches to reduce restenosis. Ann N Y Acad Sci. May 2004;1015:367-78.
Braun-Dullaeus, et al. Cell cycle protein expression in vascular smooth muscle cells in vitro and in vivo is regulated through phosphatidylinositol 3-kinase and mammalian target of rapamycin. Arterioscler Thromb Vasc Biol. Jul. 2001;21(7):1152-8.
Brewster, et al. Factors affecting patency of femoropopliteal bypass grafts. Surg Gynecol Obstet. Nov. 1983;157(5):437-42.

Cagiannos et al. Rapamycin-coated expanded polytetrafluorothylene bypass grafts exhibit decreased anastomotic neointimal hyperplasia in a porcine model. J of Vascular Surgery. Nov. 2005; 42(5):980-988.
Carter, et al. Long-term effects of polymer-based, slow-release, sirolimus-eluting stents in a porcine coronary model. Cardiovasc Res. Sep. 1, 2004;63(4):617-24.
Cayman Chemical, "Product Information: Ketoprofen", 1 page, Accessed on Oct. 25, 2016.
DAS. Optimal therapeutic approaches to femoropopliteal artery intervention. Catheter Cardiovasc Interv. Sep. 2004;63(1):21-30.
Diez-Juan, et al. Coordinate control of proliferation and migration by the p27Kip1/cyclin-dependent kinase/retinoblastoma pathway in vascular smooth muscle cells and fibroblasts. Circ Res. Mar. 7, 2003;92(4):402-10. Epub Jan. 30, 2003.
Dorrucci. Treatment of superficial femoral artery occlusive disease. J Cardiovasc Surg (Torino). Jun. 2004;45(3):193-201.
Duda, et al. Sirolimus-eluting stents for the treatment of obstructive superficial femoral artery disease: six-month results. Circulation. Sep. 17, 2002;106(12):1505-9.
Eagleton, et al. Femoral-infrapopliteal bypass with prosthetic grafts. Surgery. Oct. 1999;126(4):759-64; discussion 764-5.
Edwards et al. The effect of bacterial contamination on neointimal hyperplasia in vascular grafts. The American Surgeon. Dec. 2006; 72(12):1168-1175.
Ellozy, et al. Drug-eluting stents in peripheral vascular disease: eliminating restenosis. Mt Sinai J Med. Nov. 2003;70(6):417-9.
European search report and search report dated Apr. 6, 2016 for EP Application No. 13851649-7.
Fischer et al. Antibiotic Coated ePTFE Decreases Graft Colonization and Neointimal Hyperplasia. Journal of Surgical Research. 2009; 1-6.
Fischer, et al. Prosthetic vascular conduit in contaminated fields: a new technology to decrease ePTFE infections. Am Surg. Jun. 2008;74(6):524-8; discussion 528-9.
Fontaine, et al. Stent-induced intimal hyperplasia: are there fundamental differences between flexible and rigid stent designs? J Vasc Interv Radiol. Sep.-Oct. 1994;5(5):739-44.
Gallo, et al. Inhibition of intimal thickening after balloon angioplasty in porcine coronary arteries by targeting regulators of the cell cycle. Circulation. Apr. 27, 1999;99(16):2164-70.
Hill, et al. Drug-eluting stents: an early systematic review to inform policy. Eur Heart J. Jun. 2004;25(11):902-19.
Holman, et al. Management of wound and left ventricular assist device pocket infection. Ann Thorac Surg. Sep. 1999;68(3):1080-2.
Holmes, et al. Analysis of 1-year clinical outcomes in the SIRIUS trial: a randomized trial of a sirolimus-eluting stent versus a standard stent in patients at high risk for coronary restenosis. Circulation. Feb. 10, 2004;109(5):634-40.
Hwang, et al. Physiological transport forces govern drug distribution for stent-based delivery. Circulation. Jul. 31, 2001;104(5):600-5.
International search report and written opinion dated Dec. 20, 2013 for PCT Application No. US2013/067341.
International search report dated Nov. 3, 2005 for PCT Application No. US2005/24670.
Lee et al. Coating with paclitaxel improves graft survival in a porcine model of haemodialysis graft stenosis. Nephrol Dial Transplant. 2007; 22:2800-2804.
Lemson, et al. Intimal hyperplasia in vascular grafts. Eur J Vasc Endovasc Surg. Apr. 2000;19(4):336-50.
Loth, et al. Relative contribution of wall shear stress and injury in experimental intimal thickening at PTFE end-to-side arterial anastomoses. J Biomech Eng. Feb. 2002;124(1):44-51.
Masaki, et al. Inhibition of neointimal hyperplasia in vascular grafts by sustained perivascular delivery of paclitaxel. Kidney Int. Nov. 2004;66(5):2061-2069.
Matl, et al. New anti-infective coatings of medical implants. Antimicrob Agents Chemother. Jun. 2008;52(6):1957-63.
Mohanty, et al. Use of antibiotic-loaded polymethyl methacrylate beads in the management of musculoskeletal sepsis—a retrospective study. J Orthop Surg (Hong Kong). Jun. 2003;11(1):73-9.

(56) References Cited

OTHER PUBLICATIONS

Morice, et al. A randomized comparison of a sirolimus-eluting stent with a standard stent for coronary revascularization. N Engl J Med. Jun. 6, 2002;346(23):1773-80.
Moses, et al. Sirolimus-eluting stents versus standard stents in patients with stenosis in a native coronary artery. N Engl J Med. Oct. 2, 2003;349(14):1315-23.
Muradin, et al. Balloon dilation and stent implantation for treatment of femoropopliteal arterial disease: meta-analysis. Radiology. Oct. 2001;221(1):137-45.
Murray, et al. Hierarchy of variables correlated to odontoblast-like cell numbers following pulp capping.J Dent. Sep.-Nov. 2002;30(7-8):297-304.
Napoli, et al. Distribution of sirolimus in rat tissue. Clin Biochem. Mar. 1997;30(2):135-42.
Notice of allowance dated Apr. 26, 2012 for U.S. Appl. No. 11/180,195.
Notice of allowance dated May 8, 2015 for U.S. Appl. No. 14/031,835.
Notice of allowance dated Jun. 27, 2013 for U.S. Appl. No. 13/484,086.
Notice of allowance dated Nov. 14, 2016 for U.S. Appl. No. 14/439,650.
Office action dated Mar. 13, 2013 for U.S. Appl. No. 13/484,086.
Office action dated Mar. 18, 2010 for U.S. Appl. No. 11/180,195.
Office action dated Mar. 19, 2009 for U.S. Appl. No. 11/180,195.
Office action dated Jun. 16, 2016 for U.S. Appl. No. 14/439,650.
Office action dated Aug. 2, 2017 for U.S. Appl. No. 14/828,418.
Office action dated Aug. 9, 2017 for U.S. Appl. No. 15/457,310.
Office action dated Aug. 26, 2011 for U.S. Appl. No. 11/180,195.
Office action dated Sep. 16, 2008 for U.S. Appl. No. 11/180,195.
Office action dated Nov. 3, 2016 for U.S. Appl. No. 14/828,418.
Office action dated Nov. 10, 2010 for U.S. Appl. No. 11/180,195.
Regar, et al. Stent development and local drug delivery. Br Med Bull. 2001;59:227-48.
Ruef, et al. Endovascular interventions in iliac and infrainguinal occlusive artery disease. J Interv Cardiol. Dec. 2004;17(6):427-35.
Sayers, et al. Long-term results of femorotibial bypass with vein or polytetrafluoroethylene. Br J Surg. Jul. 1998;85(7):934-8.
Schwartz, et al. Preclinical evaluation of drug-eluting stents for peripheral applications: recommendations from an expert consensus group. Circulation. Oct. 19, 2004;110(16):2498-505.
Schwartz, et al. Preclinical restenosis models and drug-eluting stents: still important, still much to learn. J Am Coll Cardiol. Oct. 6, 2004;44(7):1373-85.
Shafiq, et al. A meta-analysis of clinical trials of paclitaxel- and sirolimus-eluting stents in patients with obstructive coronary artery disease. Br J Clin Pharmacol. Jan. 2005;59(1):94-101.
Sousa, et al. Sustained suppression of neointimal proliferation by sirolimus-eluting stents: one-year angiographic and intravascular ultrasound follow-up. Circulation. Oct. 23, 2001;104(17):2007-11.
Stone, et al. A polymer-based, paclitaxel-eluting stent in patients with coronary artery disease. N Engl J Med. Jan. 15, 2004;350(3):221-31.
Sun, et al. Role for p27(Kip1) in Vascular Smooth Muscle Cell Migration. Circulation. Jun. 19, 2001;103(24):2967-72.
Suzuki, et al. Stent-based delivery of sirolimus reduces neointimal formation in a porcine coronary model. Circulation. Sep. 4, 2001;104(10):1188-93.
Virmani, et al. Drug eluting stents: are human and animal studies comparable? Heart. Feb. 2003;89(2):133-8.
Weston, et al. Compliance and diameter mismatch affect the wall shear rate distribution near an end-to-end anastomosis. J Biomech. Feb. 1996;29(2):187-98.
Zohlnhofer, et al. Gene expression profiling of human stent-induced neointima by cDNA array analysis of microscopic specimens retrieved by helix cutter atherectomy: Detection of FK506-binding protein 12 upregulation. Circulation. Mar. 13, 2001;103(10):1396-402.
European search report and search opinion dated Oct. 11, 2017 for European Patent Application No. 15782551.4.
Kawaguchi; et al., "Synthesis and Physical Properties of Polyfunctional Methacrylates (Part 4). Synthesis and Physical Properties of Aromatic Dimethacrylate Copolymers", Dental Material Journal, 1984, 3, 272-279.
"Office action dated Sep. 19, 2018 for U.S. Appl. No. 15/457,310."
U.S. Appl. No. 14/828,418 Office Action dated Apr. 26, 2019.
U.S. Appl. No. 15/457,310 Notice of Allowance dated Jan. 24, 2019.
Co-pending U.S. Appl. No. 16/394,547, filed Apr. 25, 2019.

\* cited by examiner

FIG. 1
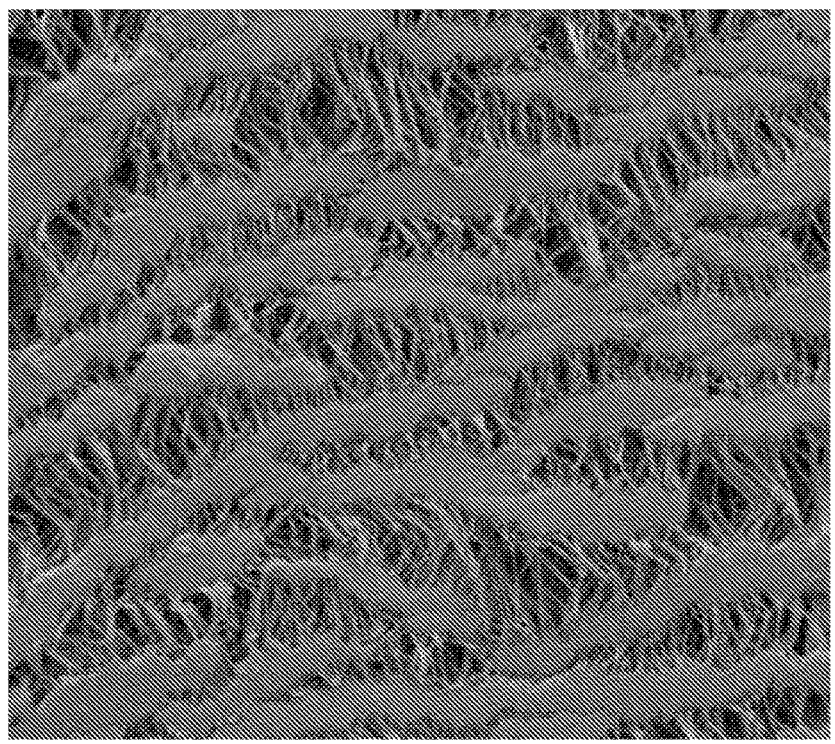
*FIG. 1A*
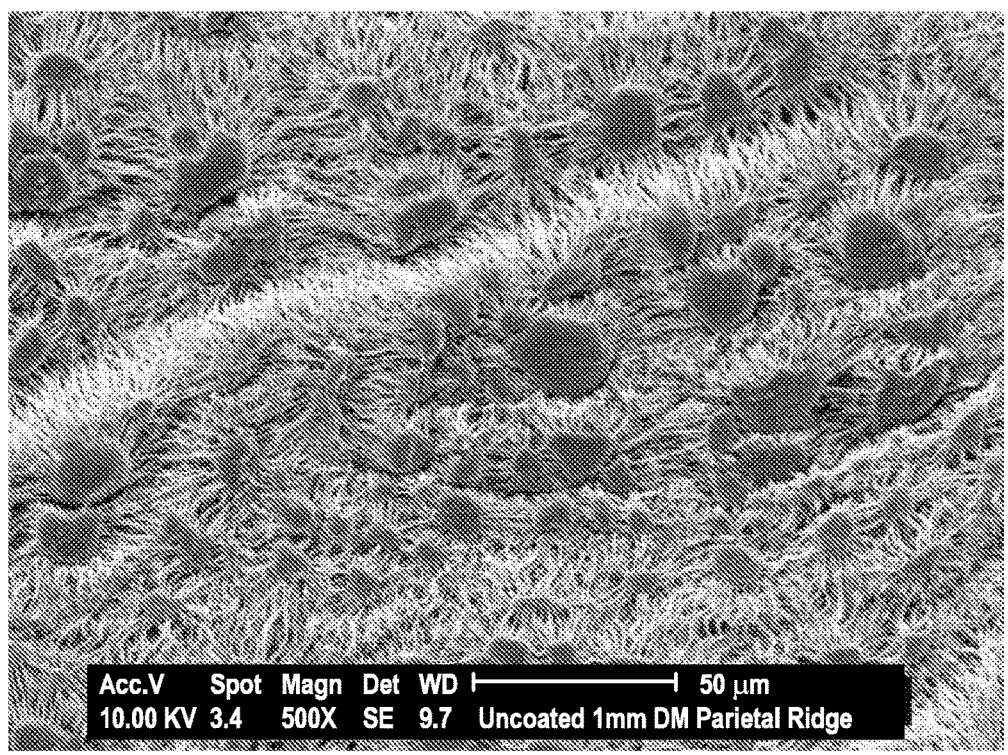
*FIG. 1B*

FIG. 2
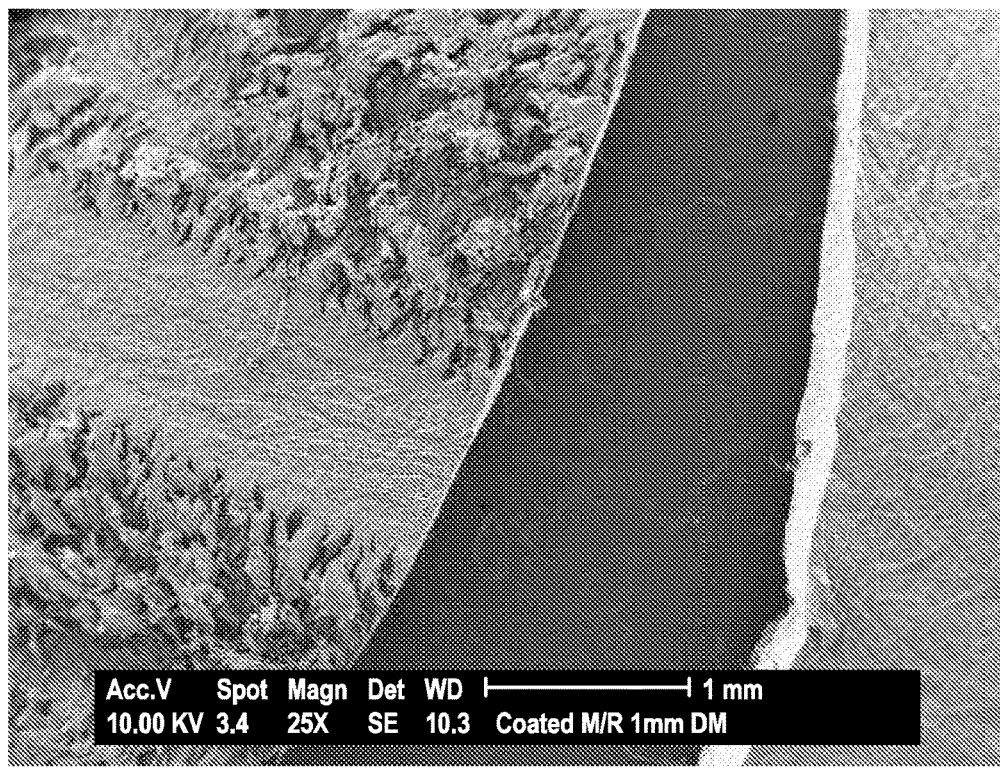
*FIG. 2A*
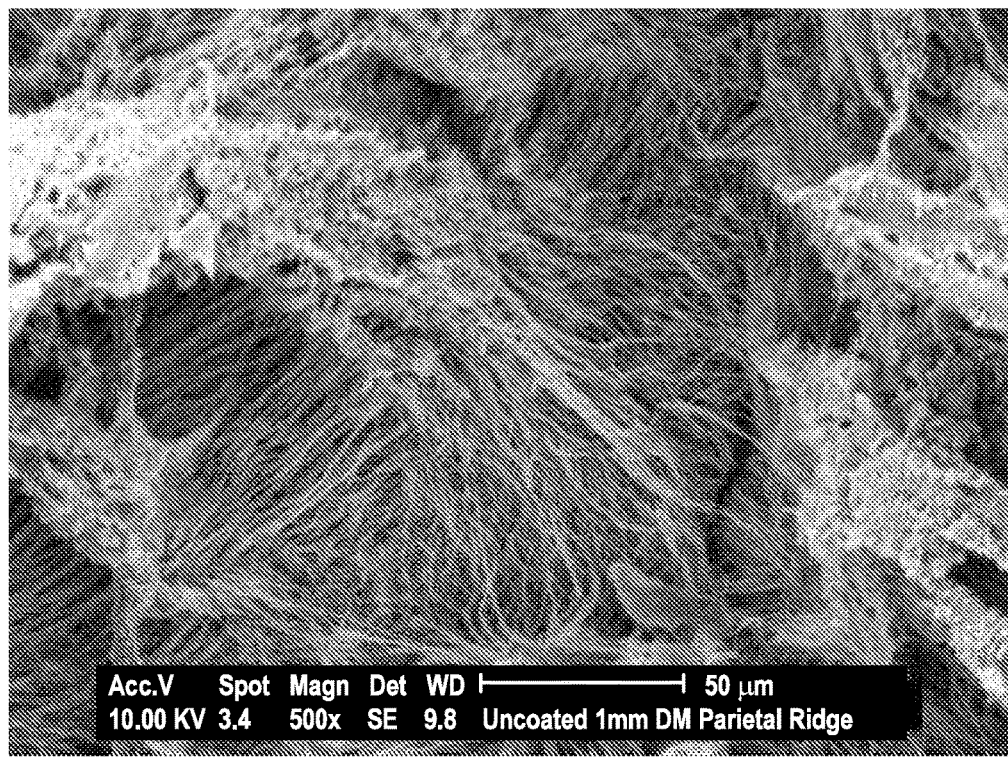
*FIG. 2B*

FIG. 3
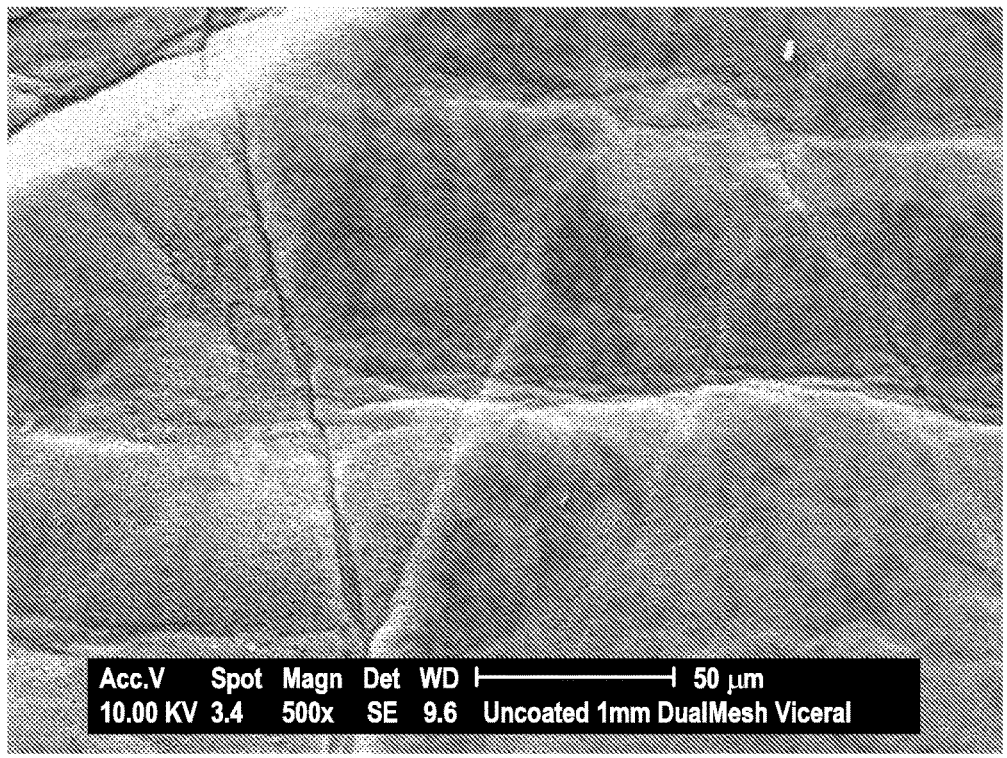
*FIG. 3A*
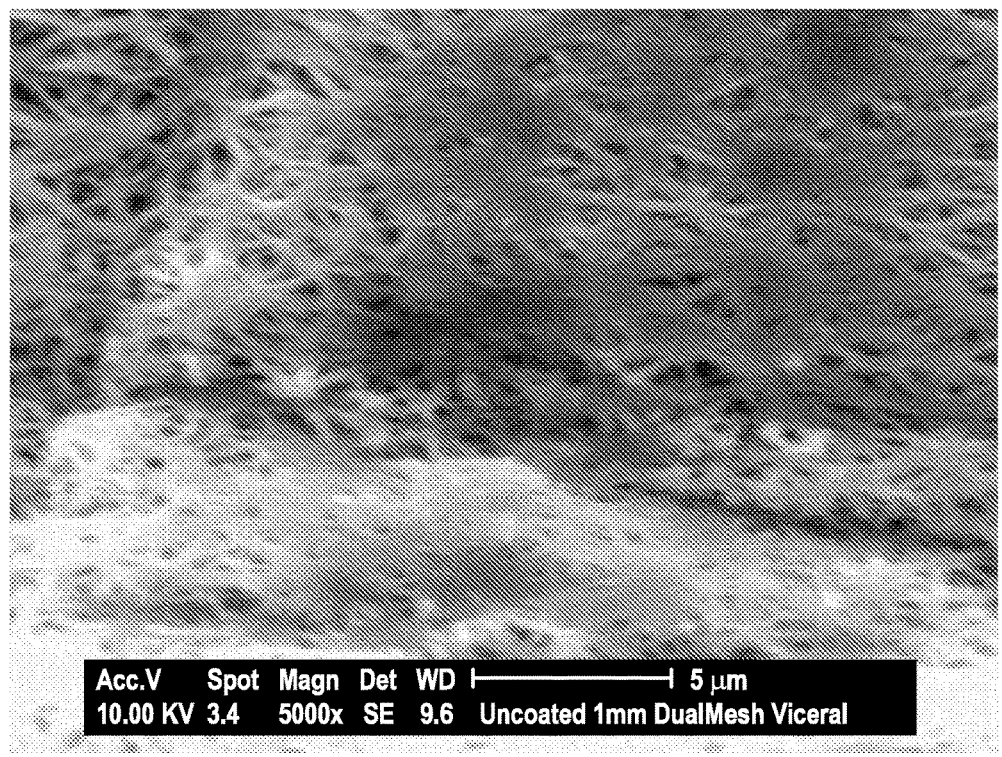
*FIG. 3B*

FIG. 5
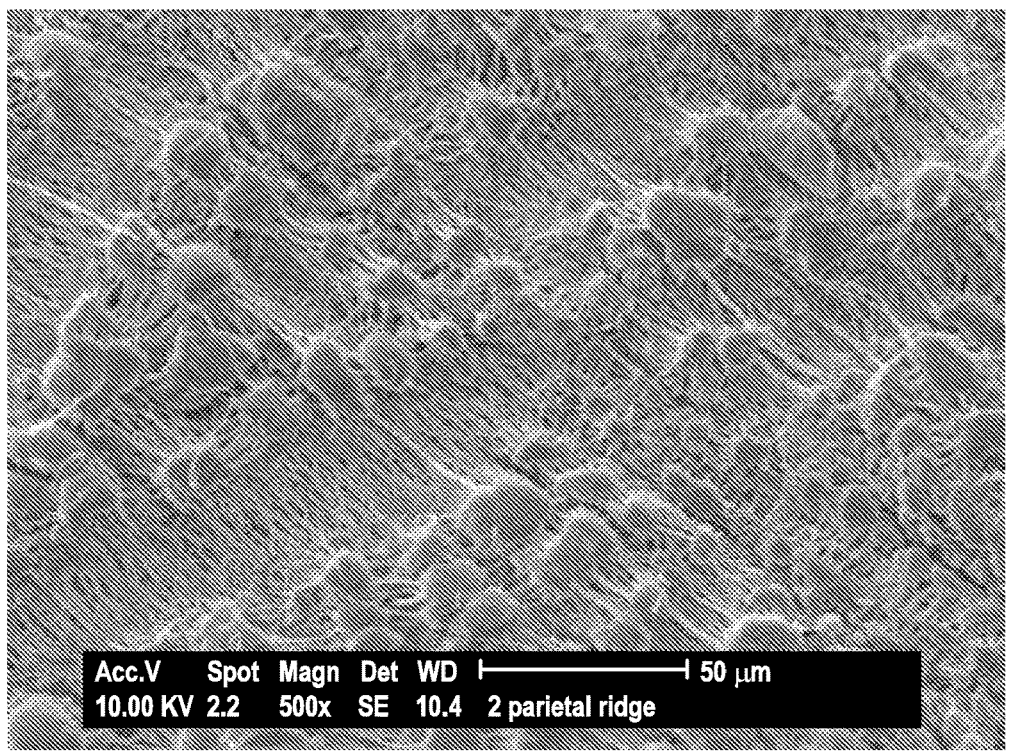
*FIG. 5A*
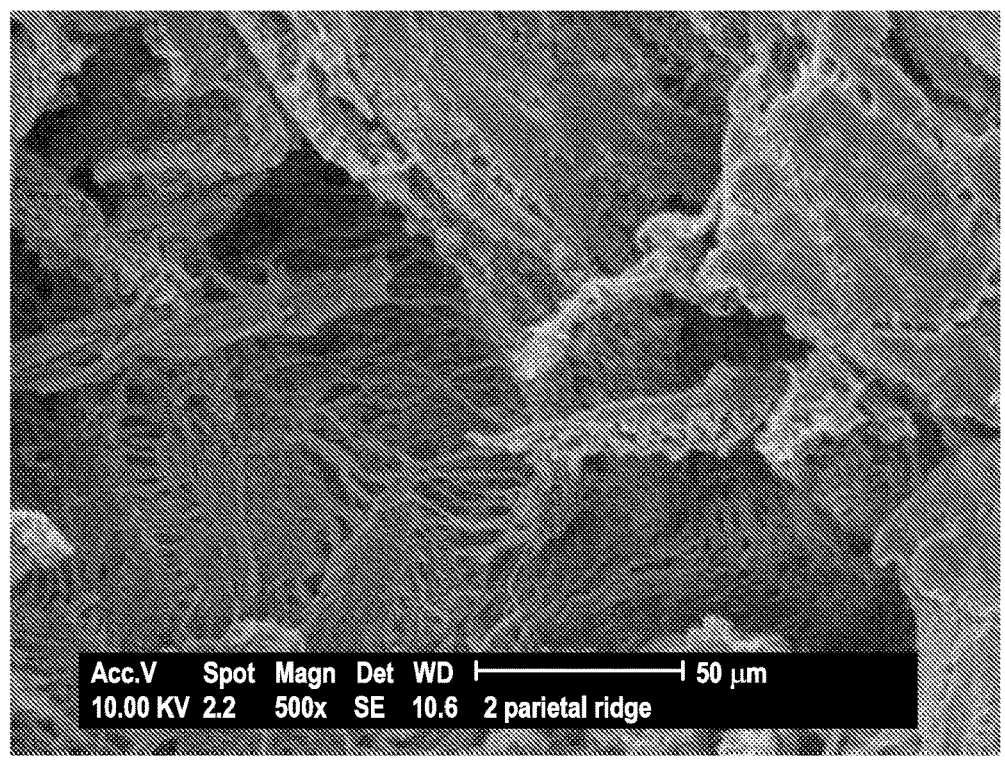
*FIG. 5B*

FIG. 6
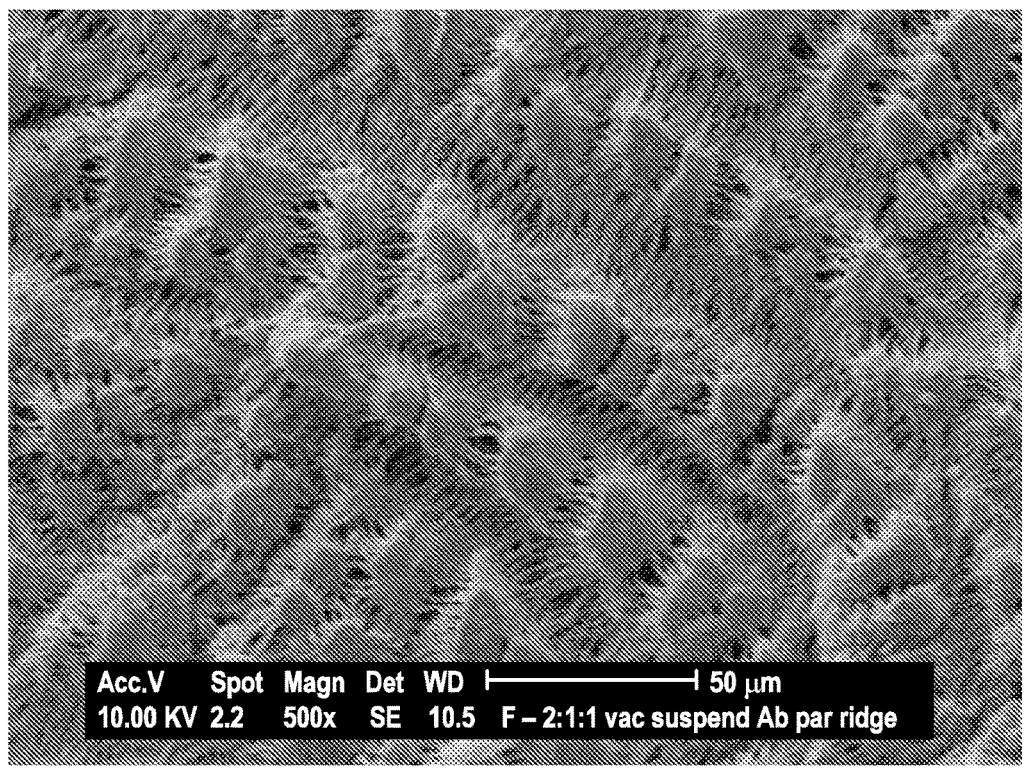
*FIG. 6A*
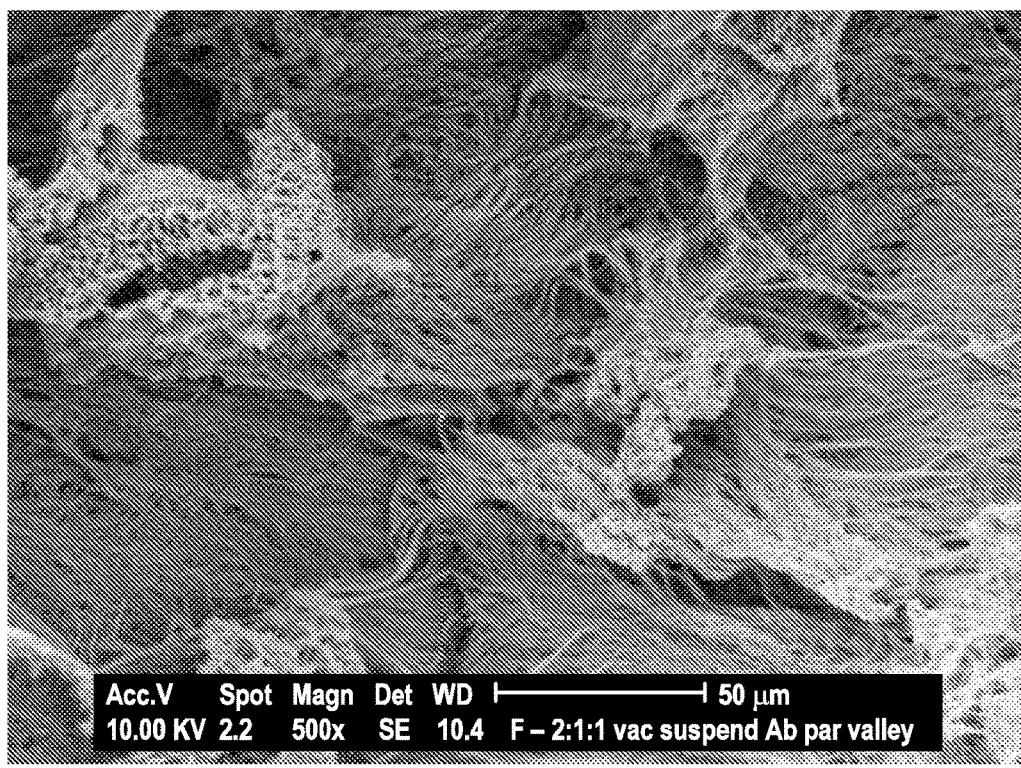
*FIG. 6B*

FIG. 7
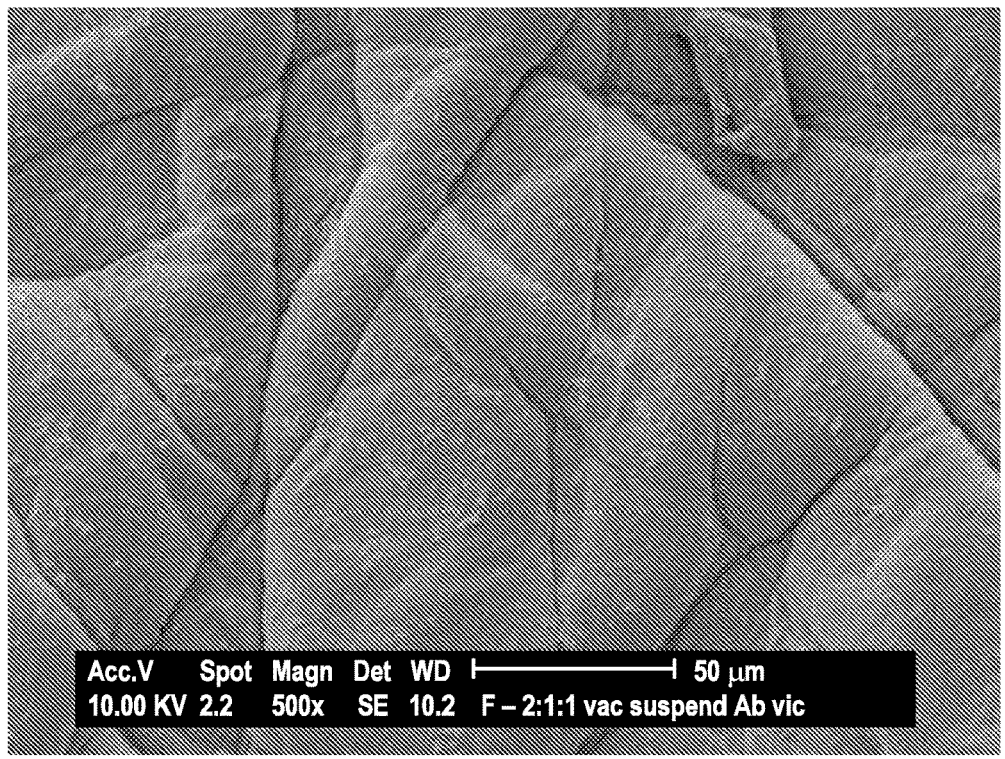
*FIG. 7A*
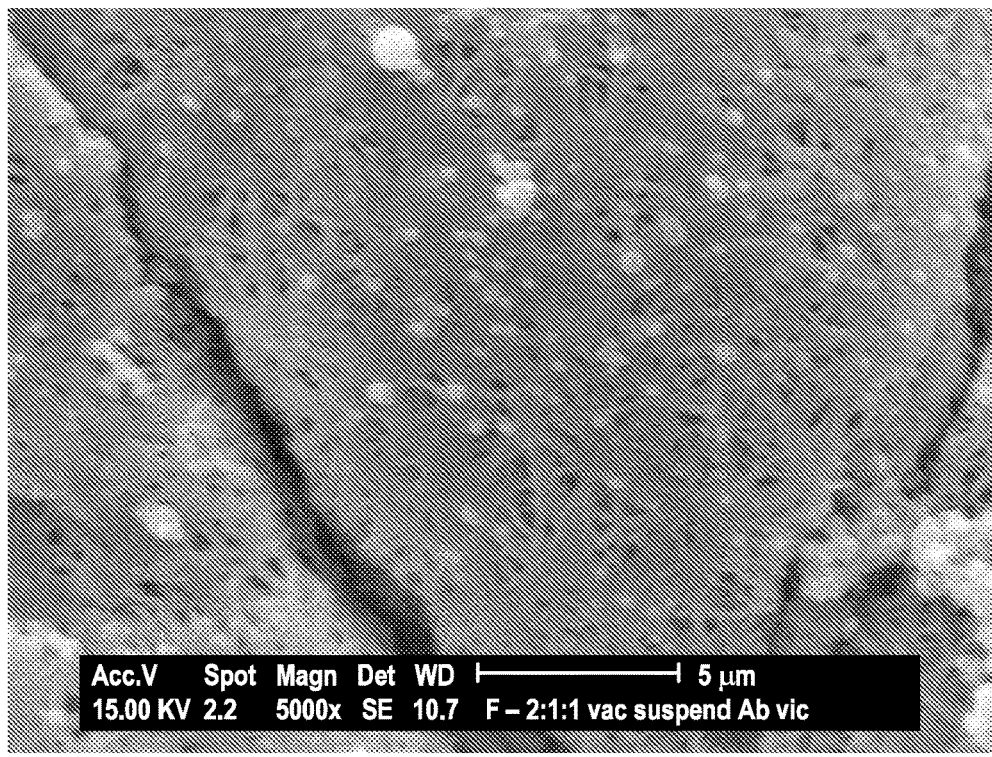
*FIG. 7B*

Print of window 38: Current Chromatogram(s)

Instrument 1 12/5/2013 1:59:57 PM MLAD

METHODS AND PROCESSES FOR APPLICATION OF DRUG DELIVERY POLYMERIC COATINGS

CROSS REFERENCE

This application is a continuation application of PCT Application No. PCT/US2015/027135, filed on Apr. 22, 2015, which claims the benefit of U.S. Provisional Application No. 61/982,650, filed on Apr. 22, 2014, which are incorporated herein by reference in their entirety for all purposes.

BACKGROUND OF THE INVENTION

Methacrylates coatings that may be used for ePTFE surfaces do not necessarily translate well to polypropylene. The underlying reason behind the inability of the methacrylate coatings to function properly as polypropylene coatings as compared to ePTFE coatings is due to the several orders of magnitude difference in surface area between the two substrate materials. ePTFE has an increased surface area over non-porous (non-expanded) material due to the nature of being porous and having multiple nanoscale fibrils interconnecting micron-scale nodes. Polypropylene has a very small surface area in comparison due to being made of consolidated smooth monofilaments which have thicknesses on the order of hundreds of microns to a millimeter. Because of this large reduction in surface area polypropylene coatings need be orders of magnitude thicker in order to accommodate drug quantities that will be clinically effective. In other words, if the surface area of polypropylene is 1,000 times less than ePTFE (from a bulk area perspective, such as a per square inch of mesh) then a coating holding the same amount of drug per polymeric coating mass will need be 1,000 times thicker to provide equal drug loadings in terms of drug density per bulk mesh area. The methacrylates coating formulations with a biphenyl center result in bulk polymers being brittle and having high bending stiffness. These mechanical properties are not an obstacle when coated on the ePTFE as coatings are of nanoscale, and the mechanics of nanoscale materials are not the same as that of their bulk material counterparts. When the thicker coatings are applied to polypropylene the brittleness of the materials cause the coatings to crack and break off of the monofilaments. Methacrylates also have processing and biocompatibility issues such as low degrees of polymerization, oxygen inhibition, slow kinetics, monomer toxicity, free-radical chemistry with very reactive heads capable of side reactions with drugs and solvents, susceptibility to Trommsdorff Effect, higher initiator to monomer ratios, and others. A polymeric coating that may be used effectively for both ePTFE and polypropylene surfaces is thus desired.

ePTFE is a general name given to any multitude of PTFE sheet or rod materials which have been mechanically deformed through tension, resulting in unique microstructures which translate into the unique material properties and applications of ePTFE materials. The physical attributes of these microstructures (node shape, node size, porosity, and internodal distance) result in varying degrees of the inherent low surface energy of PTFE. Unidirectional pulling of PTFE results in a microstructure characterized as narrow, broad (disc-like) nodes which continue into the depth of the microstructure and are interconnected by parallel running fibrils which run perpendicular to the planes of the nodes. Multidirectional (typically two perpendicular directions within the plane defined by the continuum of an ePTFE sheet) and radial pulling of PTFE materials result in spherical-like, isolated nodes which are interconnected by fibrils which run in all directions, reaching out from the curved surfaces of the node structures. FIG. 1 demonstrates typical microstructures formed from the two different pulling methods which result in comparable internodal distances with different node structures, spherical (multidirectional) and narrow, broad nodes (unidirectional). The spherical nodes have diameters similar to that of that of the thickness of the narrow, broad nodes.

While the customary coating application methods such as dipping, passive wicking, mechanical deformation assisted wicking, brushing, and spraying may generally be used for coating of unidirectional pulled ePTFE, these coatings methods when attempted on multidirectional pulled ePTFE similar to that shown in FIG. 1 may result in poor penetration of the casting solution into the microstructures and surface build-up and clogging of the pores. This lack of penetration and surface coating issue may often be detectable with the naked eye. In FIG. 1 it may be seen that the multidirectional pulled samples exhibit increased fibril density and hence are more challenging to penetrate within the depths of the low surface energy ePTFE (which is more prevalent in the multidirectional pulled ePTFE due the nature of the resulting microstructure). In short, the increased PTFE surface area in the multidirectional pulled ePTFE results in an increased resistance to penetration. In order to obtain similar fibril density that would coat with the traditional means further multidirectional pulling would be required and nodes would become smaller, fibrils thinner, and internodal distances would increase. Further pulling of this material would compromise its mechanical properties as a result of increased plastic deformation, limiting or excluding the use of the materials for the intended application. Thus it is desirable to have coating application methods that may be effectively used with a variety of ePTFE surfaces, including the multidirectionally pulled ePTFE samples.

Certain drugs, especially those containing amine groups, are often susceptible to degradation during free radical chain growth polymerization reactions, due to hydrogen abstraction between the amine and the living polymer's radical end. Polymerization is terminated and the drug molecule is degraded. Loading these drugs on polymeric coatings by polymerization of the coating in presence of drugs may result in significant loss of drug due to degradation. Further, the drug degradation products are often included within the resulting coating's polymer network. Thus, there is a need for improved methods of loading drugs onto the polymeric coatings.

SUMMARY OF THE INVENTION

In one aspect, the disclosure provides a method of coating a product surface. The method comprises exposing a product surface to a coating formulation and inducing polymerization of the coating formulation to obtain the coated product surface. The method may also further comprise physically assisting the coating formulation to enter the microstructure of the product surface by applying an external force prior to inducing polymerization of the coating formulation to obtain the coated product surface. The method may further comprise rinsing the coated product surface with a rinse solution. The rinse solution may comprise water, methanol, acetone, 0.01-0.2 M sodium hydroxide, or combinations thereof. The rinsing of the coated product surface may be performed multiple times. The rinse solution for each of the multiple rinses may independently comprise water, methanol, acetone, 0.01-0.2 M sodium hydroxide, or combinations thereof. The external force may be a positive or negative pressure. The positive or negative pressure may be applied as a pressure differential across the product surface and wherein the coating formulation may be applied to the high pressure side of the product surface. The external force may be applied in multiple of cycles.

The coating formulation may comprise a therapeutic agent. The therapeutic agent may be selected from the group consisting of antiplatelets, antithrombins, cytostatic agents, antiproliferative agents, vasodilators, alkylating agents, antimicrobials, antibiotics, antimicotics, disinfectants, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof. For example, the therapeutic agent may comprise antibiotics. In some examples, the therapeutic agent may be rifampicin, minocycline, minocycline hydrochloride, minocycline hyclate, or a mixture thereof.

The coating formulation may comprise an aromatic dimethacrylate. For example, the aromatic dimethacrylate may be

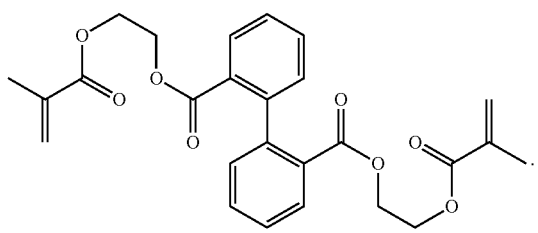 [SMILES: C=C(C)C(=O)OCCOC(=O)c1ccccc1-c1ccccc1C(=O)OCCOC(=O)C(=C)C]

The coating formulation may also comprise an aromatic dimethacrylate component or a salt thereof; and a monomethacrylate component or a salt thereof. The aromatic dimethacrylate may be biphenyldimethacrylate methyl-1-propanone, phenylbis(2,4,6-trimethylbenzoyl) phosphine oxide, diphenyl(2,4,6 trimethylbenzoyl)phosphine oxide, or camphorquinone.

The coating formulation may comprise a thiol monomer and an unsaturated monomer, which may or may not be the same as that containing in the thiol group. With such coating, The method may further comprise subjecting the product surface to high-energy vis/UV radiation, plasma treatment, and/or chemical treatment prior to exposing the product surface to the coating formulation. The thiol monomer may be a polythiol, for example pentaerythritol tetrakis(3-mercaptopropionate). The unsaturated monomer may be a compound comprising one or more carbon-carbon double and/or triple bonds. The product surface my comprise polypropylene or PTFE.

In another aspect, the disclosure provides a method of obtaining a drug eluting coated product surface. The method comprises (a) exposing a product surface to a coating formulation, (b) conducting a polymerization reaction to obtain a coated product surface and (c) drying the coated product surface to obtain the drug eluting coated product surface. The method may further comprise exposing the coated product surface to a solution of a therapeutic agent in a solvent (for example in methanol) after step b and/or step c. The exposing of the coated product surface to the solution of the therapeutic agent may be performed at a reduced temperature. In some examples, the step c may be performed at a reduced temperature. The reduced temperature may be about −20° C. For example −50° C., −40° C., −30° C., 20° C., −10° C., 0° C., 10° C., 20° C., 30° C., 40° C. or 50° C. One or more of the method may be performed under an inert atmosphere. The inert atmosphere may comprise nitrogen and/or argon.

(BPDM)

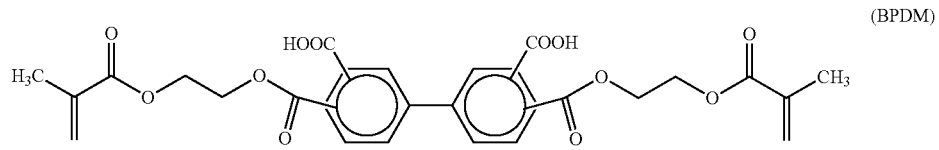

and the monomethacrylate component may be N-tolylglycine-glycidylmethacrylate (NTG-GMA) or salt thereof. The product surface may comprise an ePTFE surface. In some examples, a side of the ePTFE surface may comprise an alternating ridge/valley texture. The ePTFE surface may further comprise backing. The ePTFE surface opposite to the backing may comprise an alternating ridge/valley texture. The backing may comprise silicone, PTFE, or ePTFE. The ePTFE backing may comprise unidirectionally or multidirectionally pulled ePTFE. The product surface may comprise of a multidirectional or an unidirectional pulled ePTFE. The coating may be performed under an inert atmosphere. The inert atmosphere may comprise nitrogen and/or argon.

The coating formulation may comprise a dimethacrylate. The dimethacrylate may be polyethylene glycol dimethacrylate. In such embodiments, the product surface may comprise polypropylene. The coating may be performed under an inert atmosphere. The inert atmosphere may comprise nitrogen and/or argon.

The coating formulation may further comprise one or more polymerization initiators. The one or more polymerization initiators may be thermal, chemical, photo-, ionic initiators or a mixture thereof. The polymerization initiator may be 2-hydroxy-1-[4-(2-hydroxyethoxy)phenyl]-2-

The method may further comprise cleaning of the coated product surface. Cleaning of the coated product surface may be performed before and/or after the exposure the coated product surface to the solution of the therapeutic agent. Cleaning may comprise rinsing the coated product surface with a rinse solution. The rinse solution may comprise water, methanol, acetone, 0.01-0.2 M sodium hydroxide, or combinations thereof. Rinsing of the coated product surface may be performed multiple times. The rinse solution for each of the multiple rinses may independently comprise water, methanol, acetone, 0.01-0.2 M sodium hydroxide, or combinations thereof.

The coating formulation may comprise an aromatic dimethacrylate. For example, the aromatic dimethacrylate may be

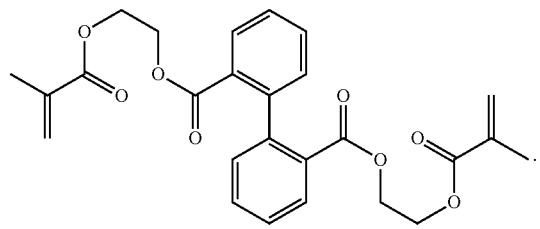 [SMILES: C=C(C)C(=O)OCCOC(=O)c1ccccc1-c1ccccc1C(=O)OCCOC(=O)C(=C)C]

The coating formulation may also comprise an aromatic dimethacrylate component or a salt thereof; and a monomethacrylate component or a salt thereof. The aromatic dimethacrylate may be biphenyldimethacrylate

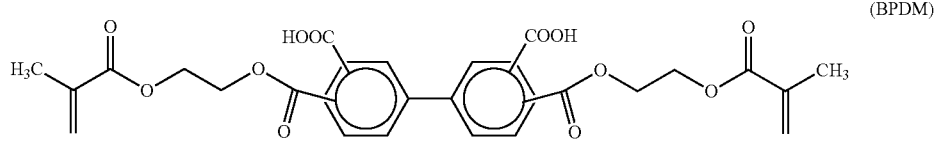
(BPDM)

and the monomethacrylate component may be N-tolylglycine-glycidylmethacrylate (NTG-GMA) or salt thereof. The product surface may comprise an ePTFE surface. In some examples, a side of the ePTFE surface may comprise an alternating ridge/valley texture. The ePTFE surface may further comprise backing. The ePTFE surface opposite to the backing may comprise an alternating ridge/valley texture. The backing may comprise silicone, PTFE, or ePTFE. The ePTFE backing may comprise unidirectionally or multidirectionally pulled ePTFE. The product surface may comprise of a multidirectional or an unidirectional pulled ePTFE. The coating may be performed under an inert atmosphere. The inert atmosphere may comprise nitrogen and/or argon.

In some examples, the aromatic dimethacrylate component may be a compound of Formula II

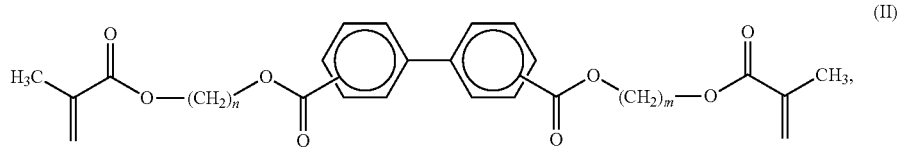
(II)

wherein each n may be independently 1-10, each m may be independently 1-10.

In some examples, the aromatic dimethacrylate component may be a compound of Formula III

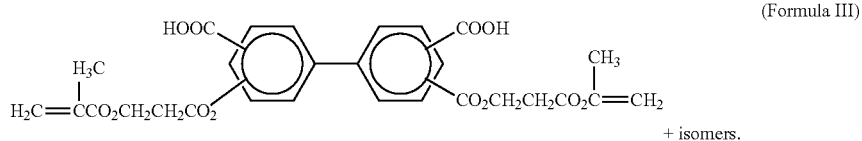
(Formula III)

+ isomers.

In some examples, the aromatic dimethacrylate may be biphenyldimethacrylate.

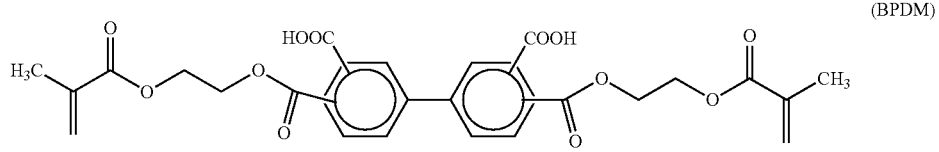
(BPDM)

and the monomethacrylate component may be N-tolylglycine-glycidylmethacrylate (NTG-GMA) or salt thereof.

The biphenyldimethacrylate and the N-tolylglycine-glycidylmethacrylate may be present in a solution resulting from the 1:1 volume ratio blend of two solutions containing biphenyldimethacrylate and the N-tolylglycine-glycidyl-methacrylate, independently. The formulation may further comprise acetone and ethanol wherein the volume ratio of acetone:ethanol:BPDM solution:NTG-GMA solution may be 1:1:1:1. The product surface may comprise an ePTFE surface. In some examples, a side of the ePTFE surface may comprise an alternating ridge/valley texture. The ePTFE surface may further comprise backing. The ePTFE surface opposite to the backing may comprise an alternating ridge/valley texture. The backing may comprise silicone, PTFE, or ePTFE. The ePTFE backing may comprise unidirectionally or multidirectionally pulled ePTFE. The product surface may comprise of a multidirectional or an unidirectional pulled ePTFE. The coating may be performed under an inert atmosphere. The inert atmosphere may comprise nitrogen and/or argon.

The coating formulation may comprise a dimethacrylate. The dimethacrylate may be polyethylene glycol dimethacrylate. In such embodiments, the product surface may comprise polypropylene. The coating may be performed under an inert atmosphere. The inert atmosphere may comprise nitrogen and/or argon. The coating formulation may comprise a thiol monomer and an unsaturated monomer, which may or may not be the same as that containing in the thiol group. For such formulations, the method may further comprise subjecting the product surface to high-energy vis/UV radiation, plasma treatment, and/or chemical treatment prior to exposing the product surface to the coating formulation. The thiol monomer may be a polythiol and/or the unsaturated monomer has more than one unsaturated bond. The polythiol may be pentaerythritol tetrakis(3-mercaptopropionate). The unsaturated monomer may be triallyl isocyanurate. The unsaturated monomer may be polyethylene glycol dimethacrylate. The polyethylene glycol dimethacrylate may have a Formula

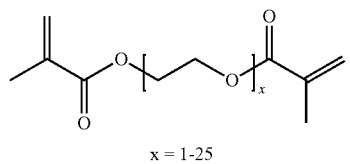

x = 1-25

The coating formulation may further comprise a radical scavenger. The radical scavenger may be hydroquinone, tertbutyl cathetol, or a mixture thereof. The coating formulation may further comprise a solvent. The solvent may be selected from a group consisting of water, acetone, methanol, ethanol, ethyl acetate, dichloromethane, dimethylformamide, methylacetate, heptanes(s), tetrachloroethane, tetrahydrofuran, toluene, trichloroethylene, xylene(s), propanol, acetonitrile, and mixture thereof. For example, the solvent may be methanol, acetone or a mixture thereof or the solvent may comprise one or more of acetone, ethanol, and water.

The coating formulation may further comprise one or more polymerization initiators. The polymerization initiators may be thermal, chemical, photo-, ionic initiators or a mixture thereof. The polymerization initiator may be 2-hydroxy-1-[4-(2-hydroxyethoxy)phenyl]-2-methyl-1-propanone, phenylbis(2,4,6-trimethylbenzoyl)phosphine oxide, diphenyl(2,4,6 trimethylbenzoyl)phosphine oxide, or camphorquinone. The coating formulation may further comprise a therapeutic agent.

The therapeutic agent may be selected from the group consisting of antiplatelets, antithrombins, cytostatic agents, antiproliferative agents, vasodilators, alkylating agents, antimicrobials, antibiotics, antimicotics, disinfectants, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof. For example, the therapeutic agent may comprise antibiotics. The therapeutic agent may be rifampicin, minocycline, minocycline hydrochloride, minocycline hyclate, or a mixture thereof. The product surface may comprise polypropylene or PTFE.

In another aspect, the disclosure provides a method of preparing a coated polymeric surface. The method comprises providing the polymeric surface, exposing the polymeric surface to a coating formulation and polymerizing the coating formulation on the polymeric surface to obtain the coated polymeric surface, wherein the coating formulation comprises a thiol monomer and an unsaturated monomer, which may or may not be the same monomer. The method may further comprise subjecting the polymeric surface to high-energy vis/UV radiation, plasma treatment, and/or chemical treatment prior to exposing the product surface to the coating formulation. The thiol monomer may comprise a polythiol and/or the unsaturated monomer has more than one unsaturated bond. The polythiol may comprise pentaerythritol tetrakis(3-mercaptopropionate). The unsaturated monomer may be any compound comprising one or more double or triple bonds. For example, the unsaturated monomer may be triallyl isocyanurate or polyethylene glycol dimethacrylate. The polyethylene glycol dimethacrylate may have a Formula

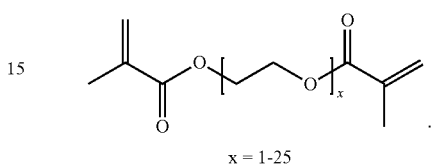

x = 1-25

The thiol monomer may be pentaerythritol tetrakis(3-mercaptopropionate) and the unsaturated monomer triallyl isocyanurate.

The coating formulation may further comprise a radical scavenger. The radical scavenger may comprise hydroquinone, tertbutyl cathetol, or a mixture thereof. The coating formulation may further comprise a therapeutic agent. The therapeutic agent may be selected from the group consisting of antiplatelets, antithrombins, cytostatic agents, antiproliferative agents, vasodilators, alkylating agents, antimicrobials, antibiotics, antimicotics, disinfectants, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof. For example, the therapeutic agent may comprise antibiotics. The therapeutic agent may be rifampicin, minocycline, minocycline hydrochloride, minocycline hyclate, or a mixture thereof.

The coating formulation may further comprise one or more polymerization initiators. The one or more polymerization initiator may be thermal, chemical, photo-, ionic initiators, or a mixture thereof. The polymerization initiator may be selected from a group consisting of 2-hydroxy-1-[4-(2-hydroxyethoxy)phenyl]-2-methyl-1-propanone, phenylbis(2,4,6-trimethylbenzoyl)phosphine oxide, or diphenyl (2,4,6 trimethylbenzoyl)phosphine oxide. The polymerization initiator may be a photo initiator. The photo initiator may be an alpha hydroxyl ketone initiator. The alpha hydroxyl ketone initiator may be Irgacure 2959 (2-hydroxy-1-[4-(2-hydroxyethoxy)phenyl]-2-methyl-1-propanone). The photo initiator may be a phosphine oxide initiator, for example phenyl-bis-(2,4,6-trimethylbenzoyl)-phosphine oxide (PTPO) or diphenyl-(2,4,6-trimethylbenzoyl)-phosphine oxide (TPO). The one or more polymerization initiators may comprise 0.05 wt % of the coating formulation or the one or more polymerization initiators may comprise 1, 0.1, 0.5, 0.01 wt % of the coating formulation.

The composition may further comprise a solvent. The solvent may be selected from a group consisting of water, acetone, methanol, ethanol, ethyl acetate, dichloromethane, dimethylformamide, methylacetate, heptanes(s), tetrachloromethane, tetrahyfrofuran, toluene, trichloroethylene, xylene(s), propanol, acetonitrile and mixture thereof. For example, the solvent may be methanol, acetone, or a mixture thereof.

The polymeric surface may comprise polytetrafluoroethylene, polypropylene, or polyester. The method may further comprise rinsing the coated polymeric surface with a rinse solution. The rinse solution may comprise water, methanol, acetone, 0.01-0.2 M sodium hydroxide, or a combination thereof. The rinsing of the coated product surface may be performed multiple times. The rinse solution for each of the multiple rinses may independently comprise water, methanol, acetone, 0.01-0.2 M sodium hydroxide, or combinations thereof.

In another aspect, the disclosure provides a composition for the preparation of a polymer coating comprising a thiol monomer and an unsaturated monomer, which may or may not be the same as that containing in the thiol group. The thiol monomer may be polythiol and/or the unsaturated monomer has more than one unsaturated bond. The polythiol may be pentaerythritol tetrakis(3-mercaptopropionate). The unsaturated monomer may be triallyl isocyanurate. The unsaturated monomer may be polyethylene glycol dimethacrylate, The polyethylene glycol dimethacrylate may have a Formula

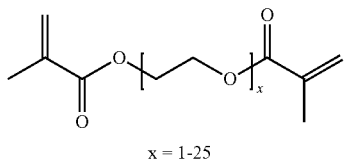

x = 1-25

In some examples, the thiol monomer may be pentaerythritol tetrakis(3-mercaptopropionate) and the unsaturated monomer may be triallyl isocyanurate or the thiol monomer may be pentaerythritol tetrakis(3-mercaptopropionate) and the unsaturated monomer may be polyethylene glycol dimethacrylate.

The composition may further comprise a radical scavenger. For example, hydroquinone, tertbutyl cathetol, or a mixture thereof. The composition may further comprise a solvent. The solvent may be selected from a group consisting of water, acetone, methanol, ethanol, ethyl acetate, dichloromethane, dimethylformamide, methylacetate, heptanes(s), tetrachloromethane, tetrahyfrofuran, toluene, trichloroethylene, xylene(s), propanol, acetonitrile, and mixture thereof. For example, the solvent may be acetone, methanol, or mixture thereof.

The composition may further comprise one or more polymerization initiators. The one or more polymerization initiators may be thermal, chemical, photo-, or ionic initiators, or a mixture thereof. The polymerization initiator may be selected from a group consisting of Irgacure 2959 (2-hydroxy-1-[4-(2-hydroxyethoxy)phenyl]-2-methyl-1-propanone), phenylbis(2,4,6-trimethylbenzoyl)phosphine oxide, or diphenyl(2,4,6 trimethylbenzoyl)phosphine oxide. The polymerization initiator may be a photo initiator. The photo initiator may be an alpha hydroxyl ketone initiator, for example Irgacure 2959 (2-hydroxy-1-[4-(2-hydroxyethoxy) phenyl]-2-methyl-1-propanone). In some examples, the photo initiator may be a phosphine oxide initiator. For example, phenylbis-(2,4,6-trimethylbenzoyl)-phosphine oxide (PTPO) or diphenyl-(2,4,6-trimethylbenzoyl)-phosphine oxide (TPO). The polymerization initiator may amount to 0.05 wt % of the formulation or to 1, 0.1, 0.5, or 0.01 wt % of the formulation.

In another aspect, the disclosure provides a method of preparing a coated product. The method comprises providing a coating formulation, applying the coating formulation to a surface of a product and polymerizing the coating formulation to obtain the coated product, wherein the coating formulation may comprise thiol monomer and an unsaturated monomer, which may or may not be the same monomer. The method may further comprise subjecting the product surface to high-energy vis/UV radiation, plasma treatment, and/or chemical treatment prior to exposing the product surface to the coating formulation. The method may further comprise rinsing the coated product with a rinse solution. The rinse solution may comprise water, methanol, acetone, 0.01-0.2 M sodium hydroxide, or a combination thereof. The rinsing of the coated product surface may be performed multiple times and each of the multiple rinse solution may independently comprise water, methanol, acetone, 0.01-0.2 M sodium hydroxide, or combinations thereof. The thiol monomer may be a polythiol and/or the unsaturated monomer has more than one unsaturated bond. The polythiol may be pentaerythritol tetrakis(3-mercaptopropionate). The unsaturated monomer may be a compound comprising one or more carbon-carbon double and/or triple bonds. The unsaturated monomer may be triallyl isocyanurate. The unsaturated monomer may be polyethylene glycol dimethacrylate, the polyethylene glycol dimethacrylate may have a Formula

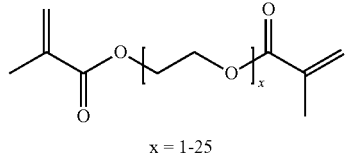

x = 1-25

In some examples, the thiol monomer may be pentaerythritol tetrakis(3-mercaptopropionate) and the unsaturated monomer may be triallyl isocyanurate. In some examples, the thiol monomer may be pentaerythritol tetrakis(3-mercaptopropionate) and the unsaturated monomer may be polyethylene glycol dimethacrylate.

The coating formulation may further comprise a radical scavenger. The radical scavenger may be tertbutyl cathetol, hydroquinone, or a mixture thereof. The coating formulation may be further comprise a therapeutic agent. The therapeutic agent may be selected from the group consisting of antiplatelets, antithrombins, cytostatic agents, antiproliferative agents, vasodilators, alkylating agents, antimicrobials, antibiotics, antimicotics, disinfectants, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof.

The coating formulation may further comprise one or more polymerization initiators. The one or more polymerization initiators may be thermal, chemical, photo, or ionic initiators, or a mixture thereof. The polymerization initiator may be selected from a group consisting of Irgacure 2959 (2-hydroxy-1-[4-(2-hydroxyethoxy)phenyl]-2-methyl-1- propanone), phenylbis(2,4,6-trimethylbenzoyl)phosphine oxide, or diphenyl(2,4,6 trimethylbenzoyl)phosphine oxide. The polymerization initiator may be a photo initiator, for example, an alpha hydroxyl ketone initiator. The alpha hydroxyl ketone initiator may be Irgacure 2959 (2-hydroxy-1-[4-(2-hydroxyethoxy)phenyl]-2-methyl-1-propanone).

The photo initiator may be a phosphine oxide initiator. The phosphine oxide initiator may be phenylbis-(2,4,6-trimethylbenzoyl)-phosphine oxide (PTPO) or diphenyl-(2,4,6-trimethylbenzoyl)-phosphine oxide (TPO).

The coating formulation may further comprise a solvent. The solvent may be selected from a group consisting of water, acetone, methanol, ethanol, ethyl acetate, dichloromethane, dimethylformamide, methylacetate, heptanes(s), tetrachloromethane, tetrahyfrofuran, toluene, trichloroethylene, xylene(s), propanol, acetonitrile, and mixture thereof. The surface of the product may comprise polytetrafluoroethylene or polypropylene.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1. Shows typical ePTFE microstructures which result from unidirectional (FIG. 1a) and multidirectional pulling (FIG. 1b). Images were acquired at 500× original magnification (OM).

FIG. 2. Shows the low magnifications of the DualMesh Biomaterial (FIG. 2a, 25× OM). Both the porous valley/ridge structure and low porosity back side can be seen in low magnification frame. A higher magnification image of the valley structures are shown in FIG. 2b (500× OM).

FIG. 3. Shows the low (500× OM) (FIG. 3a) and high (5,000× OM) (FIG. 3b) magnification images of the smooth side of the DualMesh Biomaterial.

FIG. 5. Demonstrates the effect of using fluid flow and pressurization to force casting solution into multidirectional ePTFE microstructure. Images were acquired at 500× OM. Although pore clogging on the ridge (FIG. 5(a)) and large deposits of coating within the valleys (FIG. 5(b)) still are seen, build-up has been greatly reduced as compared to the results of Example 1.

FIG. 6. Demonstrates the effect of using fluid flow through application of vacuum to bubble air out of the microstructure into the overlaying casting solution, allowing the casting solution to penetrate evenly penetrate into the ePTFE 500× OM. Minor effects on the porosity and the absence of coating build-up are demonstrated on the ridge (FIG. 6(a)) and valleys (FIG. 6(b)).

FIG. 7. Shows the low (500× OM; FIG. 7(a)) and high (5,000× OM; FIG. 7(b)) magnification images of the smooth side of the coated DualMesh sample, of Example 3, showing an absence of coating build-up and large retention of the sub-micron microstructure micrographs.

DETAILED DESCRIPTION OF THE INVENTION

Figure 4:
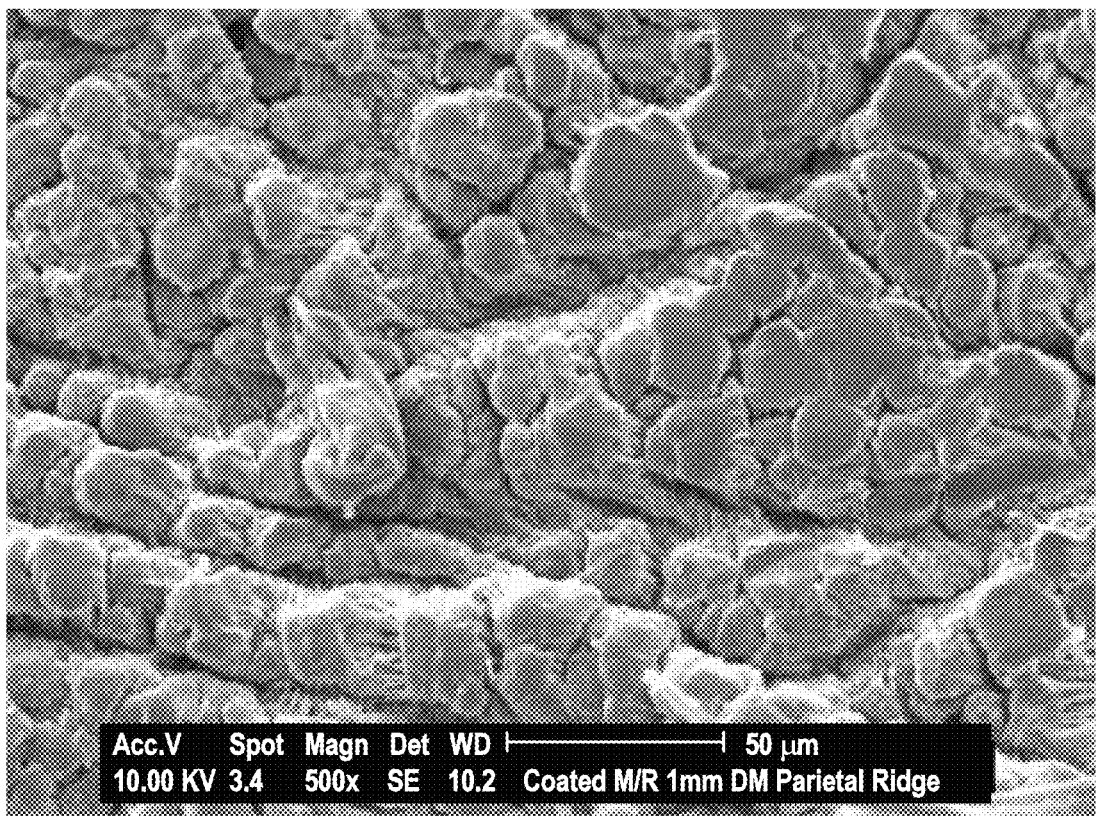
FIG. 4. Demonstrates the inability of the monomer, the solvent, the drug, and the initiator to penetrate the system deep into the microstructures when employing the methods of Example 1. This results in pore clogging and surface build-up of the resulting drug-delivery polymer coating. Images were acquired at 500× OM.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Definitions

As used in the specification and claims, the singular forms "a", "an" and "the" include plural references unless the context clearly dictates otherwise. For example, the term "a cell" includes a plurality of cells, including mixtures thereof.

"Medical device" as used herein can refer to any instrument, apparatus, appliance, material or other article, whether used alone or in combination, including any software necessary for its proper application intended by the manufacturer to be used for human beings for the purpose of: diagnosis, prevention, monitoring, treatment or alleviation of disease, alleviation of pain, diagnosis, monitoring, treatment, alleviation of or compensation for an injury or handicap, investigation, replacement or modification of the anatomy or of a physiological process, control of conception, and which does not achieve its principal intended action in or on the human body by pharmacological, immunological or metabolic means, but which may be assisted in its function by such means.

A medical device may be permanently implantable, temporarily implantable, entirely implantable (such as, for example, an implantable defibrillator), partially implantable (such as, for example, a sensing drainage catheter).

As used herein, the term "biocompatible", when referring to a surface, generally means a surface which causes either no or a minimal reaction when it comes into contact with a human or animal body or its blood, fluids or other biological membranes.

As used herein, the term "compatible" generally refers to a composition possessing the optimum, or near optimum combination of physical, chemical, biological and drug release kinetic properties suitable for a controlled release coating made in accordance with the teachings of the present disclosure. Physical characteristics include durability and elasticity/ductility, chemical characteristics include solubility and/or miscibility and biological characteristics include biocompatibility. The drug release kinetics may be either near zero-order or a combination of first and zero-order kinetics.

As used herein, when any variable occurs more than one time in a chemical formula, its definition on each occurrence is independent of its definition at every other occurrence.

As used herein, a dash ("-") that is not between two letters or symbols is used to indicate a point of attachment for a substituent. For example, —$CONH_2$ is attached through the carbon atom.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 10 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 10 carbon atoms, for example 2 to 8 carbon atoms, such as from 2 to 6 carbon atoms. For example, $C_0$ alkylene indicates a covalent bond and $C_1$ alkylene is a methylene group. Hydrocarbon groups containing one or more double bonds such as alkene groups and alkyne groups are each a subset of alkyl.

As used herein, "cycloalkyl" refers to a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "heterocycloalkyl" refers to a single, non-aromatic ring, usually with 3 to 8 ring atoms, containing at least 2 carbon atoms in addition to 1-3 heteroatoms independently chosen from oxygen, sulfur, and nitrogen, as well as combinations comprising at least one of the foregoing heteroatoms. The ring may be saturated or have one or more carbon-carbon double bonds. Suitable heterocycloalkyl groups include but are not limited to, for example, pyrrolidinyl, morpholinyl, piperidinyl, piperazinyl, azetidinyl, diazepanyl, diazocanyl, pyrrolidinyl, morpholinyl, piperidinyl, piperazinyl, imidazolidinyl, pyrazolidinyl, dihydrofuranyl, and tetrahydrofuranyl. Substituted heterocycloalkyl can also include ring systems substituted with one or more oxo (=O) or oxide (—O—) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently chosen from oxygen, sulfur, and nitrogen, as well as combinations comprising at least one of the foregoing heteroatoms; and the other ring, usually with 3 to 7 ring atoms, optionally contains 1-3 heteroatoms independently chosen from oxygen, sulfur, and nitrogen and is not aromatic.

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 4- to 8-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

As used herein, "heteroaryl" refers to: 5- to 7-membered aromatic, monocyclic rings containing one or more, for example, from 1 to 4, or in certain embodiments, from 1 to 3, heteroatoms chosen from N, O, and S, with the remaining ring atoms being carbon; bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 4- to 8-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, pyridyl, pyrazinyl, pyrimidinyl, pyrazolinyl, imidazolyl, isoxazolyl, oxazolyl, thiazolyl, thiadiazolyl, tetrazolyl, thienyl, benzothiophenyl, furanyl, pyrrolyl, benzofuranyl, benzoimidazolyl, indolyl, pyridazinyl, triazolyl, quinolinyl, quinoxalinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene.

Substituted heteroaryl also includes ring systems substituted with one or more oxide (—O—) substituents, such as pyridinyl N-oxides.

As used herein, "substituted" refers to any one or more hydrogens on the designated atom or group are replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility.

The term "aromatic" is used in its usual sense, including unsaturation that is essentially delocalized across multiple bonds, such as around a ring.

The term "substituent" refers to an atom, radical or chemical group which replaces a hydrogen in a substituted chemical group, radical, molecule, moiety or compound.

Unless otherwise stated, the term "radical", as applied to any molecule or compound, is used to refer to a part, fragment or group of the molecule or compound rather than to a "free radical". A radical may be linked to another moiety through a covalent bond.

Compounds described herein include, but are not limited to, their optical isomers, racemates, and other mixtures thereof. In those situations, the single enantiomers or diastereomers, i.e., optically active forms can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with carbon-carbon double bonds. Where compounds described herein exist in various tautomeric forms, the term "compound" is intended to include all tautomeric forms of the compound.

Additionally, useful compositions also, optionally, include one or more salts in an amount required to bring solubility of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

A "polymer" as used herein, can refer to a series of monomers that have been cross-linked or polymerized. The polymer can be a homopolymer or a copolymer. A "copolymer" can refer to a macromolecule produced by the simultaneous or step-wise polymerization of two or more distinct monomers. A homopolymer can refer to a macromolecule produced by the polymerization of a single repeating monomer unit.

"Polymerization", as used herein, generally refers to a process of combining monomers into a covalently bonded chain or network. During the polymerization process, some chemical groups may or may not be lost from each monomer.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect", as used herein, refers to a physiologic effect, including but not limited to the cure, mitigation, amelioration, or prevention of disease, or treatment of a symptom of a disease in humans or other animals. Determination of a therapeutically effective amount is well within the capability of those skilled in the art, especially in light of the detailed disclosure provided herein.

Overview

The disclosure provides polymeric coatings, coated products and methods for their preparation. The polymeric coatings and the coated products of the present disclosure may have eluting properties. The coated product may elute one or more therapeutic agents from the product coating. The elution kinetics of the therapeutic agent may be manipulated by controlling the composition and/or structure of the polymeric coating. For example, the coating may provide for extended release of the one or more therapeutic agents over time.

The coatings described herein can confer improved characteristics to the coated product as compared to a corresponding non-coated product. For example, the coated product can have improved biocompatibility when implanted into a live subject as compared to a corresponding non-coated product. The coating can be non-degradable, which can prevent leaching of the coating components into the surrounding area. Alternatively, the coating can be biodegradable. Further, the coating can be sufficiently durable to withstand the rigors of device implantation and operation (e.g., expansion), without significant degradation. The coatings described herein may result in polymer of higher cross-linking degree and may also exhibit extended drug elution times. The coatings described in the disclosure may be used to control drug elution profiles.

The polymeric coatings of the instant disclosure may be applied to a variety of products and surfaces. The polymeric coatings may be applied on medical devices, for example to a coated soft tissue mesh. The material of the soft tissue mesh can be any of the material, for example ePTFE, polypropylene, expanded polypropylene. The soft tissue mesh may be a hernia mesh such as an ePTFE hernia mesh or a polypropylene hernia mesh.

The disclosure also provides coating formulations for the preparation of polymer coatings. The coating formulations generally comprise one or monomer components. In some cases, the coating formulation is a thiol-ene formulation. The thiol-ene formulation comprises of a thiol monomer. The thiol monomer may be a polythiol compound, for example any suitable type of dithiol, trithiol or a tetrathiol compound may be used. In some embodiments, the thiol is pentaerythritol tetrakis (3-mercaptoacetate) [PTMA]. The thiol-ene formulations may also comprise an unsaturated monomer, for example a monomer comprising one or more double bonds or triple bonds. The thiol-ene formulations may result in a polymer coating that is biodegradable in nature. The unsaturated monomer may be a methacrylate, for example a dimethacrylate. In some cases, the dimethacrylate may be polyethylene glycol dimethacrylate (PEG DM). The unsaturated compound may be triallyl isocyanurate.

Also provides herein are methods of forming the polymeric coatings. The methods and the formulations described herein may be used to coat a variety of devices. The methods and the formulation described herein may be used to coat polymeric surfaces. In some cases, the polymeric surface may be a polyester (e.g., polyethylene terephthalate or biodegradable), PTFE, an ePTFE or polypropylene surface. The product surface can be treated to improve adhesion strength by incorporating use of high-energy vis/UV radiation, plasma, or chemical treatment to create a reactive polyester, polypropylene, PTFE, or ePTFE surface with a higher surface energy. For example, the coating methods and formulations of the instant disclosure may be used for coating PTFE surfaces. The methods disclosed herein may also be used to coat ePTFE surfaces. The methods disclosed herein may be used for coating ePTFE materials formed through unidirectional pulling of PTFE. The coating methods of the instant disclosure may also be used in coating ePTFE materials formed by multidirectional or radial pulling of PTFE materials. The multidirectional pulling of PTFE may be achieved by pulling of PTFE in two perpendicular directions within the plane defined by the continuum of an ePTFE sheet.

The coating methods disclosed herein may enable the casting solution to adequately penetrate into the microstructure of the surface thereby preventing or minimizing the surface build-up of the casting solution. The casting solution may be coating formulations. The method may also prevent and or minimize the clogging of the microstructure pores. This reduction in the surface-build up may be obtained by careful selection of the solvent system for the casting solution. The solvent system may be selected such that it is miscible with the casting formulations, passively penetrates into the microstructure due to low viscosity and low surface tension, and evaporates within a relatively short amount of time due to having a relatively high vapor pressure. The solvent system may be a single solvent or a combination of two or more solvents. For example it may be ethanol, acetone or a mixture thereof, such as a 1:1 mixture of ethanol and acetone.

The adequate penetration of the casting solution into the microstructure may also be obtained by physically assisting the monomer/solvent/drug casting solution to penetrate within the surface microstructure. The physical assistance may be any suitable external means, like via application of external pressure. The desired amount of pressure may be applied by any suitable mechanism for example, by a use of a syringe. The pressure may in the form of pressure differential across the polymeric surface to be coated, with casting solution applied to the high pressure side. The pressure may also be applied by using vacuum to induce fluid flow through expansion of the air within the surface microstructure.

The disclosure also provides methods for loading therapeutic agents on the polymeric coatings. The loading may be obtained via polymerization of the coating in presence of one or more therapeutic agents. The loading may also be obtained by post curing loading of therapeutic agents on the coated surface. The post curing methods of the disclosure may comprise coating a surface with the polymeric coating and submerging the coated surface in a solution or exposing the coating to a solution of one or more therapeutic agent in a suitable solvent for an appropriate period of time. The solvent many be any suitable organic solvent for example methanol, ethanol, acetone, or mixtures thereof. The time for soaking may vary from a few seconds to several hours. For example from 1 sec-1 day, for example soaking may be performed for 3, 6, 9, 12, 15, 18, 21 or 24 hours. The post curing method of the disclosure may further involve drying of the soaked surface, for example air drying of the soaked surface. The dried samples may be further rinsed, once or more, with a suitable solvent, for example with methanol, acetone, aqueous hydroxide, and mixtures thereof, and the rinsed surface may be dried again. When aqueous hydroxide solutions are employed, further rinsing in deionized water is advised to neutralize the basic (high pH) of the hydroxides and remove cations ions.

The post curing loading methods of the disclosure may be especially useful for drugs that are susceptible to degradation in the presence of the free radical, for example drugs containing a free amine group. The loading of such drugs by method that involve polymerization of casting in the presence of the drugs, may be problematic due to hydrogen abstraction between the amine and the living polymer's radical end which may result in drug degradation. In some examples, the post curing loading methods of the disclosure may produce equivalent or greater drug loading on the polymeric coating as the loading obtained when polymerization of the coating occurs with the drugs present. The post curing loading methods of the disclosure may provide superior drug eluting castings, as compared to those achieved when the polymerization of the coating occurs with the drugs present, due to decrease in the drug degradation.

Coating Compositions

The disclosure provides numerous compositions for the preparation of polymer coatings. Such compositions can be referred to herein as "casting solution", "coating compositions", or "coating formulations". The compositions generally comprise one or monomer components. The monomer component can comprise one monomer or more than one monomer. In some cases the monomer component does not comprise more than one monomer. Any monomer that is capable of forming a polymer is contemplated in the disclosure.

Thiol-Ene Formulations

In some cases the coating compositions of the disclosure may comprise thiol-ene formulations. The thiol-ene formulations may be attractive due to a number of reasons including lack of oxygen inhibition, lesser potential to participate in side reactions, high efficiency, and fast kinetics. Due to the nature of step-growth polymerization, thiol-ene polymerizations may result in near complete monomer conversion with very high degrees of polymerization. The required functional groups of a thiol and unsaturated group allow for the design of less toxic monomers. Thiol-ene system polymerizations may be easily initiated with radicals and/or ionic species. Additionally a variety of thiol-ene monomers may be available as off-the-shelf items from multiple suppliers. By using these off-the-shelf monomers it may possible to produce coatings at a much lower cost. The thiol-ene systems may also be accommodating to the production of highly cross-linked, non-biodegradable polymers.

The thiol-ene coating compositions may comprise one or more thiol monomer and one or more unsaturated monomer. The monomers may be chosen such that the monomer blend may be a liquid at room temperature. The monomers may also be chosen such that the resulting polymer may be non-biodegradable. Monomers may also be selected to ensure that the resulting polymer may be biodegradable and/or biocompatible. The monomers and resulting polymers may also be optimized to have low surface energies to allow spreading on polymeric surface, for example on polypropylene, PTFE, or ePTFE. In some example, the monomers may also be chosen so that the resulting polymer may be highly cross-linked. The high cross-linking may be useful to extend drug elution profiles and provide the ability to fine tune the elution profile by altering therapeutic agent: thiol-ene polymer ratio. The monomer system may also be chosen to be compatible with radical initiation systems. The monomer system may also be selected so that the resulting polymer may be flexible and less vulnerable to flaking, chipping or delamination of the polymeric coatings, for example from polypropylene monofilaments and structures made thereof. In some cases, the monomer components may be chosen to ensure a low glass transition temperature (Tg).

The thiol-ene coating compositions may comprise one or more thiol monomer. The thiol monomer may be a polythiol compound. The polythiol compound may be of any suitable type for example a dithiol, trithiol or a tetrathiol compound may be used. In some embodiments, the polythiol may be selected from one or more of the following:

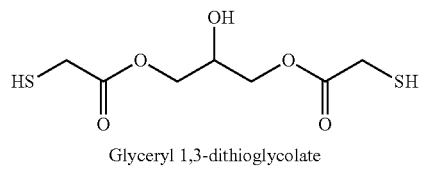

Glyceryl 1,3-dithioglycolate

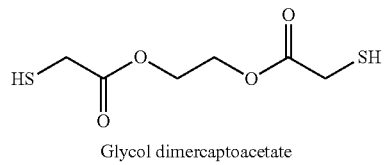

Glycol dimercaptoacetate

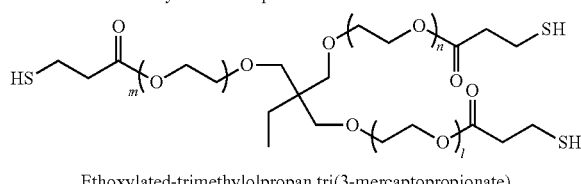

Ethoxylated-trimethylolpropan tri(3-mercaptopropionate)

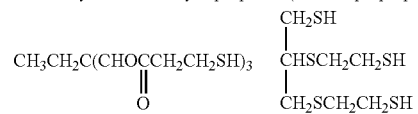

Trimethylolpropane tris (3-mercaptopropionate) [TTMP]    4-mercaptomethyl-3,6-dithia-1,8-octanedithiol [MDO]

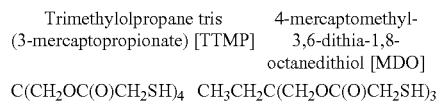

Pentaerythritol tetrakis (3-mercaptoacetate) [PTMA]    Trimethylolpropane tris (3-mercaptoacetate) [TI'MA]

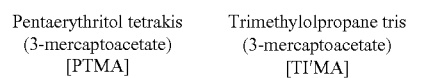

4-t-butyl-1,2-benzenedithiol    Bis(2-mercaptoethyl) sulfide

4,4'-thiodibenzenethiol    benzenedithiol

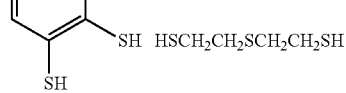

Glycol dimercaptoacetate    Glycol dimercaptopropionate ethylene bis (3-mercaptopropionate)

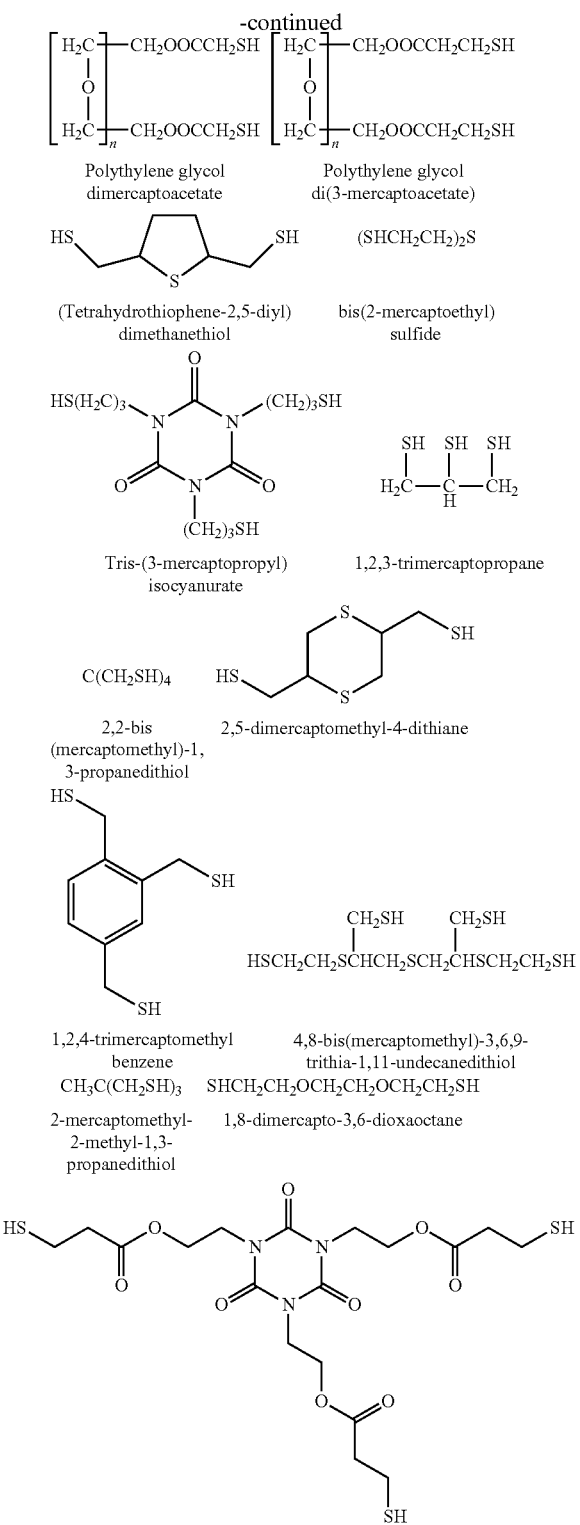

In some embodiments, the thiol is $C(CH_2OC(O)CH_2SH)_4$

Pentaerythritol tetrakis (3-mercapto acetate) [PTMA]

The thiol component of the thiol-ene formulation may account for 0.005-80% of composition by wt/wt or wt/vol. A thiol component may account for 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 68%, 69%, 70%, 71%, 72%, 73%, 74%, 75%, 78%, 79%, or 80% of the composition upon formulation. A thiol component can account for 0.05-0.5%, 0.1-2%, 1-5%, 5-10%, 10-15%, 15-20%, 20-25%, 25-30%, 30-35%, 35-40%, 40-45%, 45-50%, 50-55%, 55-60%, 60-65%, 65-70%, 70-75%, or 75-80% of the composition upon formulation. For example, a thiol component can account for 67.22% of the composition upon formulation. In some examples, the thiol component of the thiol-ene formulation is pentaerythritol tetrakis(3-mercaptopropionate) and it amounts to 67.22% of the composition upon formulation. In some cases the thiol-ene formulation is pentaerythritol tetrakis(3-mercaptopropionate) and it amounts to 32% of the composition upon formulation.

The thiol-ene formulations may also comprise an unsaturated monomer, for example a monomer with unsaturated groups such as a monomer comprising one or more double bond, triple bonds or both. The unsaturated monomer may be a methacrylate, for example a dimethacrylate. In some cases, the dimethacrylate may be polyethylene glycol dimethacrylate (PEG DM) with the general formula:

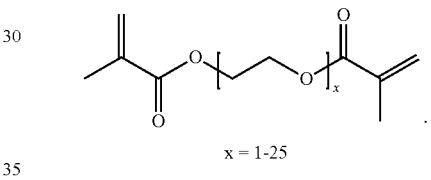

x = 1-25

The variable x may be an integer of value 1-25. In some cases x is a integer of value 5-10, 5-15, 5-20, 5-25, 10-15, 10-20, 10-25, 15-20, 15-25, or 20-25. For example 1, 2, 3, 4, 5, 6, 7, 8, 9, 10, 11, 12, 13, 14, 15, 16, 17, 18, 19, 20, 21, 22, 23, 24, or 25. In some cases x is 9. The molecular weight of the PEG DM may be in the range of about 100-1500 Da. For example, in the range of about 100-1400 Da, 100-1300 Da, 100-1200 Da, 100-1100 Da, 100-1000 Da, 100-900 Da, 100-800 Da, 100-700 Da, 100-600 Da, 100-500 Da, 100-400 Da, 100-300 Da, 100-200 Da, 200-1500 Da, 200-1400 Da, 200-1300 Da, 200-1200 Da, 200-1100 Da, 200-1000 Da, 200-900 Da, 200-800 Da, 200-700 Da, 200-600 Da, 200-500 Da, 200-400 Da, 200-300 Da, 300-1500 Da, 300-1400 Da, 300-1300 Da, 300-1200 Da, 300-1100 Da, 300-1000 Da, 300-900 Da, 300-800 Da, 300-700 Da, 300-600 Da, 300-500 Da, 300-400 Da, 400-1500 Da, 400-1400 Da, 400-1300 Da, 400-1200 Da, 400-1100 Da, 400-1000 Da, 400-900 Da, 400-800 Da, 400-700 Da, 400-600 Da, 400-500 Da, 500-1500 Da, 500-1400 Da, 500-1300 Da, 500-1200 Da, 500-1100 Da, 500-1000 Da, 500-900 Da, 500-800 Da, 500-700 Da, 500-600 Da, 600-1500 Da, 600-1400 Da, 600-1300 Da, 600-1200 Da, 600-1100 Da, 600-1000 Da, 600-900 Da, 600-800 Da, 600-700 Da, 700-1500 Da, 700-1400 Da, 700-1300 Da, 700-1200 Da, 700-1100 Da, 700-1000 Da, 700-900 Da, 700-800 Da, 800-1500 Da, 800-1400 Da, 800-1300 Da, 800-1200 Da, 800-1100 Da, 800-1000 Da, 800-900 Da, 900-1500 Da, 900-1400 Da, 900-1300 Da, 900-1200 Da, 900-1100 Da, 900-1000 Da, 1000-1500 Da, 1000-1400 Da, 1000-1300 Da, 1000-1200 Da, 1000-1100 Da, 1100-1500 Da, 1100-1400 Da, 1100-1300 Da, 1100-1200 Da, 1200-1500 Da, 1200-1400 Da, 1200-1300 Da, 1300-1500, 1300-1400, or 1400-1500 Da. In some examples, the molecular weight of the PEG DM may be about 500 Da.

The unsaturated monomer may be an acrylate, for example a diacrylate. In some cases, the diacrylate may be polyethylene glycol diacrylate (PEG DA) with the general formula:

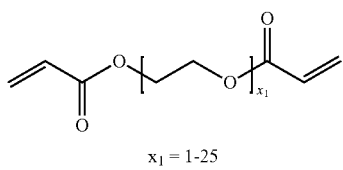

$x_1 = 1\text{-}25$

The variable $x_1$ may be an integer of value 1-25. In some cases $x_1$ is a integer of value 5-10, 5-15, 5-20, 5-25, 10-15, 10-20, 10-25, 15-20, 15-25, or 20-25. For example 1, 2, 3, 4, 5, 6, 7, 8, 9, 10, 11, 12, 13, 14, 15, 16, 17, 18, 19, 20, 21, 22, 23, 24, or 25. The molecular weight of the PEG DA may be in the range of about 100-1500 Da. For example, in the range of about 100-1400 Da, 100-1200 Da, 100-1000 Da, 100-800 Da, 100-600 Da, 100-400 Da, 100-200 Da, 200-1400 Da, 200-1200 Da, 200-1000 Da, 200-800 Da, 200-600 Da, 200-400 Da, 300-1400 Da, 300-1200 Da, 300-1000 Da, 300-800 Da, 300-600 Da, 300-400 Da, 400-1400 Da, 400-1200 Da, 400-1000 Da, 400-800 Da, 400-600 Da, 500-1400 Da, 500-1200 Da, 500-1000 Da, 500-800 Da, 500-600 Da, 600-1400 Da, 600-1200 Da, 600-1000 Da, 600-800 Da, 700-1400 Da, 700-1200 Da, 700-1000 Da, 700-800 Da, 800-1400 Da, 800-1200 Da, 800-1000 Da, 900-1400 900-1200 Da, 900-1000 Da, 1000-1400 Da, 1000-1200 Da, 1100-1400 Da, 1100-1200 Da, 1200-1400 Da, 1300-1400, or 1400-1500 Da.

In some embodiments, the unsaturated monomer is a biodegradable ene or a biodegradable diene. For example, the monomer may be

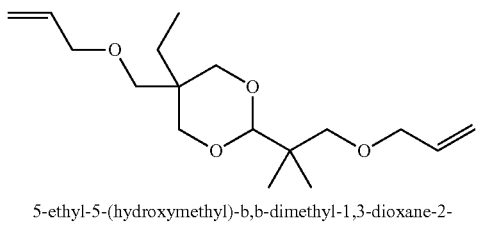

5-ethyl-5-(hydroxymethyl)-b,b-dimethyl-1,3-dioxane-2-ethanol diallyl

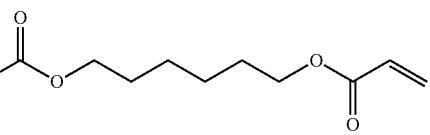

1,6-hexanediol diacrylate

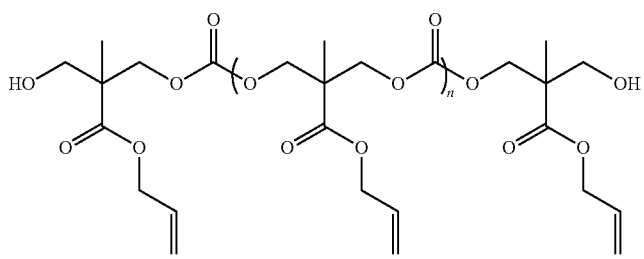

Poly(5-methyl-5-allyloxycarbonyl-1,3-dioxan-2-one) macromonomer

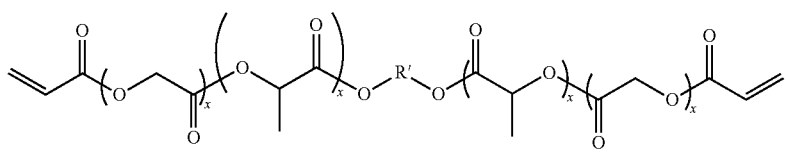

PLGA/P—PLGA macromer

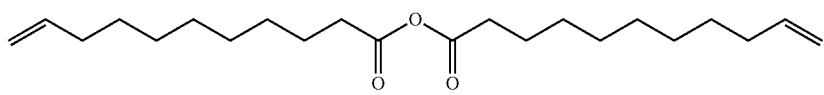

undec-10-enoic anhydride

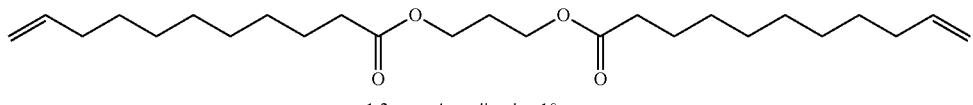

1,3-propylene diundec-10-enoate

-continued

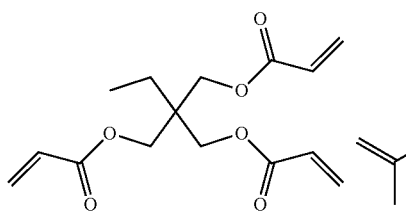
Trimethylolpropane triacrylate

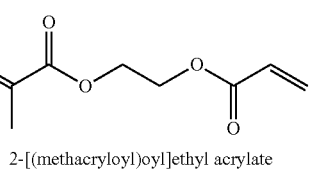
2-[(methacryloyl)oyl]ethyl acrylate

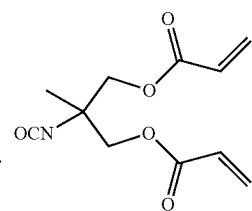
1,1-bis(acryloyloxymethyl)ethyl isocyanate

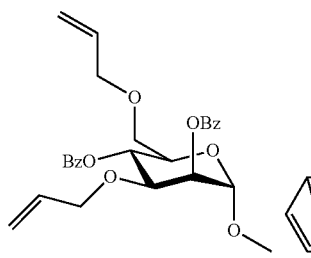
3,6-di-O-ally-2,4,di-O-benzyoly-α-D-mannopyranoside

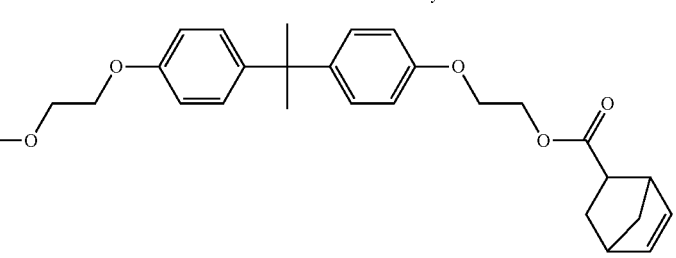
bis-2,2-[4-(2-[nor-born-2-ene-5-carboxylate]ethoxy)phenyl]propane

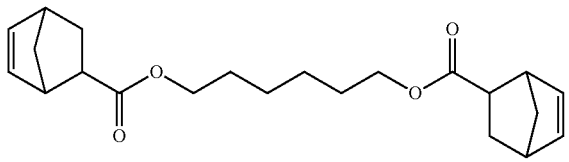
1,6-hexanediol-di-(norborn-2-ene-5-carboxylate)

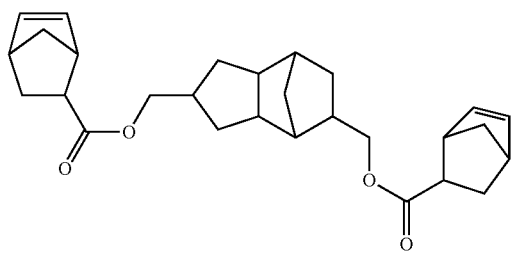
tricyclodecane-dimethanol-di-(norborn-2-ene-5-carboxylate)

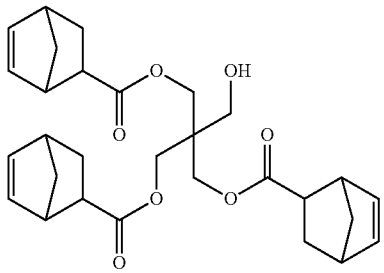
penta-erythritol tri-(norborn-2-ene-5-carboxylate)

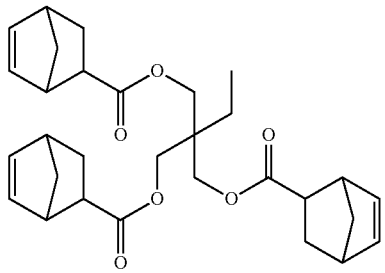
tri-(norborn-2-ene-5-carboxylate)

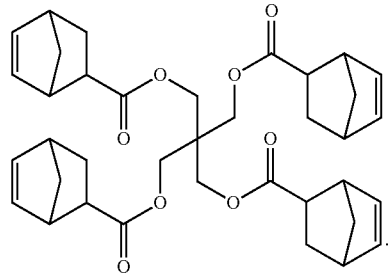
pentaerythritol tetra-(norborn-2-ene-5-carboxylate)

In some embodiments, the unsaturated monomer may be

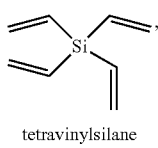
tetravinylsilane

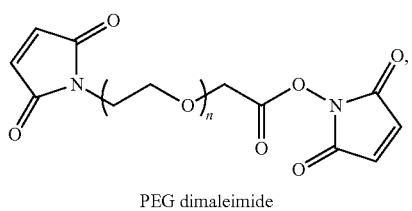
PEG dimaleimide

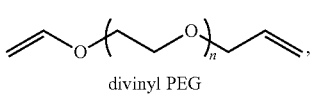
divinyl PEG

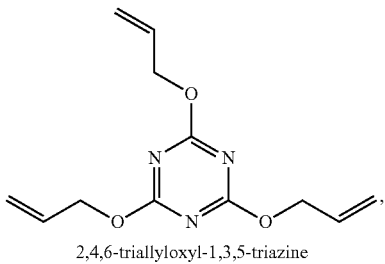
2,4,6-triallyloxyl-1,3,5-triazine

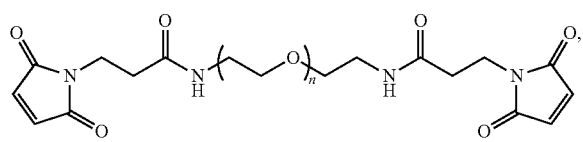

PEG dimaleimide

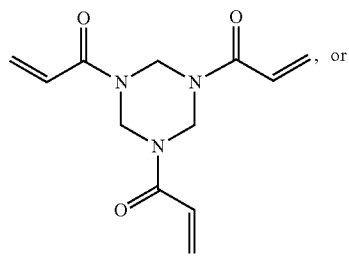

1,3,5-triacryloylhexahydro-1,3,5-triazine

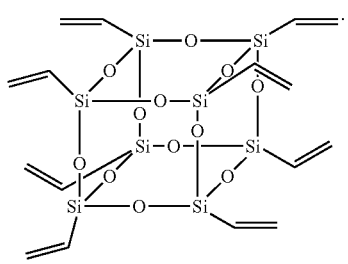

octavinyl polyhedral oligosilsesquioxanes

In some examples, the unsaturated monomer is triallyl isocyanurate.

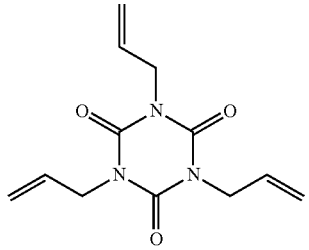 [SMILES: C=CCn1c(=O)n(CC=C)c(=O)n(CC=C)c1=O]

In some embodiments, the unsaturated monomer is an alkyne or a dialkyne. For example, the unsaturated monomer may be

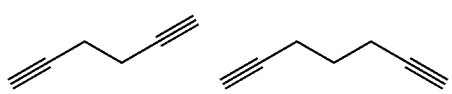

hexadiyne , heptadiyne ,

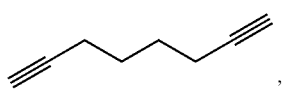

octadiyne ,

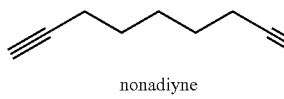

nonadiyne ,

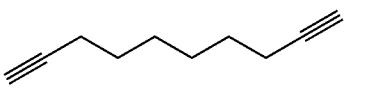

decadiyne ,

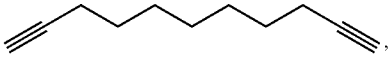

undecadiyne ,

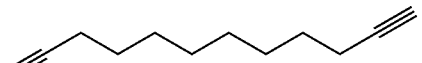

, or dodecadiyne

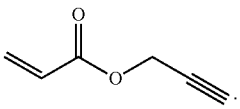

propargyl acrylate.

In some embodiments the unsaturated monomer may be

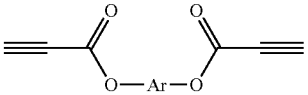

wherein Ar is

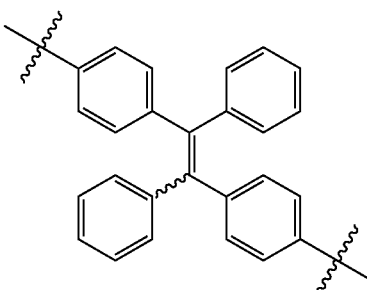

,

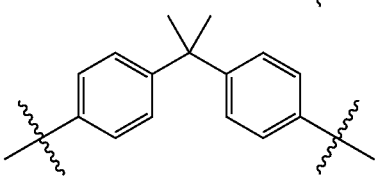

,

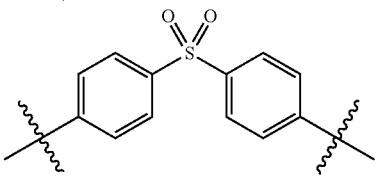

, or

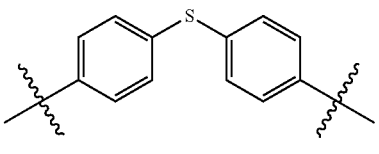

,

In some embodiments the unsaturated monomer may be

≡—R—≡ wherein R is

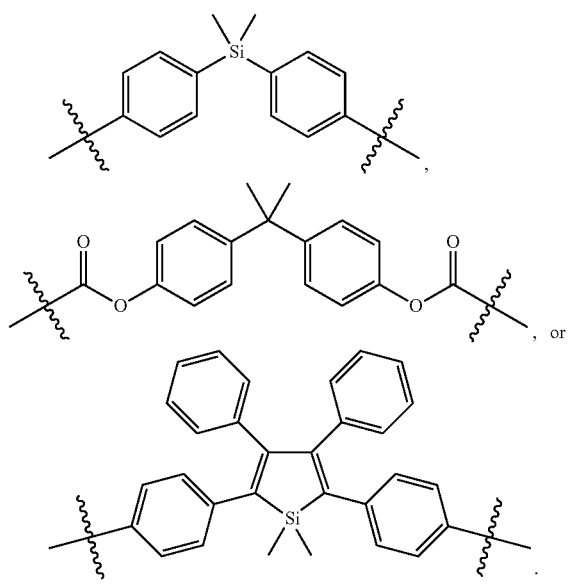

, or

The unsaturated monomer may also be selected from one or more of the following:

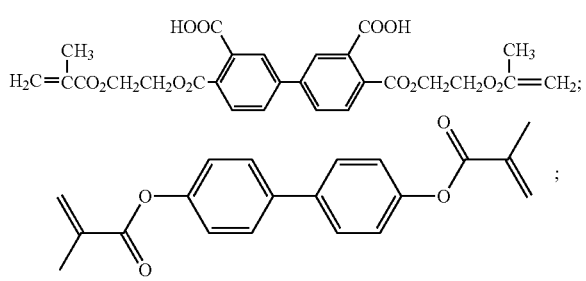

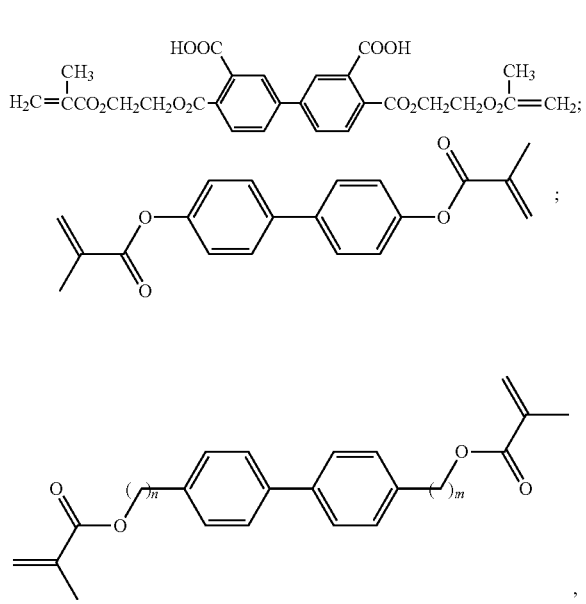

wherein each of n and m is independently 1-10;

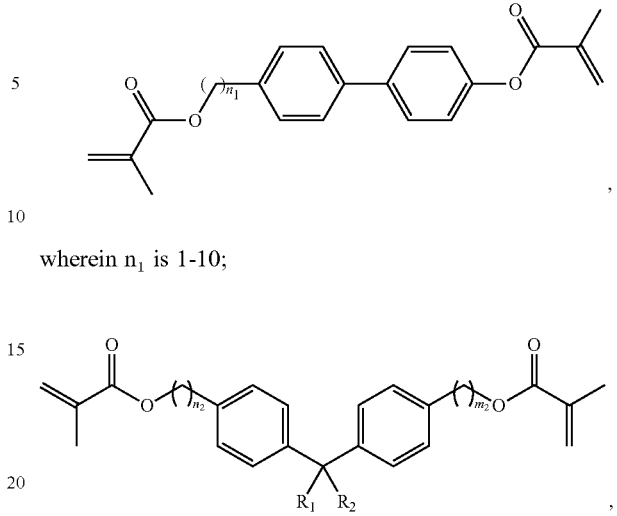

wherein $n_1$ is 1-10;

wherein each of $n_2$ and $m_2$ is independently 1-10, each of $R_1$ and $R_2$ is alkyl or $R_1$ and $R_2$ in combination with carbons they are attached to form a carbo- or heterocyclic ring, or $R_1$ and $R_2$ are each hydrogen;

wherein each of $R_3$ and $R_4$ is alkyl or $R_3$ and $R_4$ in combination with the carbon they are attached to, form a cyclic- or heterocyclic ring, or $R_3$ and $R_4$ are each hydrogen;

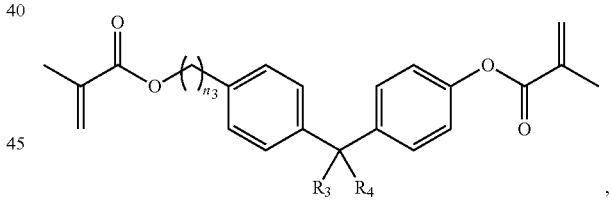

wherein each of $R_3$ and $R_4$ is alkyl or $R_3$ and $R_4$ in combination with the carbon they are attached to, form a cyclic- or heterocyclic ring, or $R_3$ and $R_4$ are each hydrogen;

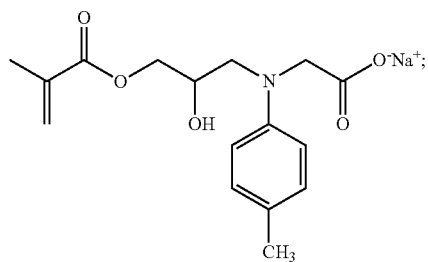

NTG-GMA-sodium salt/n-tolyglycine glycidylmethacrylate

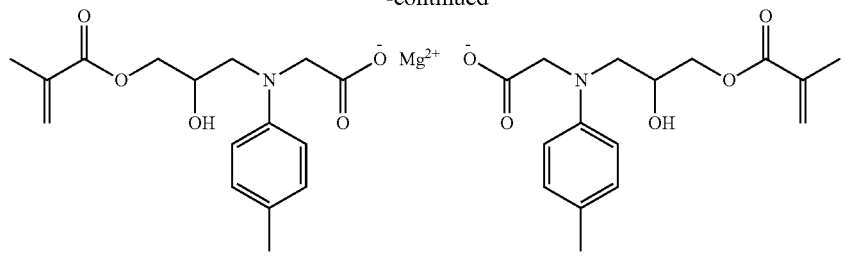

NTG-GMA-magnesium salt

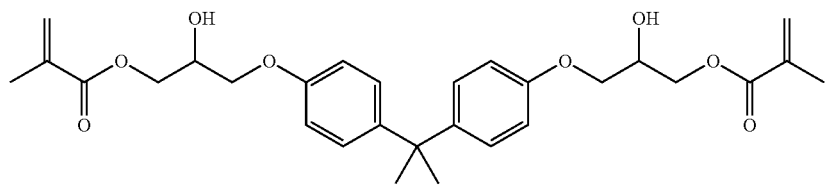

Bis-GMA/bisphenol-A-glycidylmethacrylate

The unsaturated monomer may account for 0.005-80% of the thiol-ene formulation composition by wt/wt or wt/vol. A unsaturated monomer may account for 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 68%, 69%, 70%, 71%, 72%, 73%, 74%, 75%, 78%, 79%, or 80% of the thiol-ene formulation composition. A unsaturated monomer can account for 0.05-0.5%, 0.1-2%, 1-5%, 5-10%, 10-15%, 15-20%, 20-25%, 25-30%, 30-35%, 35-40%, 40-45%, 45-50%, 50-55%, 55-60%, 60-65%, 65-70%, 70-75%, or 75-80% of the thiol-ene formulation composition. For example, an unsaturated monomer can account for 32.73% of the composition upon formulation. In some examples, the unsaturated monomer of the thiol-ene formulation is triallyl isocyanurate and it amounts to 32.73% of the composition upon formulation. In some cases the unsaturated monomer of the thiol-ene formulation is polyethylene glycol dimethacrylate and it amounts to 68% of the composition upon formulation.

The thiol formulations of the disclosure may be designed to vary the molar ratio of the reactive unsaturated groups in the unsaturated monomer and the reactive thiol groups in the thiol component. For example the ratio may be about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, or about 10:1. In some examples, the molar ratio of reactive unsaturated groups in the unsaturated monomer and the reactive thiol groups in the thiol component is about 1:1.

The thiol-ene formulation of the disclosure may comprise one or more additives. For example, the formulation may comprise one or more radical scavengers. Non-limiting examples of suitable radical scavengers include hydroquinone, hydroquinone methyl ether mono-tertiary-butylhydroquinone (MTHQ), 2, 5-di-tertiary-butylhydroquinone (DTBHQ), toluhydroquinone (THQ), tert-butylcatechol (example, p-tert-butylcatechol), quinoid compounds such as benzoquinone and alkyl-substituted benzoquinones, as well as other radical scavenger compounds known in the art. Typically, these components may be used in amounts in the range of 0.001 to 2 percent by weight of the composition. For example, the radical scavengers may amount to 0.001%, 0.002%, 0.003%, 0.004%, 0.005%, 0.006%, 0.007%, 0.008%, 0.009%, 0.01%, 0.015%, 0.020%, 0.025%, 0.030%, 0.035%, 0.040%, 0.045%, 0.050%, 0.055%, 0.060%, 0.070%, 0.075%, 0.080%, 0.85%, 0.090%, 0.1%, 0.15%, 0.20%, 0.25%, 0.30%, 0.35%, 0.40%, 0.45%, 050%, 0.55%, 0.60%, 0.65%, 0.70%, 0.75%, 0.80%, 0.85%, 0.90%, 0.95%, 1%, 1.1%, 1.2%, 1.3%, 1.4%, 1.5%, 1.6%, 0.17%, 1.8%, 1.9%, or 2% by weight of the thiol-ene formulation. For example, the thiol-ene formulation may comprise 0.05 wt % of hydroquinone. The thiol-ene formulation may also comprise 0.05 wt % of tert-butylcatechol. In some cases the thiol-ene composition may comprise 0.05 wt % of a mixture of hydroquinone and tert-butylcatechol (1:1 mixture by mole).

Non Thiol-Ene Formulations

The disclosure also provides polymeric compositions other than thiol-ene formulations. The polymeric compositions comprise of one or more monomers. The monomer component can comprise a dimethacrylate. The dimethacrylate can be an aromatic dimethacrylate. The aromatic dimethacrylate can be, e.g., any compound of Formulas I-XII:

(Formula I)

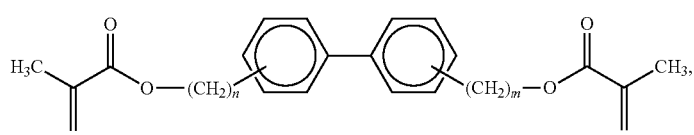

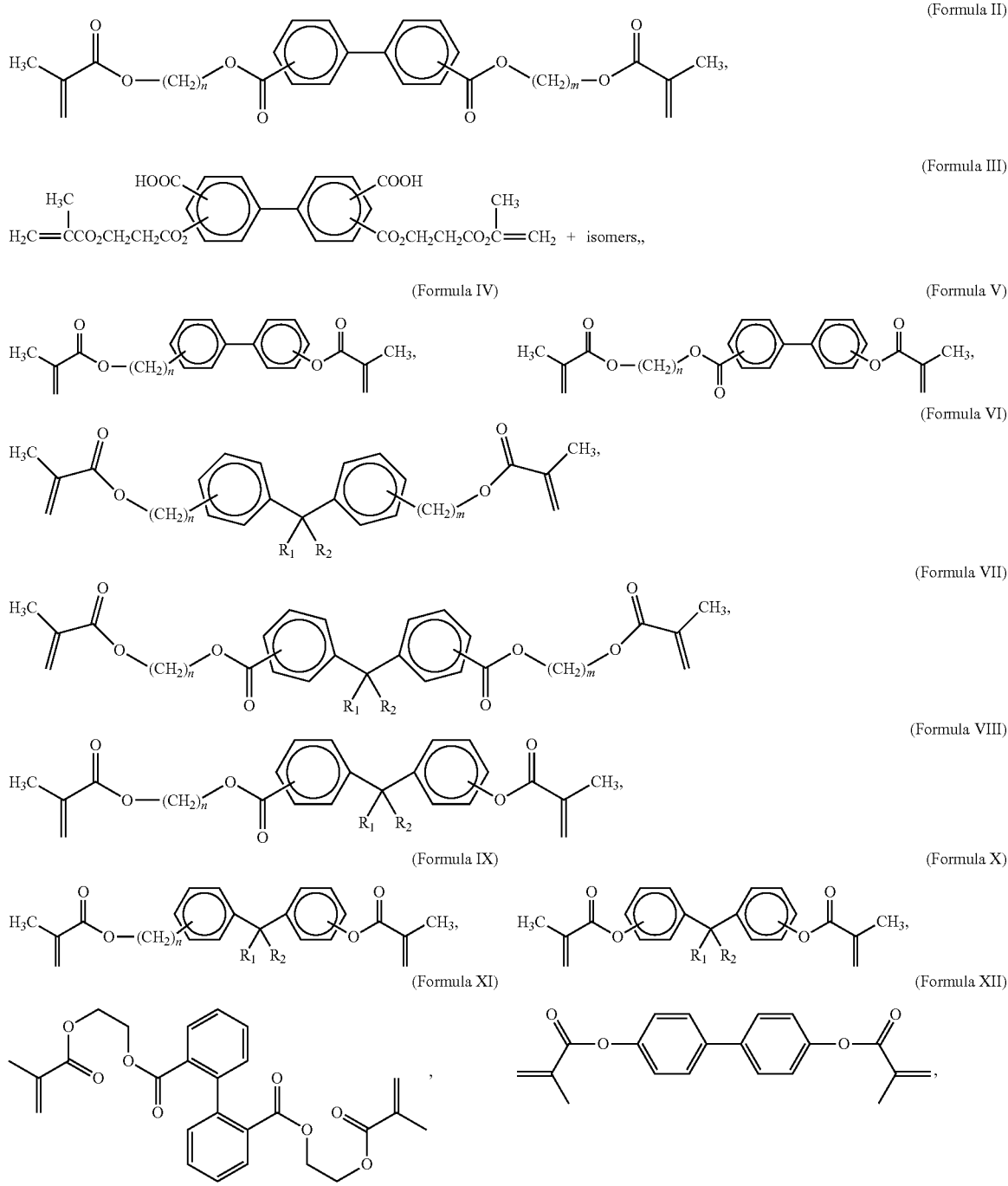

and any combinations and/or salts thereof;
wherein each n is independently 1-10;
each m is independently 1-10;
and wherein each $R_1$ and each $R_2$ is independently selected from the group consisting of H, $C_1$-$C_{10}$ alkyl, aryl, and heteroaryl, wherein said $C_1$-$C_{10}$ alkyl, aryl, heteroaryl, when present, is optionally substituted with halo, aryl, heteroaryl, —$NR_{21}R_{22}$, —$OR_{23}$, —$SR_{24}$, —$S(O)R_{25}$, —$S(O)_2R_{26}$, —$PR_{27}R_{28}$, —$NR_{29}(C=O)R_{30}$, —$NR_{31}S(=O)_2R_{32}$, or —$C(=O)NR_{33}R_{34}$; or $R_1$ and $R_2$ in combination with the carbon to which they are attached form a $C_3$-$C_8$ cycloalkyl or $C_3$-$C_8$ heterocycle; each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, and $R_{34}$ is independently selected from the group consisting of H, $C_1$-$C_6$ alkyl, —$C(=O)R_{40}$, aryl, and heteroaryl; $R_{40}$ is $C_1$-$C_6$ alkyl.

The aromatic dimethacrylate can be biphenyldimethacrylate, bisphenyldimethacrylate, biphenol-dimethacrylate, bisphenol-dimethacrylate, triethyleneglycol dimethacrylate (TEGDMA), urethane dimethacrylate (UDMA), bisphenol-glycidyldimethacrylate (Bis-GMA). The composition can, in some cases, comprise two or more dimethacrylates.

In particular embodiments, the aromatic dimethacrylate is

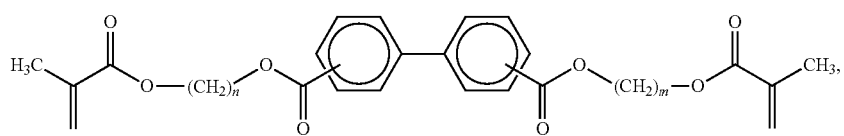
(Formula II)

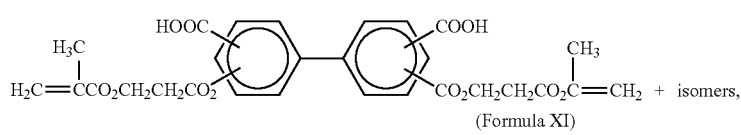
(Formula III)

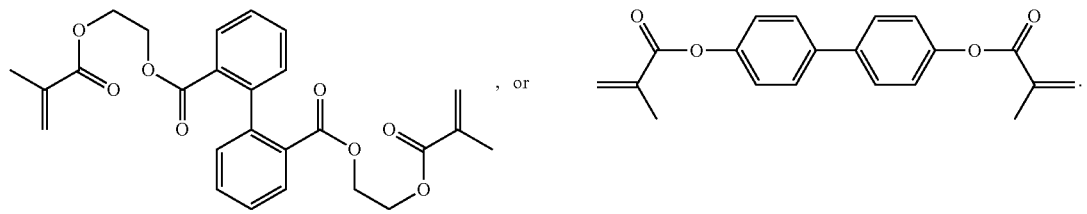
(Formula XI) , or (Formula XII)

In some embodiments, the compound of Formula II is:

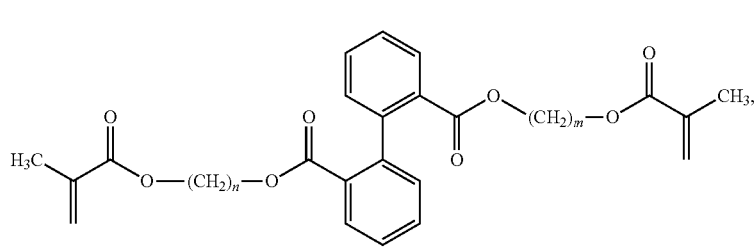
(Formula XIII)

wherein n and m are each independently 2-10. In some embodiments, n and m are each independently 2, 3, 4, 5, or 6. I particular embodiments, at least one of n and m is 2. In more particular embodiments, both n and m are 2. For example, the aromatic dimethacrylate is

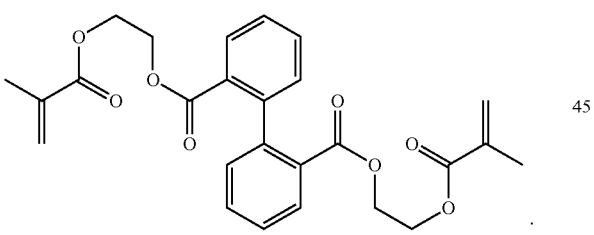

In some embodiments, the monomer is

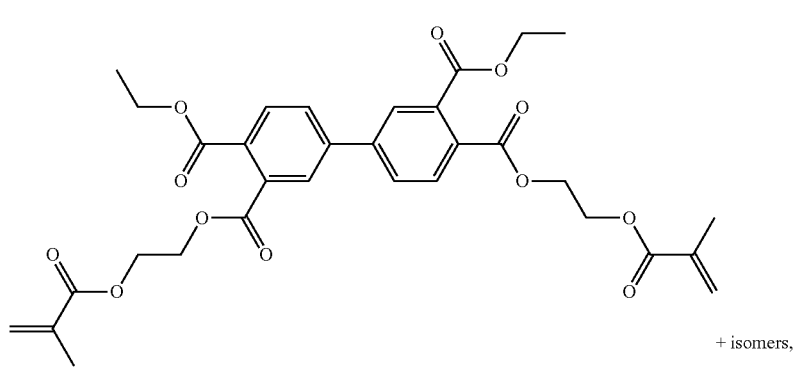
(Formula XIV)

+ isomers,

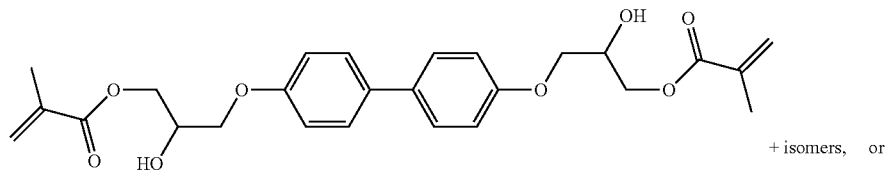

(Formula XV)

+ isomers, or

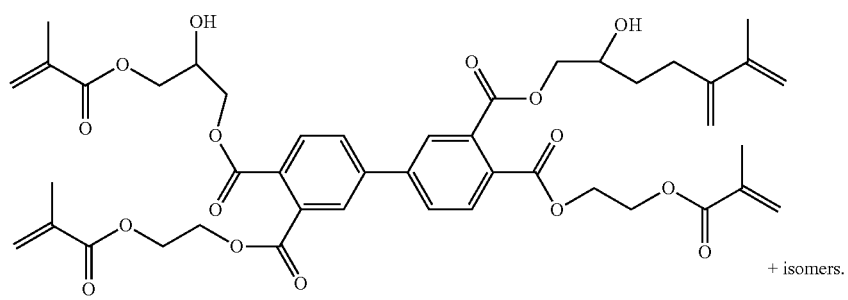

(Formula XVI)

+ isomers.

In particular embodiments, the composition comprises a dimethacrylate that is a biphenyldimethacrylate, bisphenyldimethacrylate, biphenol-dimethacrylate, bisphenol-dimethacrylate, or a compound of any of Formulas I-XV. Such dimethacrylates can be referred to interchangeably herein as "BDPM". In some embodiments, BDPM is a compound of any of Formulas II, III, or XI-XV. BDPM can be any compound that comprises a biphenyl or biphenol group and two methacrylate groups. In some embodiments, the BDPM is a compound of Formula III, XII, or both.

The dimethacrylate can, upon formulation, account for 0.01-50% of an disclosure composition by wt/wt or wt/vol. The dimethacrylate can account for 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% of the composition upon formulation. The dimethacrylate can account for 0.01-0.5%, 0.1-2%, 1-5%, 5-10%, 10-15%, 15-20%, 20-25%, 25-30%, 30-35%, 35-40%, 40-45%, or 45-50% of the composition upon formulation.

Casting compositions can comprise a monomer that is not a dimethacrylate. A casting composition can comprise a dimethacrylate and an additional monomer that is not a dimethacrylate. The monomer that is not a dimethacrylate can be an acrylate or a monomethacrylate. The acrylate can be, e.g., dipentaerythritol pentacrylate phosphate. In some cases, the monomethacrylate comprises a tertiary amine. In some cases, the monomethacrylate is methyl methacrylate, hydroxyethyl methacrylate (HEMA), N-tolylglycine-glycidylmethacrylate (NTG-GMA, including the carboxylic acid form or salts thereof for example sodium, potassiu, calcium, magnesium salts). NTG-GMA salts include, by way of example only, Na-NTG-GMA, K-NTG-GMA, Ca-di-NTG-GMA, Mg-di-NTG-GMA, HOMg-monoNTG-GMA). In some embodiments, the composition does not further comprise an acrylate or monomethacrylate.

In particular embodiments, the acrylate or monomethacrylate is N-tolylglycine-glycidylmethacrylate (NTG-GMA), or a carboxylic acid form or salt thereof. For example, in some cases the monomethacrylate is

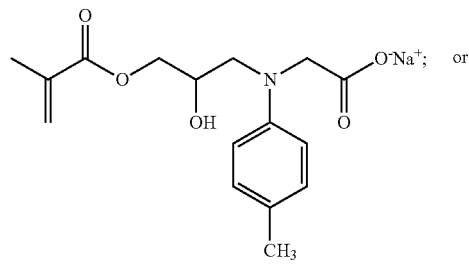

NTG-GMA-sodium salt/n-tolyglycine glycidylmethacrylate

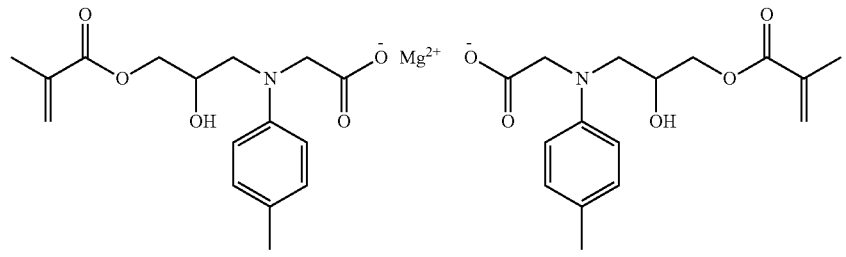

NTG-GMA-magnesium salt

In some embodiments, the acrylate or monomethacrylate is methyl methacrylate. The methyl methacrylate can have the following structure:

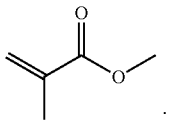

The acrylate or monomethacrylate can account for 0%, 0.1-25%, 0.2-10%, 0.5-2%, 1-5%, or 2-10% of the composition upon formulation. The acrylate or monomethacrylate can, upon formulation account for 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% of the composition upon formulation.

In particular examples, the acrylate or monomethacrylate is N-tolylglycine-glycidylmethacrylate (NTG-GMA), N-phenylglycine-glycidylmethacrylate (NPG-GMA) or a carboxylic acid form or salt thereof and the aromatic dimethacrylate of Formula II, for example biphenyldimethacrylate (BPDM).

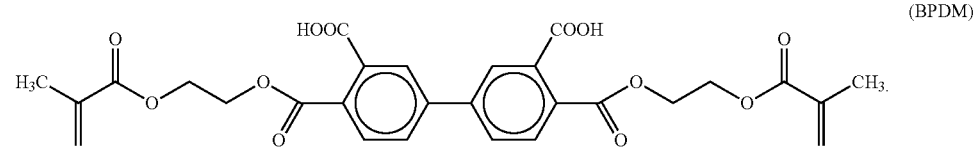

In further examples, the coating formulations comprise an unsaturated alcohol and a cyclic acid dianhydride. The dianhydride which may be used in the coating formulation of the invention may have the general Formula XVII:

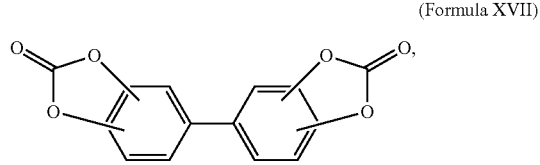

(Formula XVII)

wherein X is O, SO$_2$ or CO and p is 0 or 1.

In some embodiments the dianhydride may be

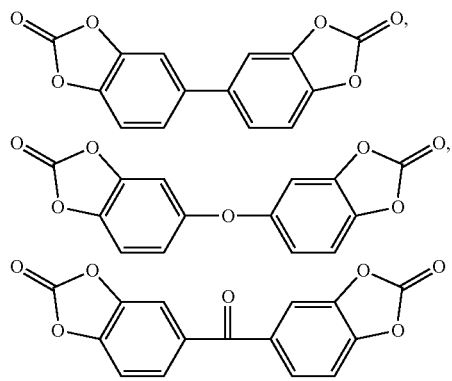

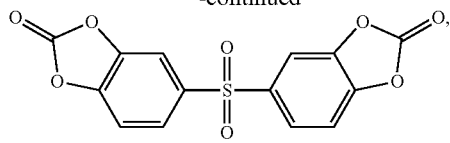

or the isomers thereof.

The unsaturated alcohol that may be used in the coating formulations of the instant application may have the general Formula XVIII:

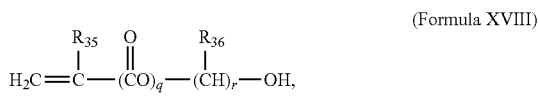

(Formula XVIII)

wherein $R_{35}$ is H or $CH_3$, $R_{36}$ is H, $CH_3$, or $=CH_2$, q is 0 or 1, and r is 1, 2, 3, or 4. For example, the alcohol is hydroxy-ethyl methacrylate ($CH_2=C(CH_3)COOCH_2CH_2OH$). The composition may further comprise the reaction product of N-tolylglycine or N-phenylglycine with glycidyl methacrylate.

Solvents

A wide range of solvents may be used in the coating compositions and methods of the instant disclosure. The solvent may be chosen such that composition is soluble in the solvent. Non limiting examples of the solvents that may be used in the methods and compositions disclosed herein include acetone, water, acetone and water, alcohol (such as, e.g., methanol, ethanol, isopropyl alcohol, butyl alcohol, amyl alcohol, cetyl alcohol, polyhydric alcohols such as ethylene glycol, propylene glycol, glycerol, erythritol, xylitol, mannitol, volemitol, allyl alcohol, geraniol, propargyl alcohol, inositol, menthol, among others), alcohol and water, acetone and alcohol, acetone and alcohol and water, methylene chloride, trichloromethane, carbon tetrachloride, tetrahydrofuran, acetonitrile benzene, benzene, halogenated benzenes (such as, e.g., chlorobenzene, dichlorobenzene (such as, e.g., o-dichlorobenzene, m-dichlorobenzene), bromobenzene (such as, e.g., o-dibromobenzene, m-dibromobenzene), additionally any mix of halogen groups may be substituted), toluene, hexane, hexane(s), xylene, ethyl acetate, and mixtures thereof (e.g., acetone and alcohol and water). In particular embodiments, the solvent comprises acetone, ethanol, water, dichlorobenzene, or any combination thereof. In some embodiments, the solvent is acetone, water, or a combination thereof. In some cases, the solvent comprises dichloromethane. In some cases, the solvent comprises benzene. In some cases, the solvent comprises dichlorobenzene. In some cases the solvent comprises methanol. In some cases the solvent is ethanol. In some cases the solvent is acetone. In some cases the solvent is a mixture of acetone and ethanol.

The solvent can be present in an amount that is at least 50-99.9% by wt/wt or wt/vol of the composition upon formulation. For example, the solvent can account for 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%, of the composition upon formulation. The solvent can account for 50-70%, 60-80%, 75-90%, 85-95%, or 90-99.9% of the composition upon formulation.

Polymerization Initiators

The composition can in some cases further comprise a polymerization initiator. The polymerization initiator can be, e.g., a photoinitiator, a chemical initiator, a thermal initiator, or other polymerization initiator. The polymerization initiator can be present in an amount sufficient to reduce the time required to form the polymerization product (as compared to the rate of polymerization in the absence thereof). In some cases, the amount of polymerization initiator accounts for 0.01-6% of the composition upon formulation. The amount of polymerization initiator can account for 0.05%, 0.1%, 0.2%, 0.3%, 0.4%, 0.5%, 0.6%, 0.7%, 0.8%, 0.9%, 1%, 1.5%, 2%, 3%, 4%, 5%, or 6% of the composition upon formulation. In some embodiments, the polymerization initiator accounts for 0.05-0.2% of the composition upon formulation, for 0.1-0.7% of the composition upon formulation, for 0.5-1%, or for 1-6% of the composition upon formulation. It is understood by those of skill in the art that the amount of polymerization initiator used in the composition will vary depending upon the type of polymerization initiator used, volatility of the one or more solvents used, and the conditions under which the composition is applied to a substrate.

In some cases, the polymerization initiator is a chemical initiator. Exemplary chemical initiators include free radical initiators, e.g., peroxides, azo-initiators, and C-C initiators.

In some cases, the polymerization initiator is a photoinitiator. Photoinitiators can include any compounds which release free radicals when exposed to light. Photoinitiators can comprise chemical bonds that are cleavable by photolysis. The photoinitiator can be a Type I or Type II photoinitiator. Type I photoinitiators can undergo a unimolecular bond cleavage upon exposure to light to yield free radicals. Type II photoinitiators can undergo a bimolecular reaction wherein an excited state of the photoinitiator interacts with a second molecule (e.g., a co-initiator) to generate free radicals. In some embodiments said second molecule may serve multiple functions (e.g., a co-initiator and a monomer such as NTG-GMA). The photoinitiators can be induced by electromagnetic radiation such as light and ultraviolet energy. Exemplary photoinitiators include, e.g., benzoin ethers, benzyl ketals, α-Dialkoxy-aceto-phenones, α-hydroxyl-alkyl-phenones, α-amino-alkyl-phenones, acylphosphine oxides, benzo-phonenes/amines, thio-xanthones/amines, hydroxy-acetophenones, alkylamino-acetophenones, alpha-haloacetophenones, titanocenes, and other specialty molecules. Photoinitiators suitable in the compositions of the disclosure include, by way of non-limiting example, Acetophenone, Anisoin, Anthraquinone, Anthraquinone-2-sulfonic acid, sodium salt monohydrate, (Benzene) tricarbonylchromium, Benzil, Benzoin, sublimed, Benzoin ethyl ether, Benzoin isobutyl ether, tech., Benzoin methyl ether, Benzophenone, Benzophenone/1-Hydroxycyclohexyl phenyl ketone, 50/50 blend, 3,3',4,4'-Benzophenonetetracarboxylic dianhydride, sublimed, 4-Benzoylbiphenyl, 2-Benzyl-2-(dimethylamino)-4'-morpholinobutyrophenone, 4,4'-Bis(diethylamino) benzophenone, 4,4'-Bis(dimethylamino)benzophenone, Camphorquinone, 2-Chlorothioxanthen-9-one, (Cumene) cyclopentadienyliron(II) hexafluorophosphate, Dibenzosuberenone, 2,2-Diethoxyacetophenone, 4,4'-Dihydroxybenzophenone, Cat. No. Photoinitiator, 2,2-Dimethoxy-2-phenylacetophenone, 4-(Dimethylamino)benzophenone, 4,4'-Dimethylbenzil, 2,5-Dimethylbenzophenone, tech., 3,4-Dimethylbenzophenone, Diphenyl(2,4,6-trimethylbenzoyl) phosphine oxide/2-Hydroxy-2-methylpropiophenone, 50/50 blend, 4'-Ethoxyacetophenone, 2-Ethylanthraquinone, Ferrocene, 3'-Hydroxyacetophenone, 4'-Hydroxyacetophenone, 3-Hydroxybenzophenone, 4-Hydroxybenzophenone, 1-Hydroxycyclohexyl phenyl ketone, 2-Hydroxy-2-methylpropiophenone, 2-Methylbenzophenone, 3-Methylbenzophenone, Methybenzoylformate, 2-Methyl-4'-(methylthio)-2-morpholinopropiophenone, Phenanthrenequinone, 4'-Phenoxyacetophenone, Thioxanthen-9-one, Triarylsulfonium hexafluoroantimonate salts (mixed), Triarylsulfonium hexafluorophosphate salts (mixed).

In some examples, the photoinitiator may be a α-hydroxyketone, for example 1-hydroxy-cyclohexyl-phenyl-ketone (Irgacure® 184), Irgacure® 500 (Irgacure® 184 (50 wt %), benzophenone (50 wt %)), Darocur® 1173 (2-hydroxy-2-methyl-1-phenyl-1-propanone), or Irgacure® 2959 (2-hydroxy-1-[4-(2-hydroxyethoxy)phenyl]-2-methyl-1-propanone). In some examples, the photoinitiator may be a phenylglyoxylate, for example Darocur® MBF (methylbenzoylformate) or Irgacure® 754 (oxy-phenyl-acetic acid 2-[2-oxo-2 phenyl-acetoxy-ethoxy]ethyl ester and oxy-phenyl-acetic 2-[2-hydroxy-ethoxy]-ethyl ester. The photoinitiator may also be a benzyldimethyl-ketal, for example Irgacure® 651. In some cases, the photoinitiator may be a α-aminoketone for example Irgacure® 369 (2-benzyl-2(dimethylamino)-1-[4-(4-morpholinyl)phenyl]-1-butanone, or Irgacure® 1300 (Irgacure® 369 (30 wt %)+Irgacure® 651 (70 wt %)). The photoinitiator may be a mono acyl phosphine (MAPO), for example Darocur® TPO (diphenyl(2,4,6-trimethylbenzoyl)-phosphine oxide). Photoinitiator may also be a MAPO/α-hydroxyketone, for example Darocur® 4265 (Darocur® TPO (50 wt %) Darocur® 1173 (50 wt %)). Initiator may be bis acyl phosphine (BAPO, for example Irgacure® 819 (phosphine oxide, phenyl bis (2,4,6-trimethyl benzoyl)). Photoinitiator may also be a BAPO dispersion, for example Irgacure® 819DW (Irgacure® 819 (45% active) dispersed in water). The photoinitiator may also be BAPO/α-hydroxyketone, for example Irgacure® 2022 (Irgacure® 819 (20 wt %) Darocur® 1173 (80 wt %)). The photoinitiator may also be a phosphine oxide, for example Irgacure® 2100. The photoinitiator may be a metallocene, for example Irgacure® 784 (Bis(eta 5-2,4-cyclopentadien-1-yl)Bis[2,6-difluoro-3-(1H-pyrrol-1-yl)phenyl]titanium). The photoinitiator may also be a iodonium salt, for example Irgacure® 250 (iodonium, (4-methylphenyl) [4-(2-methylpropyl)phenyl]-, hexafluorophosphate(1-).

The photoinitiator can also be a cationic photoinitiator. Cationic photoinitiators can produce a Brönsted or Lewis acid, and can initiate polymerization of cationically polymerizing materials (e.g., epoxies) or resins capable of undergoing crosslinking via polycondensation reactions.

The photoinitiator can be activatable by light having wavelengths in the UV range. The photoinitiator can be activated by light having wavelengths in the UV-A range (e.g., 320-400 nm). The photoinitiator can be activated by light having wavelengths in the UV-B range (e.g., 280-320 nm). The photoinitiator can be activated by light having wavelengths in the UV-C range (e.g., 200-280 nm). The photoinitiator can be activated by light having visible and/or infrared wavelengths. The photoinitiator can be an acetone soluble photoinitiator. Exemplary acetone soluble photoinitiators include Irgacure® 2959; Lucirin® TPO (2,4,6-Trimethylbenzoyldiphenylphosphine oxide); Lucirin® TPO-L (Ethyl-2,4,6-Trimethylbenzoylphenylphosphinate); camphorquinone, and Lucirin® BAPO (Phenyl-bis(2,4,6-trimethylbenzoyl)phosphine oxide). The acetone soluble photoinitiator can be activated in the presence of light having wavelengths above, e.g., 325 nm. Such acetone soluble photoinitiators include those already described herein. A skilled artisan will understand that the compositions of the disclosure can comprise any combination of polymerization initiators. In some embodiments, the polymerization initiator is camphorquinone. In some embodiments, the camphorquinone accounts for 0.1-3% wt/wt or wt/vol of the composition upon formulation. In particular embodiments, the camphorquinone accounts for 0.1% by wt/vol or vol/vol of the composition upon formulation. In some cases, the photoinitiator is 2-hydroxy-1-[4-(2-hydroxyethoxy)phenyl]-2-methyl-1-propanone (Igracure 2959), phenylbis(2,4,6-trimethylbenzoyl)phosphine oxide (PTPO, Lucirin® BAPO), or diphenyl(2,4,6-trimethylbenzoyl)phosphine oxide. In particular cases, the photoinitiator is 2-hydroxy-1-[4-(2-hydroxyethoxy)phenyl]-2-methyl-1-propanone. In some embodiments, the photoinitiator is not phenylbis(2,4,6-trimethylbenzoyl)phosphine oxide (PTPO, Lucirin® BAPO).

Therapeutic Agents

The compositions as described herein may also comprise therapeutic agents. The therapeutic agent can be present in solution or suspension or as a solid. The therapeutic agent can be dissolved in one or more volatile solvents. Hence, the therapeutic agent may be at least partially soluble in the one or more volatile solvents described above. Exemplary therapeutic agents include, without limitation, antiplatelets, anti-inflammatory agents, antimicrobial agents, antibacterial agents, antifungal agents, anti-thrombogenic agents, anti-thrombotic agents, anti-proliferative agents, anti-adhesion agents, cytostatic agents, vasodilators, alkylating agents, antimitotics, anti-secretory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, protein receptor agonists or antagonists, anti-stenosis agents, isolates, enzymes, monoclonal antibodies, ribonucleases, nutraceutical agents (e.g. vitamins, minerals, etc.), labeling agents and mixtures thereof. The therapeutic agent can be a bio-active agents, e.g. a small molecule, a non-replicating viruses, a miRNA or other bio-active agents.

Illustrative antiplatelets include irreversible cyclooxygenase inhibitors (e.g., aspirin), adenosine diphosphate (ADP) receptor inhibitors (e.g. clopidogrel (plavix), prasugrel (effient), ticagrelor (brilinta), elinogrel, and ticlopidine (ticlid)), phosphodiesterase inhibitors (e.g. cilostazol (pletal), glycoprotein IIB/IIIA inhibitors (e.g. abciximab (ReoPro), eptifibatide (integrilin), tirofiban (aggrastat)), Adenosine reuptake inhibitors (e.g. dipyridamole (persantine), thromboxane inhibitors (e.g. thromboxane synthase inhibitors, thromboxane receptor antagonists, Terutroban, and mixtures thereof.

Illustrative anti-inflammatory agents include classic non-steroidal anti-inflammatory drugs (NSAIDS), such as aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone (relafen), acetaminophen, and mixtures thereof; COX-2 inhibitors, such as nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof; glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, and mixtures thereof; the anti-inflammatory agent rapamycin; and mixtures thereof. Anti-inflammatory agents also include steroids. Exemplary steroids include glucocorticoids, corticosteroids and mineralocorticoids. For example hydrocortisone, hydrocortisone acetate, cortisone acetate, tixocortol pivalate, prednisolone, methylprednisolone, prednisone, meprednisone, triamcinolone, paramethasone, fluprednisolone, betamethasone, dexamethasone, fludrocortisone, desoxycorticosterone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone sodium phosphate, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate, hydrocortisone-17-butyrate, hydrocortisone-17-aceponate, hydrocortisone-17-buteprate, and prednicarbate. Anti-inflammatory agents also include Immune Selective Anti-Inflammatory Derivatives (ImSAIDs). Illustrative anti-inflammatory agents also include COX-2 inhibitors, such as nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof; glucocorticoids, such as and mixtures thereof; the anti-inflammatory agent rapamycin; and mixtures thereof.

Antimicrotubule agents such as paclictaxel and docetaxel inhibit mitosis and, hence, cellular proliferation. Antiproliferative agents such as cyclophosphamide, mithromycin, and actinomycin-D prevent proliferation of smooth muscle cells. Sirolimus (rapamycin), temsirolimus, zotarolimus, tacrolimus, pimecrolimus, everolimus, cyclosporine A, dexamethasone and methyl prednisolone are immunosuppressive agents that have been also shown to prevent or retard neointimal hyperplasia.

Illustrative anti-fungal agents include polyene antifungals, such as amphotericin B, candicidin, filipin, hamycin, natamycin, nystatin, rimocidin. Antifungals may be imidaxole, triazole and thiazole antifungals. Imidazole antifungal agents include bifonazole, butoconazole, blotrimazole, econazole, fenticonazole, isoconazole, ketoconazole, miconazole, omoconazole, oxiconazole, sertaconazole, sulconazole and tioconazole. Triazole based antifungal agents include albaconazole, fluconazole, isavuconazole, itraconazole, posaconazole, ravuconazole, terconazole and voriconazole. Thiazole antifungal agents include abafungin. Allylamine antifungal agents may also be used in the protective coating of the disclosure. Non-limiting examples of allylamine antifungal agents include amorolfin, butenafine, naftifine and terbinafine. The polymeric composition may also employ echinocandins fungal agents for examples the protective coatings may comprise anidulafungin, caspofungin and micafungin. Other antifungal agents that may be used with the polymeric composition of the present disclosure include benzoic acid, ciclopirox, flucytosine or 5-fluorocytosine, griseofulvin, haloprogin, polygodial, crystal violet, tolnaftate and undecylenic acid essential oils possessing antifungal properties may also be used in the polymeric composition of the current disclosure. Non-limiting examples of such essential oils include oregano, allicin, citronella oil, coconut oil, lugol's iodine, lemon myrtle, neem seed oil, olive leaf, orange oil, palmarosa oil, patchouli, selenium, and tea tree oil.

Anti-viral agents that may be used in the polymeric compositions of the current disclosure include aciclovir, amantadine, antiviral proteins, alovudine, arbidol, brivudine, 5-bromouridine, cidofovir, daclatasvir, template:DNA antivirals, docosanol, double-stranded RNA (ds RNA) activated caspase oligomerizer (DRACO), famciclovir, FGI-104, fialuridine, fomivirsen, foscarnet, FV-100, ganciclovir, ibacitabine, idoxuridine, imiquimod, inosine, inosine pranobex, interferon, interferon alfa-2b, interferon alfacon-1, interferon alpha-n3, interferon type I, interferon type II, interferon type III, interferon-gamma, maribavir, methisazone, moroxydine, nucleoside analogue, oragen, peginterferon alfa-2a, pegylated interferon, penciclovir, pleconaril, podophyllotoxin, prosetta, PSI-6130, reciGen, resiquimod, ribavirin, rintatolimod, template:RNA antivirals, semapimod, setrobuvir, simeprevir, sofosbuvir, sorivudine, teco-virimat, taribavirin, telbivudine, tenofovir alafenamide fumarate, theaflavin, tilorone, trifluridine, tromantadine, valaciclovir, valganciclovir and vidarabine.

Antiseptics could also be used as therapeutic agents with the polymeric composition of the present disclosure. Some common antiseptics that may be use include alcohols (like ethanol, 1-propanol, 2-propanol), quaternary ammonium salts also known as quats or QAC's (For example benzalkonium chloride (BAC), cetyl trimethylammonium bromide (CTMB), cetylpyridinium chloride (Cetrim, CPC) and benzethonium chloride (BZT)), boric acid, brilliant green, chlorhexidine gluconate, hydrogen peroxide, iodine (for example providone-iodine and Lugol's iodine), mercurochrome, manuka money, octenidine dihydrochloride, phenol (carbolic acid) compounds, polyhexanide (polyhexamethylene biguanide, PHMB), sodium chloride, sodium hyposhlorite, calcium hypochlorite and sodium bicarbonate.

Exemplary antithrombins include, e.g., heparin, aspirin, hirudin, dabigatran, Enoxaparin, anti-Xa, anti-XIIa, anti-IXa agents, GPIIb/IIIa receptor inhibitor as tirofiban, eptifibatide, cilostazol, plavix, Ticlid, urokinase, and PPack (dextrophenylalanine proline arginine chloromethylketone. Suitable anti-cancer agents include methotrexate, purine, pyridine, and botanical (e.g. paclitaxel, colchicines and triptolide), epothilone, antibiotics, and antibodies.

Anti-adhesion agents can include any agent that blocks and/or inhibits an adhesion molecule such as, e.g., cell adhesion molecules (CAM), intercellular adhesion molecules (ICAM), vascular cell adhesion molecules (VCAM), and others. Agents that block such adhesion molecules can include for example antibodies, RNAi agents. Exemplary anti-adhesion agents include, by way of example only, ocriplasmin.

Cytostatic agents (e.g., alkylating agents and other agents) are described herein. Exemplary vasodilators include, e.g., Hydralazine, Minoxidil. Exemplary antimicrobials include, e.g., chlorhexidine diacetate, silver carbonate, and antimicrobial peptides (AMPs).

Exemplary immunosuppressive agents include, e.g., Azathioprine, cyclosporine, interferon, opioids, TNF-binding proteins, infliximab (Remicade), etanercept (Enbrel), or adalimumab, Mycophenolic acid, Fingolimod, Myriocin.

Exemplary antibiotics include, e.g., amoxicillin, ampicillin, aminoglycosides such as gentamycin or neomycin, azithromycin, aztreonam, aclarubicin, actinomycin D, actinoplanone, adriamycin, aeroplysinin derivative, amrubicin, anthracycline, azinomycin-A, bisucaberin, bleomycin sulfate, bryostatin-1, cefepime, cefixime, ceftriaxone, cephalosporin C, cephazolin, cephamandol, chloramphenicol, ciprofloxacin, clindamycin, calichemycin, chromoximycin, dactinomycin, daunorubicin, ditrisarubicin B, doxorubicin, doxorubicin-fibrinogen, doxycycline, erythromycin, imipenem, meropenem, metronidazole, minocycline, minocycline hydrochloride, minocycline hyclate, netilmycin, rifampicin, rifamycins, spectinomycin, penicillins such as oxacillin or mezlocillin, streptomycin, tetracycline, tobramycin, trimethoprim, TYGACIL® (tigecycline; Wyeth, Madison, N.J), elsamicin-A, epirubicin, erbstatin, esorubicin, esperamicin-Al, esperamicin-Alb, fostriecin, glidobactin, gregatin-A, grincamycin, herbimycin, idarubicin, illudins, kazusamycin, kesarirhodins, menogaril, mitomycin, neoenactin, oxalysine, oxaunomycin, peplomycin, pilatin, pirarubicin, porothramycin, pyrindanycin A, rapamycin (e.g., sirolimus), rapamycin derivatives or analogs such as temsirolimus, umirolimus, zotarolimus, everolimus, deforolimus, rhizoxin, rodorubicin, sibanomicin, siwenimycin, sorangicin-A, sparsomycin, talisomycin, terpentecin, thrazine, tricrozarin A, and zorubicin.

Anti-infective agents useful in the disclosure include, e.g., pyrimidine analogs. A "pyrimidine analog", as used herein, generally refers to a compound with a pyrimidine ring structure (1,3-diazine) substituted with one or more atoms or chemical groups or oxidized at one or more carbons in the pyrimidine ring structure.

In certain embodiments, the pyrimidine analog contains a halogen substituent, such as F, Cl, Br, or I, at a carbon in the pyrimidine ring structure. In certain embodiments, the pyrimidine analog contains at least one F substituent at a carbon of its pyrimidine ring structure and is referred to as a "fluoropyrimidine." Exemplary fluoropyrimidines include, but are not limited to, 5-FU, 5-FUdR (5-fluoro-deoxyuridine; floxuridine), fluorouridine triphosphate (5-FUTP), fluorodeoxyuridine monophosphate (5-dFUMP), 5-fluorocytosine, 5-fluorothymidine, capecitabine, trifluridine, and trifluorothymidine. Other halogenated pyrimidine analogs include, but are not limited to, 5-bromodeoxyuridine (5-BudR), 5-bromouracil, 5-chlorodeoxyuridine, 5-chlorouracil, 5-iododeoxyuridine (5-IudR), 5-iodouracil, 5-bromocytosine, 5-chlorocytosine, and 5-iodocytosine.

In certain embodiments, the pyrimidine analog is a uracil analog. A "uracil analog" refers to a compound that contains a uracil ring structure substituted with one or more atoms or chemical groups. In certain embodiments, the uracil analog contains a halogen substituent, such as F, Cl, Br, or I. In certain embodiments, the uracil analog contains an F substituent, and is referred to as a "fluorouracil analog." Exemplary fluorouracil analogs include, but are not limited to, 5-FU, carmofur, doxifluridine, emitefur, tegafur, and floxuridine.

Other anti-infectives which may be useful in the disclosure include, e.g., chlorhexidine, silver compounds, silver ions, silver particles, or other metallic compounds, ions or particles (such as gold).

Chemotherapeutic agents may also serve as anti-infective agents. Exemplary classes of chemotherapeutics useful in combination with pyrimidine analogs are uracil analogs, anthracyclins, folic acid antagonists, podophyllotoxins, camptothecins, hydroxyureas, and platinum complexes.

Exemplary anthracyclines include but are not limited to doxorubicin, daunorubicin, idarubicin, epirubicin, pirarubicin, zorubicin, and carubicin. Other suitable anthracyclines are anthramycin, mitoxantrone, menogaril, nogalamycin, aclacinomycin A, olivomycin A, chromomycin A3, and plicamycin.

Exemplary folic acid antagonists include but are not limited to methotrexate or derivatives or analogs thereof, such as edatrexate, trimetrexate, raltitrexed, piritrexim, denopterin, tomudex, and pteropterin.

Exemplary platinum complexes are described in U.S. Pat. Nos. 5,409,915 and 5,380,897, hereby incorporated by reference. Platinum complexes such as cisplatin, carboplatin, oxaliplatin, and miboplatin are contemplated in the present disclosure.

Other anti-infective agents include, e.g., silver compounds (e.g., silver chloride, silver nitrate, silver oxide), silver ions, silver particles, gold compounds (such as gold chloride, auranofin), gold ions, gold particles, iodine, povidone/iodine, chlorhexidine, 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefinenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clomocycline, colistin, cyclacillin, dapsone, demeclocycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycins, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, vancomycin, azaserine, candicidin(s), chlorphenesin, dermostatin(s), filipin, fungichromin, mepartricin, nystatin, oligomycin(s), ciproflaxacin, norfloxacin, ofloxacin, pefloxacin, enoxacin, rosoxacin, amifloxacin, flerofloxacin, temafloaxcin, lomefloxacin, perimycin A or tubercidin, and the like.

Exemplary anti-proliferative (e.g., anti-neoplastic) agents include, but are not limited to tubulin interacting agents, topoisomerase inhibitors and agents, acitretin, alstonine, amonafide, amphethinile, amsacrine, ankinomycin, antineoplaston, aphidicolin glycinate, asparaginase, angiopeptin, acetylsalicylic acid, baccharin, batracylin, benfluoron, benzotript, bromofosfamide, caracemide, carmethizole hydrochloride, chlorsulfaquinoxalone, clanfenur, claviridenone, crisnatol, curaderm, cytarabine, cytocytin, dacarbazine, datelliptinium, dihaematoporphyrin ether, dihydrolenperone, dinaline, distamycin, docetaxel, elliprabin, elliptinium acetate, enoxaprin, epothilones, ergotamine, etoposide, etretinate, fenretinide, gallium nitrate, genkwadaphnin, hexadecylphosphocholine, hirudin, HDAC inhibitors, homoharringtonine, hydroxyurea, ilmofosine, isoglutamine, isotretinoin, leukoregulin, lonidamine, merbarone, merocyanlne derivatives, methylanilinoacridine, minactivin, mitonafide, mitoquidone, mitoxantrone, mopidamol, motretinide, N-(retinoyl)amino acids, N-acylated-dehydroalanines, nafazatrom, nocodazole derivative, octreotide, oquizanocine, paclitaxel, pancratistatin, pazelliptine, piroxantrone, polyhaematoporphyrin, polypreic acid, probimane, procarbazine, proglumide, razoxane, retelliptine, spatol, spirocyclopropane derivatives, spirogermanium, strypoldinone, superoxide dismutase, teniposide, thaliblastine, tocotrienol, topotecan, ukrain, vinblastine sulfate, vincristine, vindesine, vinestramide, vinorelbine, vintriptol, vinzolidine, withanolides, and monoclonal antibodies capable of blocking smooth muscle cell proliferation.

Exemplary antimetabolite agents include, e.g., 5-FU-fibrinogen, acanthifolic acid, aminothiadiazole, brequinar sodium, carmofur, cyclopentyl cytosine, cytarabine phosphate stearate, cytarabine conjugates, dezaguanine, dideoxycytidine, dideoxyguanosine, didox, doxifluridine, fazarabine, floxuridine, fludarabine phosphate, 5-fluorouracil, N-(2'-furanidyl)-5-fluorouracil, inhibitors of essential amino acids, isopropyl pyrrolizine, methobenzaprim, methotrexate, norspermidine, ornithine decarboxylantion inhibitors, pentostatin, piritrexim, plicamycin, thioguanine, tiazofurin, trimetrexate, tyrosine kinase inhibitors, and uricytin.

Exemplary alkylating agents include, e.g., aldo-phosphamide analogues, altretamine, anaxirone, bestrabucil, budotitane, carboplatin, carmustine, chlorambucil, cisplatin, cyclophosphamide, cyplatate, diphenylspiromustine, diplatinum cytostatic, elmustine, estramustine phosphate sodium, fotemustine, hepsul-fam, ifosfamide, iproplatin, lomustine, mafosfamide, mitolactol, oxaliplatin, prednimustine, ranimustine, semustine, spiromustine, tauromustine, temozolomide, teroxirone, tetraplatin and trimelamol.

Non-limiting examples of monoclonal antibodies include rituximab, trastuzumab, gemtuzumab, ozogamicin, alemtuzumab, ibritumomab, tiuxetan, tositumomab, cetuximab, bevacizumab, panitumumab, and ofatumumab.

Exemplary anesthetic agents include, e.g., procaine, amethocaine, cocaine, lidocaine (also known as Lignocaine), prilocaine, bupivacaine, levobupivacaine, ropivacaine, mepivacaine, dibucaine, Barbiturates, Amobarbital, Methohexital, Thiamylal, Thiopental, Benzodiazepines, Diazepam, Lorazepam, Midazolam, Etomidate, Ketamine, Propofol, Alfentanil, Fentanyl, Remifentanil, Sufentanil, Buprenorphine, Butorphanol, diacetyl morphine, Hydromorphone, Levorphanol, Meperidine, Methadone, Morphine, Nalbuphine, Oxycodone, Oxymorphone, Pentazocine, and mixtures thereof.

Other suitable therapeutic agents include, e.g., Methotrexate, Azathioprine, vincristine, VinBlastine, Fluorouracil, Adriamycin, and Mutamycin. The therapeutic agent can be an anticoagulant. Exemplary anticoagulant drugs include Heparin, Coumadin, Protamine, and Hirudin.

The polymeric compositions of the disclosure may also be formulated to include one or more disinfectants. Non-limiting examples of the disinfectants that may be used in the polymeric composition of the present disclosure include alcohols (like ethanol and propanol), aldehydes (such as formaldehyde, ortho-phthalaldehyde and glutataldehyde), oxidizing agents (for example Sodium hypochlorite, calcium hypochlorite, chloramine, chloramine-T, chlorine dioxide, hydrogen peroxide, hydrogen peroxide vapor, iodine, peracetic acid, performic acid, potassium permanganate, potassium peroxymonosulfate), phenolics (for example phenol, o-Phenylphenol, chloroxylenol, hexachlorophene, thymol, amylmetacresol, and 2,4-dichlorobenzyl alcohol), Quats (such as benzalkonium chloride), silver, lactic acid, and sodium bicarbonate.

The compositions described herein can comprise one or more odorants. An odorant can be any chemical entity having an odor. The chemical can be sufficiently volatile to enable contact with an olfactory system of a subject. Odorants can be found in, e.g., food, wine, spices, perfumes, essential oils, fragrance oils, substances that are secreted from an animal, plants, and other species. The odorant can, for example, be found in substances (e.g., urine) secreted from a predator. The odorant can be found in, without limitation, coyote urine, fox urine, bobcat urine, raccoon urine, mountain lion urine, cougar urine, panther urine, wolf urine, bear urine, whitetail deer urine, whitetail doe in heat urine, whitetail buck in rut urine, and/or moose urine.

The therapeutic agent can be a gene therapy formulation, such as, e.g., Keratin 8, VEGF, and EGF, PTEN, Pro-UK, NOS, or C-myc.

The coating compositions described herein can comprise a plurality of therapeutic agents. It is understood that any combination of the therapeutic agents described herein are contemplated in the disclosure.

A therapeutic agent and/or odorant may be present in the coating composition at a concentration of 1 pg/mL, 5 pg/mL, 10 pg/mL, 20 pg/mL, 30 pg/mL, 40 pg/mL, 50 pg/mL, 60 pg/mL, 70 pg/mL, 80 pg/mL, 90 pg/mL, 100 pg/mL, 200 pg/mL, 300 pg/mL, 400 pg/mL, 500 pg/mL, 600 pg/mL, 700 pg/mL, 800 pg/mL, 900 pg/mL, 1000 pg/mL (1 ng/mL), 5 ng/mL, 10 ng/mL, 20 ng/mL, 30 ng/mL, 40 ng/mL, 50 ng/mL, 60 ng/mL, 70 ng/mL, 80 ng/mL, 90 ng/mL, 100 ng/mL, 200 ng/mL, 300 ng/mL, 400 ng/mL, 500 ng/mL, 600 ng/mL, 700 ng/mL, 800 ng/mL, 900 ng/mL, 1000 ng/mL (1 µg/mL), 5 µg/mL, 10 µg/mL, 20 µg/mL, 30 µg/mL, 40 µg/mL, 50 µg/mL, 60 µg/mL, 70 µg/mL, 80 µg/mL, 90 µg/mL, 100 µg/mL, 200 µg/mL, 300 µg/mL, 400 µg/mL, 500 µg/mL, 600 µg/mL, 700 µg/mL, 800 µg/mL, 900 µg/mL, 1000 µg/mL (1 mg/mL), 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 200 mg/mL, 300 mg/mL, 400 mg/mL, 500 mg/mL, 600 mg/mL, 700 mg/mL, 800 mg/mL, 900 mg/mL, 1000 mg/mL. A therapeutic agent and/or odorant may be present in the coating composition at a concentration of 1 pg/mL-1 ng/mL, 1 ng/mL-1 mg/mL, 1 mg/mL-1000 mg/mL. A therapeutic agent and/or odorant may be present in the coating composition at a concentration of 0.01-1000 mg/mL, 0.1-100 mg/mL, or 0.4-40 mg/mL.

A therapeutic agent and/or odorant may be present in the coating at a concentration of 1 pg/cm$^2$, 5 pg/cm$^2$, 10 pg/cm$^2$, 20 pg/cm$^2$, 30 pg/cm$^2$, 40 pg/cm$^2$, 50 pg/cm$^2$, 60 pg/cm$^2$, 70 pg/cm$^2$, 80 pg/mL, 90 pg/cm$^2$, 100 pg/cm$^2$, 300 pg/cm$^2$, 400 pg/cm$^2$, 500 pg/cm$^2$, 600 pg/cm$^2$, 700 pg/cm$^2$, 800 pg/cm$^2$, 900 pg/cm$^2$, 1000 pg/cm$^2$ (1 ng/cm$^2$), 5 ng/cm$^2$, 10 ng/cm$^2$, 20 ng/cm$^2$, 30 ng/cm$^2$, 40 ng/cm$^2$, 50 ng/cm$^2$, 60 ng/cm$^2$, 70 ng/cm$^2$, 80 ng/cm$^2$, 90 ng/cm$^2$, 100 ng/cm$^2$, 200 ng/cm$^2$, 300 ng/cm$^2$, 400 ng/cm$^2$, 500 ng/cm$^2$, 600 ng/cm$^2$, 700 ng/cm$^2$, 800 ng/cm$^2$, 900 ng/cm$^2$, 1000 ng/cm$^2$ (1 µg/cm$^2$), 5 µg/cm$^2$, 10 µg/cm$^2$, 20 µg/cm$^2$, 30 µg/cm$^2$, 40 µg/cm$^2$, 50 µg/cm$^2$, 60 µg/cm$^2$, 70 µg/cm$^2$, 80 µg/cm$^2$, 90 µg/cm$^2$, 100 µg/cm$^2$, 200 µg/cm$^2$, 300 µg/cm$^2$, 400 µg/cm$^2$, 500 µg/cm$^2$, 600 µg/cm$^2$, 700 µg/cm$^2$, 800 µg/cm$^2$, 900 µg/cm$^2$, 1000 µg/cm$^2$ (1 mg/cm$^2$), 5 mg/cm$^2$, 10 mg/cm$^2$, 20 mg/cm$^2$, 30 mg/cm$^2$, 40 mg/cm$^2$, 50 mg/cm$^2$, 60 mg/cm$^2$, 70 mg/cm$^2$, 80 mg/cm$^2$, 90 mg/cm$^2$, 100 mg/cm$^2$, 200 mg/cm$^2$, 300 mg/cm$^2$, 400 mg/cm$^2$, 500 mg/cm$^2$, 600 mg/cm$^2$, 700 mg/cm$^2$, 800 mg/cm$^2$, 900 mg/cm$^2$, 1000 mg/cm$^2$. A therapeutic agent and/or odorant may be present in the coating composition at a concentration of 1 pg/cm$^2$-1 ng/cm$^2$, 1 ng/cm$^2$-1 µg/cm$^2$, 1 µg/cm$^2$-1 mg/cm$^2$, 1 mg/cm$^2$-1 g/cm$^2$. A therapeutic agent and/or odorant may be present in the coating composition at a concentration of 0.01 µg/cm$^2$-1000 µg/cm$^2$, 0.1 µg/cm$^2$-1000 µg/cm$^2$, 1 µg/cm$^2$-1000 µg/cm$^2$ or 10 µg/cm$^2$-1000 µg/cm$^2$, 100 µg/cm$^2$-1000 µg/cm$^2$, 200 µg/cm$^2$-1000 µg/cm$^2$, 300 µg/cm$^2$-1000 µg/cm$^2$, 400 µg/cm$^2$-1000 µg/cm$^2$, 500 µg/cm$^2$-1000 µg/cm$^2$, 600 µg/cm$^2$-1000 µg/cm$^2$, 700 µg/cm$^2$-1000 µg/cm$^2$, 800 µg/cm$^2$-1000 µg/cm$_2$ or 900 µg/cm$^2$-1000 µg/cm$^2$. A therapeutic agent and/or odorant may be present in the coating composition at a concentration of about 100 µg/cm$^2$, about 200 µg/cm$^2$, about 300 µg/cm$^2$, about 400 µg/cm$^2$, about 500 µg/cm$^2$, about 600 µg/cm$^2$, about 700 µg/cm$^2$, about 800 µg/cm$^2$, about 900 µg/cm$^2$, or about 1000 µg/cm$^2$.

The concentration of the therapeutic agent in the polymeric compositions may vary depending on the several factors including the nature of the polymer, the therapeutic agent loaded and the intended application. In some aspects the amount of therapeutic agents loaded on the polymer is in the range of 0.001%-50% w/w for example 0.001%-50% w/w, 0.001%-40% w/w, 0.001%-30% w/w, 0.001%-20% w/w, 0.001%-10% w/w, 0.001%-1% w/w, 0.001%-0.1% w/w, 0.001%-0.01% w/w, 0.01%-50% w/w, 0.01%-40% w/w, 0.01%-30% w/w, 0.01%-20% w/w, 0.01%-10% w/w, 0.01%-1% w/w, 0.01%-0.1% w/w, 0.1%-50% w/w, 0.1%-40% w/w, 0.1%-30% w/w, 0.1%-20% w/w, 0.1%-10% w/w, 0.1%4% w/w, 1%-50% w/w, 1%-40% w/w, 1%-30% w/w, 1%-20% w/w, 01%-10% w/w, 10%-50% w/w, 10%-40% w/w, 10%-30% w/w, 10%-20% w/w, 20%-50% w/w, 20%-40% w/w, 20%-30% w/w, 30%-50% w/w, 30%-40% w/w, or 40%-50% w/w.

The amount or concentration of a therapeutic agent and/or odorant in a polymerized coating can be determined by any means known in the art. For example, the amount or concentration of a therapeutic and/or odorant in a polymerized coating can be determined by extraction of the therapeutic agent and/or odorant from the polymerized coating and analysis of the extracted therapeutic agent. Analysis can be by any means known in the art, for example, by chromatography, e.g., high performance liquid chromatography. The amount or concentration of a therapeutic and/or odorant in a polymerized coating can be determined by monitoring the weight gain of the coated surface. The weight gain may be monitored to back calculate drug and polymer quantity added to the coated surface in order to quantify the drug loading per bulk mesh area.

Coating Methods

The products or product surface as mentioned herein can be coated by any means known in the art. For example, the products can be coated by dipping, spraying, flowing, casting, wicking, pouring, pumping, brushing, or wiping with the coating compositions. Spray coating can involve atomizing the coating composition into a mist and directing the mist to the product (e.g., aerosol spraying). Spray coating may afford more rapid vaporization of one or more solvents present in the coating composition upon formulation, allowing the coating composition to be largely reduced to its non-volatile components upon the product surface upon spraying in a timely manner.

The disclosure also provides methods to facilitate the casting solution, comprising coating formulation, to penetrate the microstructure of the product or product surface. The casting solution may further comprise one or more initiator and/or one or more solvent. The method may comprise (i) determining an appropriate solvent system that would facilitate the casting solution to penetrate into the surface microstructure, (ii) subjecting the coating formulation to polymerization conditions, and (iii) evaporating the solvent to obtain the coated product or product surface. The solvent system may be chosen such that it is miscible with the coating formulation. In some examples, the solvent system is chosen to be volatile so as to facilitate drying of the coated product. The solvent system may comprise one or more solvents. The use of any of the above described solvents is contemplated in the methods of the disclosure. The solvents may be used alone or in combination with one or more other solvents. For example, the solvent system may comprise acetone, ethanol, methanol, water, dichlorobenzene, or any combination thereof.

In some embodiments, the method of the disclosure involves application of a physical means to assist the casting solution to enter the product/product surface microstructure. The method may comprises (i) exposing the product/product surface to a casting solution; (ii) applying a physical force to enable the casting solution to enter the microstructures on the polymeric surface; and (iii) inducing polymerization of the casting solution to obtain the product/product surface coated with a polymeric coating. The physical force may be any force capable of assisting the casting solution into the surface microstructure, for example the physical force may be applied in form of vacuum or pressure. A polymeric surface with overlying casting solution may be positioned within a vessel for application of a pressure change. This pressure change will allow the casting solution to overcome surface tension forces between the casting solution and the underlying polymeric material, allowing the casting solution to penetrate within the microstructure of said polymeric material. Such applications are useful when coating low surface energy materials such as ePTFE, especially that which has been expanded in multiple directions and exhibits multidirectional fibrils in its fibril/node microstructure.

In the event increased pressure is to be applied there may exist one or more downstream openings or ports that are overlaid with the polymeric surface containing overlying casting solution. Upon production of a pressure difference across the polymeric surface containing overlying casting solution, the casting solution may flow in direction of the lower pressure side as the difference is equilibrated. This flow may result in the casting solution penetrating the microstructure of the polymer and coating the surfaces of this microstructure.

In the event reduced pressure is to be applied, there may exist one or more valves which will allow for the cycling of reduced pressure from a vacuum source to some greater pressure. The greater pressure may be atmospheric pressure. The polymeric surface with overlying casting solution is exposed to the reduced pressure which will expand entrapped gasses (e.g., air) within microstructure. This expansion will result in these gases bubbling out through the surrounding casting solution. Upon release of the vacuum, raising the pressure, the remaining gases within the microstructure will compress and pull the surrounding casting solution into the microstructure and allow coating of the internal surface features of the polymeric material. The pressure difference may require multiple cycling to allow complete penetration of the microstructure by the casting solution. For example, the method may involve application of 1, 2, 3, 4, 5, 6, 7, 8, 9, or 10 cycles of pressure difference. In some examples, the method may involve application of more than 10 cycles of pressure difference.

The product or product surface can be pre-wetted with a solvent prior to application of a coating composition. The solvent can be the same solvent that is used in the coating composition. In some cases, the product is not pre-wetted with a solvent prior to application of a coating composition.

Other coating techniques, however, are also deemed to be within the scope of this invention. For example, common coating techniques that are contemplated include reverse roll, rod, and gravure coating methods. Roll coating methods further include kiss coating, single roll coating, and double roll coating, among others.

The coating composition can be applied to the product or product surface in one or more layers, for example the coating composition may be applied in 1, 2, 3, 4, 5, 6, 7, 8, 9, 10 or more layers. The one or more layers can have a thickness. The thickness can be a substantially uniform thickness or may be a non-uniform thickness. The thickness of the coating layer can be 0.01-10 microns. The thickness can be, e.g., 0.01, 0.02, 0.03, 0.04, 0.05, 0.06, 0.07, 0.08, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.7, 7.7, 7.8, 7.9, 8, 8.1, 8.2, 8.3, 8.4, 8.5, 8.8, 8.7, 8.8, 8.9, 9, 9.1, 9.2, 9.3, 9.4, 9.5, 9.9, 9.7, 9.8, 9.9, or 10 microns. The thickness can be, e.g., 0.01-0.1 micron, 0.05-0.5 microns, 0.1-1 microns, 0.5-2 microns, 1-3 microns, 2-6 microns, or 5-10 microns. Said layers may not necessarily be of the same composition and thickness.

Solvent(s) can be evaporated from the coating composition after the coating composition is applied to a product or product surface. Solvent can be evaporated from the coating composition prior to polymerization of the coating onto the product or product surface. In some cases, at least 10%, 25%, 30%, 35%, 40%, 45%, 50%, 55%, 60%, 65%, 70%, 75%, 80%, 90%, 95%, 96%, 97%, 98%, 99%, or 100% of the solvent is evaporated from the coating composition prior to polymerization on the product or product surface. For example, 10-40%, 20-50%, 30-70%, 40-90%, or 70-100% of the solvent may be evaporated from the coating composition prior to polymerization on the product of the product surface. Evaporation of the solvent can be achieved by any means known in the art, including exposing the coated surface to air currents, heating, vacuum (e.g., reduced pressure), or by an evaporation device.

Polymerization of the Coating Compositions

The coating compositions may be polymerized before or after it is applied to a product surface. In some embodiments, the coating is polymerized after it is applied to the product surface. The coating may be polymerized by a curing process. The curing process may involve curing by light, curing by heat, air curing, or any other curing process known to a skilled artisan. Curing by light may be by LED light, by UV light, by visible light, by laser light (e.g., helium, xenon, etc.), or by fluorescent light. The curing may, in some instances, occur in a chamber. The chamber may be a degassing chamber.

In some embodiments, curing can be achieved using a commercially available curing apparatus. Exemplary curing apparatuses include microwave powered UV curing apparatuses (e.g., Heraeus Noblelight Fusion UV curing system, spot UV curing apparatuses (e.g., the Rocket LP apparatus (www.americanultraviolet.com)), the CureJet™ apparatus/light source. An exemplary curing apparatus is described in WO2012012865, hereby incorporated by reference.

The curing apparatus can comprise a light source. The light source can be a visible light source, can be a laser light source, can be a UV light source, can be a fluorescent light source, can be an LED light source, or any combination thereof. The light source can produce a light having an energy output. The energy output of the light can be less than or equal to 20 W/cm². The energy output can be, e.g., 20 W/cm², 19 W/cm², 18 W/cm², 17 W/cm², 16 W/cm², 15 W/cm², 14 W/cm², 13 W/cm², 12 W/cm², 11 W/cm², 10 W/cm², 9 W/cm², 8 W/cm², 7 W/cm², 6 W/cm², 5 W/cm², 4 W/cm², 3 W/cm², 2 W/cm², or 1 W/cm². The energy output can be 1-20 W/cm², 3-15 W/cm², or 7-10 W/cm².

The curing apparatus may comprise a light filter. The light filter may be placed in the light path from the light source to the location of the polymerization reaction. The light filter can be used to control the spectral parameters of the light reaching the polymerization site. The light filter can prevent light of certain wavelengths from reaching the polymerization site. The light filter can, for example, prevent light having wavelengths of 400 nm or above from reaching the polymerization site. The light filter can allow light of specific wavelengths to reach the polymerization site. The light filter can, for example, be configured to allow light of wavelengths between 280-480 nm to reach the polymerization site. The light filter can, for example, be configured to allow light of wavelengths between 280-405 nm to reach the polymerization site. The light filter can, for example, be configured to allow light of wavelengths greater than 325 nm to reach the polymerization site.

The curing apparatus can comprise a site for placing a product to be coated. The location of the site can be adjusted to provide a distance between the light source and the location where polymerization occurs (e.g., polymerization site). The distance can be, e.g., 0.5, 1, 2, 3, 4, 5, 6, 7, 8, 9, 10 cm. The distance can be 0.5-3 cm, 2-5 cm, 4-7 cm, or 6-10 cm. The distance may be 1 inch, 2 inches, 3 inches, 4 inches, 5 inches, 6 inches, 7 inches, 8 inches, 9 inches, 10 inches or more. The curing time may be in the range of a few seconds to several minutes. For example, range from 1 sec to 60 mins. The curing time may be 1 min, 2, min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 25 min, 30 min, 35 min, 40 min, 45 min, 50 min, 55 min, or 60 min. For example, 2 min, 2 min, 3 min, 5 min, or 10 min.

The distance between the polymerization site (taken to be the same as the base of the Rocket LP apparatus) and light source, the spectral properties of the light reaching the polymerization site, and intensity of the source can be adjusted to deliver a range of activation energies to the polymerization site. For example, since intensity and distance are both related to energy delivered per area, an increase in distance can be compensated for by increasing the intensity and vice versa.

The coated products can be further processed after polymerization of the coating. For example, the coated products can be cleaned and sterilized after polymerization of the coating. Cleaning of the coated products can involving exposing the coated product to an environment that will remove coating components that were not polymerized in the polymerization reaction such as residual monomers, co-initiators, initiators, and solvents. Cleaning can be performed but is not limited to solvent washes and exposure to vacuum environments. Solvents can be used to wash out soluble substances from the polymer coating network. Vacuum and/or heat can be used to remove volatile residual components. Sterilization can be achieved by any means known in the art. Any appropriate sterilization process can be used, including the conventional physical or chemical methods or treatment with ionizing radiation such as, for example, gamma or beta rays. The coated products can be placed in a sterile packaging.

The invention also provides kits. A kit may include a coated product in a sterile packaging, and instructions for use. In some cases, a kit may include one or more components for preparing a coating composition of the invention, and instructions for preparing the coating composition using the one or more components.

The invention also provides systems for preparing a coated product of the invention. Systems may comprise a coating composition, a product to be coated, and a curing apparatus. Exemplary compositions, exemplary products, and exemplary curing apparatuses are described herein.

Loading Methods

The therapeutic agents may be loaded on the polymeric coatings. In some embodiments, the therapeutic agent is added to the casting solution such that the therapeutic agent is present during the polymerization reaction and gets incorporated into the polymeric coating.

The therapeutic agents may also be loaded on to the coating post polymerization or post curing. In some example, post curing loading of the therapeutic agents may be the preferable method of loading the therapeutic agents on to the polymeric coating. Post curing loading may be used for any therapeutic agents. In some cases, post curing loading is used for therapeutic agents that contain amine groups. Such therapeutic agents may be susceptible to degradation in the presence of the free radical polymerization. Such therapeutic agents may be those that contain an amine group(s) and may undergo hydrogen abstraction between carbon-hydrogen bonds of the therapeutic agent and the living polymer's radical center which may result in the termination of the polymerization process and degradation of the drug molecule. Such therapeutic agents may also be those that contain an amine group(s) and may undergo hydrogen abstraction between carbon-hydrogen bonds of the therapeutic agent and the activated radical center of initiators and co-initiators which may result in inhibition of the polymerization process and degradation of the drug molecule. In other cases, post curing loading is used for therapeutic agents that do not contain amine groups.

The post curing loading methods of the instant disclosure may comprise (i) soaking the coated product in a solution of a therapeutic agent in a solvent, and (ii) allowing the soaked coated product to dry to obtain the drug eluting coated product.

In some example, the post curing loading methods of the disclosure may comprise (i) applying the a solution of the therapeutic agent in a solvent to the coating surface, (ii) allowing the therapeutic solution to penetrate into the coating for a specified time in an enclosed environment with high levels of the solvent vapor, and (iii) allowing the solvent to evaporate leaving behind the drug-loaded, coated surface.

In some example, the post curing loading methods of the disclosure may comprise (i) exposing a product/product surface to a coating formulation, (ii) conducting the polymerization reaction to obtain the coated product, (iii) soaking the coated product in a solution of a therapeutic agent in a solvent, and (iv) allowing the soaked coated product to dry to obtain the drug eluting coated product.

The soaking period may vary from a few seconds to several days. For example, In some examples, the soaking time for the can be from about 0.1 h to 100 h, or about 1 h to 50 h. In some cases the coated polymeric surface is allowed to soak in a solution of a therapeutic agent for about 5 h-50 h, 10 h-50 h, 15 h-50 h, 20 h-50 h, 25 h-50 h, 30 h-50 h, 35 h-50 h, 40 h-50 h, 45 h-50 h, 5 h-50 h, 10 h-50 h, 15 h-50 h, 20 h-50 h, 25 h-50 h, 30 h-50 h, 35 h-50 h, 40 h-50 h, 45 h-50 h, 5 h-40 h, 10 h-40 h, 15 h-40 h, 20 h-40 h, 25 h-40 h, 30 h-40 h, 35 h-40 h, 40 h-40 h, 5 h-30 h, 10 h-30 h, 15 h-30 h, 20 h-30 h, 25 h-30 h, 5 h-20 h, 10 h-20 h, 15 h-20 h, or 5 h-10 h.

The soaking may be performed at a range of temperature, for example at room temperature, below room temperature or above room temperature. For example, soaking may be performed at a temperature of −20-50° C., −10-50° C., 0-50° C., 10-50° C., 20-50° C., 30-50° C., 40-50° C., −20-40° C., −10-40° C., 0-40° C., 10-40° C., 20-40° C., 30-40° C., −20-30° C., −10-30° C., 0-30° C., 10-30° C., 20-30° C., −20-20° C., −10° C.-20° C., 0-20° C., 10-20° C., −20° C.-10° C., −10° C.-10° C., 0-10° C., −20° C.-0° C., −10° C.-0° C., or −20° C.-10° C. In some examples, the coating is performed at −20° C., −15° C., −10° C., −5° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 35° C., 40° C., 45° C., or 50° C., for example at 4° C.

The soaking may be performed under any number of environments, For example, soaking in the presence of air or under a nitrogen or argon blanket.

The post curing loading methods of the instant disclosure may be performed using any suitable solvents, including the solvents described earlier in the application. For example in some cases the solvent is an alcohol such as methanol, ethanol, isopropyl alcohol, butyl alcohol, or amyl alcohol. In some examples the solvent is methanol. In some examples the solvent is acetonitrile. The concentration of the therapeutic agent in the solvent may vary on several factors including on the nature and solubility of the therapeutic agent, the solvent, the desired concentration of the therapeutic agent in the coating. In some cases the concentration of the therapeutic agent in the solvent is about 0.1-50 mg/mL, for example 0.1-1 mg/mL, 0.1-10 mg/mL, 0.1-20 mg/mL, 0.1-30 mg/mL, 0.1-40 mg/mL, 0.1-50 mg/mL, 1-10 mg/mL. 1-20 mg/mL, 1-30 mg/mL, 1-40 mg/mL, 1-50 mg/mL, 10-20 mg/mL, 10-30 mg/mL, 10-40 mg/mL, 10-50 mg/mL, 20-30 mg/mL, 20-40 mg/mL, 20-50 mg/mL, 30-40 mg/mL, 30-50 mg/mL, or 40-50 mg/mL. In some examples the concentration of the therapeutic agent is about 10 mg/mL. In some examples multiple therapeutics may be loaded at various concentrations in the suitable solvent.

The post curing loading methods of the disclosure may result in an increased loading of the therapeutic product on the polymeric coating as compared to that which is achieved when the polymerization of the coating occurs with the drugs present. In some cases, the post curing loading methods of the disclosure may result in a decreased loading of the therapeutic product on the polymeric coating as compared to that which is achieved when the polymerization of the coating occurs with the drugs present. In other cases, methods of this disclosure may produce equivalent drug loading quantities through use of post cure loading as compared to that that which is achieved when the polymerization of the coating occurs with the drugs present.

The post curing loading methods of the present disclosure may prevent the formation of drug degradation products that may form when the coating is achieved with the drugs present. In some cases, the post curing methods of the disclosure result in at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% reduction in the amount drug degradation products that may form when the coating is achieved with the drugs present. In some cases, the post curing methods of the disclosure result in at most 95%, at most 90%, at most 85%, at most 80%, at most 75%, at most 70%, at most 65%, at most 60%, at most 55%, at most 50%, at most 45%, at most 40%, at most 35%, at most 30%, at most 25%, at most 20%, at most 15%, at most 10%, at most 5% or at most 1% reduction in the amount drug degradation products that may form when the coating is achieved with the drugs present.

The amount of the of drug degradation products formed will depend upon various factors including the nature of the drug and the reaction conditions for the polymerization reaction. The amount of drug degradation products formed during the post curing loading methods of the disclosure may be about 0-10%, about 0-20%, about 0-30%, about 0-40%, about 0-50%, about 0-60%, about 0-70%, about 0-80%, about 0-90%, about 0-100%, 10-20%, about 10-30%, about 10-40%, about 10-50%, about 10-60%, about 10-70%, about 10-80%, about 10-90%, about 10-100%, about 20-30%, about 20-40%, about 20-50%, about 20-60%, about 20-70%, about 20-80%, about 20-90%, about 20-100%, about 30-40%, about 30-50%, about 30-60%, about 30-70%, about 30-80%, about 30-90%, about 30-100%, about 40-50%, about 40-60%, about 40-70%, about 40-80%, about 40-90%, about 40-100%, 50-60%, about 50-70%, about 50-80%, about 50-90%, about 50-100%, about 60-70%, about 60-80%, about 60-90%, about 60-100%, about 70-80%, about 70-90%, about 70-100%, about 80-90%, about 80-100%, about 90-100%. In some cases, the amount of degradation products formed during the post curing loading methods of the disclosure may be about 0%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

The post curing loading method of the disclosure may also comprise rinsing the soaked and dried sample through rinse solutions. The sample may be rinsed once or multiple times. In some cases, the sample is rinsed with a rinse solution one time. In other examples, the sample may be rinsed multiple times, for example 2, 3, 4, 5, 6, 7, 8, 9, 10 or more times. In some examples the soaked and dried sample is rinsed with the rinse solution 2 times. The rinse may be performed with or without shaking. The rinse time may vary depending on several factors including, but not limited to, the nature of the sample, the rinse solution, rinse temperature and manner and extent of shaking. In some cases the rinse is performed from 1-60 sec, for example for 1-10 sec, 1-20 sec, 1-30 sec, 1-40 sec, 1-50 sec, 10-20 sec, 10-30 sec, 10-40 sec, 10-50 sec, 10-60 sec, 20-30 sec, 20-40 sec, 20-50 sec, 20-60 sec, 30-40 sec, 30-50 sec, 30-60 sec, 40-50 sec, 40-60 sec, 50-60 sec. In some cases the rinse is performed for 1 sec, 5 sec, 10 sec, 15 sec, 20 sec, 25 sec, 30 sec, 35 sec, 40 sec, 45 sec, 50 sec, 55 sec or 60 seconds, for example for 15 seconds. In some examples rinse is performed for a period of more than 60 seconds, for example for 5 min, 10 min, 15 min, 20 min, 25 min, 30 min, 35 min, 40 min, 45 min, 50 min, 60 min, or more. The method may further comprise drying the rinsed and coated surfaces. Drying may be achieved by any suitable means for example by simply allow the coated and rinsed sample to air dry. Rinse may be performed by any suitable temperature, or example at room temperature, below room temperature or above room temperature.

The amount of drug loading may be monitored by a variety of analytical techniques. For example, the drugs from the sample may be extracted by soaking the coated surface in a suitable solvent and the drug quantities within the extract may be determined using a suitable analytical technique, for example HPLC.

The coating may be polymerized by a curing process. The curing process may involve curing by light, curing by heat, air curing, or any other curing process known to a skilled artisan. Curing by light may be by LED light, by UV light, by visible light, by laser light (e.g., helium, xenon, etc.), or by fluorescent light. The curing may, in some instances, occur in a chamber. The chamber may be a degassing or inert gas chamber.

In some embodiments, curing can be achieved using a commercially available curing apparatus. Exemplary curing apparatuses include microwave powered UV curing apparatuses (e.g., Heraeus Noblelight Fusion UV curing system, spot UV curing apparatuses (e.g., the Rocket LP apparatus (www.americanultraviolet.com)), the CureJet™ apparatus/light source. An exemplary curing apparatus is described in WO2012012865, hereby incorporated by reference.

The curing apparatus can comprise a light source. The light source can be a visible light source, can be a laser light source, can be a UV light source, can be a fluorescent light source, can be an LED light source, or any combination thereof. The light source can produce a light having an energy output. The energy output of the light can be less than or equal to 20 W/cm$^2$. The energy output can be, e.g., 20 W/cm$^2$, 19 W/cm$^2$, 18 W/cm$^2$, 17 W/cm$^2$, 16 W/cm$^2$, 15 W/cm$^2$, 14 W/cm$^2$, 13 W/cm$^2$, 12 W/cm$^2$, 11 W/cm$^2$, 10 W/cm$^2$, 9 W/cm$^2$, 8 W/cm$^2$, 7 W/cm$^2$, 6 W/cm$^2$, 5 W/cm$^2$, 4 W/cm$^2$, 3 W/cm$^2$, 2 W/cm$^2$, 1 W/cm$^2$, 0.9 W/cm$^2$, 0.8 W/cm$^2$, 0.7 W/cm$^2$, 0.6 W/cm$^2$, 0.5 W/cm$^2$, 0.4 W/cm$^2$, 0.3 W/cm$^2$, 0.2 W/cm$^2$, 0.1 W/cm$^2$, 0.09 W/cm$^2$, 0.08 W/cm$^2$, 0.07 W/cm$^2$, 0.06 W/cm$^2$, 0.05 W/cm$^2$, 0.04 W/cm$^2$, 0.03 W/cm$^2$, 0.02 W/cm$^2$, or 0.01 W/cm2. The energy output can be 0.01-20 W/cm$^2$, 0.01-10 W/cm$^2$, 0.01-1 W/cm$^2$, 0.01-0.1 W/cm$^2$, 0.1-10 W/cm$^2$, 3-15 W/cm$^2$, or 7-10 W/cm$^2$.

The curing apparatus may comprise a light filter. The light filter may be placed in the light path from the light source to the location of the polymerization reaction. The light filter can be used to control the spectral parameters of the light reaching the polymerization site. The light filter can prevent light of certain wavelengths from reaching the polymerization site. The light filter can, for example, prevent light having wavelengths of 400 nm or above from reaching the polymerization site. The light filter can allow light of specific wavelengths to reach the polymerization site. The light filter can, for example, be configured to allow light of wavelengths between 280-480 nm to reach the polymerization site. The light filter can, for example, be configured to allow light of wavelengths between 280-405 nm to reach the polymerization site. The light filter can, for example, be configured to allow light of wavelengths greater than 325 nm to reach the polymerization site.

The curing apparatus can comprise a site for placing a product to be coated. The location of the site can be adjusted to provide a distance between the light source and the location where polymerization occurs (e.g., polymerization site). The distance can be, e.g., 0.5, 1, 2, 3, 4, 5, 6, 7, 8, 9, 10 cm. The distance can be 0.5-3 cm, 2-5 cm, 4-7 cm, or 6-10 cm.

The coated products can be further processed after polymerization of the coating. For example, the coated products can be sterilized after polymerization of the coating. Sterilization can be achieved by any means known in the art. Any appropriate sterilization process can be used, including the conventional physical or chemical methods or treatment with ionizing radiation such as, for example, gamma or beta rays. The coated products can be placed in a sterile packaging.

Applications/Coated Products

In coating compositions and methods of the disclosure may be applied to a variety of products. The product to be coated can be a man-made product or naturally occurring. The protective coatings of the present disclosure may be used on a variety of surfaces. The coatings form the present disclosure may be used to cover polymeric surfaces. The polymeric surfaces may comprise natural polymers for example cellulose (in wood and paper), collagen, alginate, chitosan, and chitin, or synthetic polymers. A polymeric surface may be plastic surfaces. Examples of plastic surfaces that may be protected by the protective coatings of the present disclosure include polystyrenes (PS), polyethylenes, polyethylene terephthalate, polypropylene (PP), polyvinyl chloride (PVC), nylon, rubber (synthetic and natural), Polyvinylidene chloride (PVDC), Low-density polyethylene (LDPE), Polyamides (PA), Acrylonitrile butadiene styrene (ABS), Polyethylene/Acrylonitrile Butadiene Styrene (PE/ABS), Polycarbonate (PC), Polycarbonate/Acrylonitrile Butadiene Styrene (PC/ABS), polytetrafluoroethylene (PTFE), expanded polyteteratfluoroethylene (ePTFE), and Polyurethanes (PU).

A coating comprising a polymer resulting from the polymerization of monomers may be applied to fluoropolymers. The fluoropolymer can be prepared from a monomer or from flow-work of bulk polymer or polymer resin. For example the fluoropolymer can be prepared from: Ethylene (E), Propylene (P), Vinyl fluoride (VF1), Vinylidene fluoride (VDF or VF2), Tetrafluoroethylene (TFE), Hexafluoropropylene (HFP), Perfluoropropylvinylether (PPVE), Perfluoromethylvinylether (PMVE), or Chlorotrifluoroethylene (CTFE). The fluoropolymer can be, for example, PVF (polyvinylfluoride), PVDF (polyvinylidene fluoride), PTFE (polytetrafluoroethylene), PCTFE (polychlorotrifluoroethylene), PFA (perfluoroalkoxy polymer), FEP (fluorinated ethylene-propylene), ETFE (polyethylenetetrafluoroethylene), ECTFE (polyethylenechlorotrifluoroethylene), FFPM/FFKM (Perfluorinated Elastomer [Perfluoroelastomer]), FPM/FKM (Fluorocarbon [Chlorotrifluoroethylenevinylidene fluoride]), PFPE (Perfluoropolyether), or PFSA (Perfluorosulfonic acid). The fluoropolymer can be prepared through chemical-, thermal-, and/or mechanical-induced consolidation of polymerized resin particles or from cuts (such as skives) from bulk polymer (such as billets). The fluoropolymer can be treated to improve its properties associated with the disclosure. For example improve adhesion strength can in some embodiments be achieved by incorporating use of high-energy vis/UV radiation, plasma, or chemical treatment to create a reactive PTFE or ePTFE surface with a higher surface energy.

In some embodiments, coatings of the present disclosure may be used on metallic surfaces. Metallic surfaces commonly used include carbon-based, copper, iron, magnesium, nickel, chromium, gold, silver, platinum, zinc, aluminum, tin, tungsten, titanium, valadium, and mercury. Surfaces comprising metal alloys may also be protected by the methods of the current disclosure. Non-limiting examples of the metal alloys include alloys of common engineering metals including aluminum, chromium, copper, iron, magnesium, nickel, titanium, valadium, and zinc. In various embodiments surface may be (galvanized/stainless), aluminum alloys, magnesium alloys, copper-nickel alloys, nickel-based superalloys like Inconel.

The protective coatings of the present disclosure may also be used with glass surfaces. Glass surface may comprise of silicate glass such as fused silica glass, soda-lime-silica glass, sodium borosilicate glass, lead-oxide glass, aluminosilicate glass, oxide glass, recycled glass, network glass, colloidal glass, glass-ceramics or polymer glass (for example acrylic glass, polycarbonate, polyethylene terephthalate).

The material of the substrate can be porous. Porosity can be measured as a fraction or percentage of the empty space/total volume of the substrate. The porous material can be highly porous. A highly porous material can have a porosity of over 50%, 55%, 60%, 65%, 70%, 75%, 80%, 85%, 90%, 95%, 99%, or over 99%. A highly porous material (e.g., a highly porous ePTFE material) can have a porosity of 50-60%, 60-75%, 75-90%, 90-99%, or over 99%. The porous material can have a low porosity. The low-porosity material (such as, e.g., a low-porosity ePTFE material), can have a porosity of less than 50%, less than 45%, less than 40%, less than 35%, less than 30%, less than 25%, less than 20%, less than 15%, less than 10%, less than 5%, less than 2.5%, less than 1%, less than 0.5%, less than 0.1%, or substantially 0%. The low-porosity material (e.g., a low-porosity ePTFE) can have a porosity of 0-5%, 2-10%, 5-20%, 15-30%, 20-40%, or 30-50%. The pores of the porous material, whether highly porous or of low porosity, can have an average diameter. The average diameter of the pores can be 0.001 microns, 0.005 microns, 0.01 microns, 0.05 microns, 0.1 microns, 0.15 microns, 0.2 microns, 0.25 microns, 0.3 microns, 0.35 microns, 0.4 microns, 0.45 microns, 0.5 microns, 0.55 microns, 0.6 microns, 0.65 microns, 0.7 microns, 0.75 microns, 0.8 microns, 0.85 microns, 0.9 microns, 0.95 microns, 1 microns, 1.5 microns, 2 microns, 3 microns, 4 microns, 5 microns, 6 microns, 7 microns, 8 microns, 9 microns, 10 microns, 15 microns, 20 microns, 25 microns, 30 microns, 40 microns, 50 microns, 60 microns, 70 microns, 80 microns, 90 microns, 100 microns, 200 microns, 300 microns, 400 microns, 500 microns, 600 microns, 700 microns, 800 microns, 900 microns, 1000 microns, 1100 microns, 1200 microns, 1300 microns, 1400 microns, 1500 microns, 1600 microns, 1700 microns, 1800 microns, 1900 microns, 2000 microns, 2100 microns, 2200 microns, 2300 microns, 2400 microns, 2500 microns, 2600 microns, 2700 microns, 2800 microns, 2900 microns, 3000 microns, 3100 microns, 3200 microns, 3300 microns, 3400 microns, 3500 microns, 3600 microns, 3700 microns, 3800 microns, 3900 microns, 4000 microns, 4100 microns, 4200 microns, 4300 microns, 4400 microns, 4500 microns, 4600 microns, 4700 microns, 4800 microns, 4900 microns, 5000 microns, 5100 microns, 5200 microns, 5300 microns, 5400 microns, 5500 microns, 5600 microns, 5700 microns, 5800 microns, 5900 microns, 6000 microns, 6100 microns, 6200 microns, 6300 microns, 6400 microns, 6500 microns, 6600 microns, 6700 microns, 6800 microns, 6900 microns, 7000 microns, 7100 microns, 7200 microns, 7300 microns, 7400 microns, 7500 microns, 7600 microns, 7700 microns, 7800 microns, 7900 microns, 8000 microns, 8100 microns, 8200 microns, 8300 microns, 8400 microns, 8500 microns, 8600 microns, 8700 microns, 8800 microns, 8900 microns, 9000 microns, 9100 microns, 9200 microns, 9300 microns, 9400 microns, 9500 microns, 9600 microns, 9700 microns, 9800 microns, 9900 microns, or 10000 microns. The average diameter of the pores can be 0.001-0.01 microns, 0.01-0.1 microns, 0.1-0.3 microns, 0.3-1 microns, 2-10 microns, 3-22 microns, 10-50 microns, 40-100 microns, 100-1000 microns, 100-10000 microns, 1000-10000 microns.

The product to be coated may also comprise materials such as paper, paper laminates, non-woven materials, non-woven laminates, and other similar substrates. The coatings of the disclosure can be applied to, e.g., surgical gowns and drapes, examining table paper, hospital bed pads, hospital bed inserts and sheeting, gloves, routine fixtures, and surgical masks.

The product to be coated can be a medical device. The term 'medical device' is used herein to encompass all medical apparatuses which are used in the treatment of, and come in contact with, a human or animal body or its blood, fluids or other biological membranes. Exemplary medical devices include, e.g., a mesh, a suture mesh, a wound dressing, a stent, a skin patch, a bandage, a prosthetic, a suture anchor, a screw, a pin, a cannula, a tack, a rod, an angioplastic plug, a plate, a clip, a ring, a needle, a tube, an orthopedic implant, a guided tissue matrix, an aortic aneurysm graft device, a shunt (e.g., an arteriovenous shunt), a catheter, a valve (e.g., a heart valve), a pump, an artificial joint, hemodialysis catheter, a marker, a bone-fracture healing device, a bone replacement device, a joint replacement device, a tissue regeneration device, a tumor targeting and destruction device, a periodontal device, a hernia repair device, a hemodialysis graft, an indwelling arterial catheter, an indwelling venous catheter, a pacemaker casing, a pacemaker lead, a pacemaker, a patent foramen ovale septal closure device, a vascular stent, a tracheal stent, an esophageal stent, a urethral stent, a rectal stent, a stent graft, a synthetic vascular graft, a vascular aneurysm occluder, a vascular clip, a vascular prosthetic filter, a vascular sheath, a drug delivery port and a venous valve.

Coated Stent

The coating formulations and/or the methods of the disclosure may be applied to a stent. Accordingly, the disclosure provides a stent coated with one or more layers of the compositions described herein. The term "stent" herein means any device which when placed into contact with a site in the wall of a lumen to be treated, will also place fibrin at the lumen wall and retain it at the lumen wall. This can include especially devices delivered percutaneously to treat coronary artery occlusions and to seal dissections or aneurysms of splenic, carotid, iliac and popliteal vessels. Any stent known in the art can be coated with an disclosure coating. For example, the stent can be as described in U.S. Pat. No. 4,886,062, hereby incorporated by reference. The stent can be a self-expanding stent. The self-expanding stent can be made of a resilient polymeric material such as that disclosed in published international patent application WO 91/12779, hereby incorporated by reference.

Coated Soft Tissue Mesh

The coating formulations and/or the methods of the disclosure may be applied to a soft tissue mesh. In some embodiments, the coated product is a coated soft tissue mesh. The term "mesh", as used herein, can refer to a semi-permeable structure. Soft tissue meshes generally comprise a flexible material. The material of the soft tissue mesh can be any of the materials described herein. Exemplary materials include PTFE, ePTFE, polypropylene, expanded polypropylene. A soft tissue mesh can comprise pores. The pores may be closely spaced. In some cases, the soft tissue mesh comprises filaments. The filaments may be of a synthetic material. In some cases, the soft tissue mesh has a first surface and a second surface. The first and second surfaces may be on opposite sides of the mesh, e.g., the ventral and dorsal side. In some cases, one surface is a smooth surface and the opposite surface is a textured surface. Exemplary meshes include, e.g., Gore® DualMesh® Biomaterial (Gore Medical), VENTRIO™ Hernia Patch (Davol), Ventralex™ Hernia Patch (Bard), and PROCEED™ Ventral Patch (Ethicon). Such meshes can be used in a variety of medical applications, for example, meshes can be used as surgical implant for hernia repair, e.g., a hernia patch. A mesh, according to the present embodiments, can be formed by weaving, interlacing, interweaving, knotting, knitting, winding, braiding, electrospinning, skiving, and/or entangling the elongated elements so they come in contact to form a network of nodes, knots, or hubs separated by holes or openings. Alternatively, a mesh can be formed by punching, drilling, cutting, mold casting, or otherwise forming the holes in a sheet of the mesh material.

A three-dimensional mesh is formed by either forming a sheet, staking several mesh sheets or by bending a mesh sheet into a hollow or tubular object. Exemplary meshes include, without limitation, gauze, a screen, a strainer, a filter, a stent, a wound-dressing and the likes. For example, a stent, such as the widely used medical device in angioplasty, bronchoscopy, colonoscopy, esophagogastroduodenoscopy and to treat restenosis and other cardiovascular conditions, is an example of a three-dimensional mesh of struts which are interconnected in a orderly fashion and shaped into a cylindrical tube. Hence, according to embodiments of the present disclosure, the mesh can take the form or be shaped so as to have a form such as a sheet, a tube, a sphere, a box, and a cylinder. Such shapes may be trimmed for custom fitting during the end use.

The coating of an entire pre-fabricated core structure such as a mesh as presented herein, is realized in the nodes, junctions, intercrossing, hubs or otherwise the points of contact where individual sub-structural elements meet (referred to herein and encompassed under the phrase "intercrossing junctions"). For example, in the case where the core structure is a mesh, when a mesh is woven from pre-coated fibers, two intercrossing fibrous core elements do not come in contact with each other when they form a junction since they are separated with at least two coat layers sheathing each thereof. In the coated pre-fabricated meshes presented herein, the core elements touch each other via direct physical contact and the entire junction which is formed therebetween is coated as a whole without having a coat material separating the elements. In practice, this feature expresses itself mainly in the way the mesh experiences the gradual degradation of the coat layer. In a mesh which is weaved from pre-coated fibers, the mesh may loosen and even come apart when the coating layers thins and dwindles as a result of its capacity to biodegrade, or in other cases the polymeric coat may swell and cause the element to distance each other causing a deformation of the core structure to some extent, while the coated pre-fabricated meshes do not experience any change due to the erosion or swelling of the coat and thus the mesh or other similar core structure maintains its structural integrity and stability throughout the process of degradation or swelling of the coat.

Meshes that can be employed as surgical implants include, for example, polypropylene mesh (PPM) which has been used extensively in hernia repair to provide the necessary strength and support for tissue growth for the repair of abdominal defects in hernia. Other examples include expanded polytetraflouroethylene (ePTFE), highly porous ePTFE, low porosity ePTFE, compressed PTFE, sepramesh biosurgical composite, compressed sepramesh biosurgical composit, polyethylene terephthalate (PET), compressed PET, and titanium.

Implants may have a dorsal surface and a ventral surface. The dorsal surface is the portion of the implant which faces outward away from a fascia defect and the ventral surface is the portion which faces inward towards the defect. Prior to implantation, some of the implants described herein may, in an unstressed state, assume a flat or planar shape, or may assume a concave and/or convex shape on one or more surfaces. Implants may comprise surface modifications.

The hernia patch can comprise a material as described in U.S. Pat. No. 6,780,497, which is hereby incorporated by reference. For example, the hernia patch can comprise an ePTFE composition, wherein the ePTFE composition comprises a macro-roughened surface characterized by ridges and valleys, and further wherein the ePTFE composition is microporous or macroporous. The ePTFE composition can be as described in U.S. Pat. No. 7,666,496, hereby incorporated by reference.

The mesh can be in the form of a sponge. The sponge can either be made from a synthetic material, such as polyvinyl alcohol, or from a bioabsorbable material, such as collagen, gelatin, keratin, laminin, fibrin, or fibronectin. Examples include HELISTAT®, HELITENE®, and VITAGUARD® (Integra Life Sciences, Plainsboro, N.J.), and ULTRAFOAM® (Davol, Inc., Cranston, R.I.). In certain instances, the sponge can be a bioabsorbable sponge that is only temporarily present in the body of a subject. Meshes and sponges described herein may also be referred to by other terms, such as for example, a pad or a gauze, etc.

A mesh may be sufficiently flexible to allow a surgeon to manipulate the implant to conform to the surgical site and/or ease delivery during a laparoscopic procedure. However, in some circumstances, a stiffer arrangement that limits compression and/or expansion of the mesh may be preferred. In certain embodiments, a mesh is be collapsible, such as by folding, rolling, or otherwise, into a slender configuration, so that it may be delivered through a narrow lumen of a laparoscopic device. Flexibility of the implant is influenced by many factors, including, the materials from which the implant is made, treatments applied to the implant or any other features of the body of the implant. A mesh may either include a single mesh or be formed from two or more mesh segments that are joined or overlap.

Various methods of hernia repair and implants suitable for use in hernia repair are known and described, for example, in U.S. Pat. Nos. 5,176,692; 5,569,273; 6,800,0825,824,082; 6,166,286; 5,290,217; and 5,356,432. Generally, such devices include (a) a mesh-like member configured for repairing a fascia defect in a subject; and optionally (b) a means for securing the mesh-like member to the site of the fascia.

Coated Catheter

In some embodiments, the coated product is a coated catheter. Catheters can be configured for, e.g., intravenous, arterial, peritoneal, pleural, intrathecal, subdural, urological, synovial, gynecological, percutaneous, gastrointestinal, abscess drains, and subcutaneous applications. Catheters can be used for short-term, intermediate, and long-term applications. Types of catheters include standard IV, peripherally inserted central catheters (PICC)/midline, central venous catheters (CVC), angiographic catheters, urinary catheters, guide catheters, feeding tubes, endoscopy catheters, Foley catheters, drainage catheters, external catheter (e.g., condom catheter), and needles.

The catheter can be a venous catheter. Central venous catheters and peripheral venous catheters are contemplated in the disclosure. The central venous catheter can be a non-tunneled catheter or a tunneled catheter. Non-tunneled catheters can be fixed in place at the site of insertion, with the catheter and attachments protruding directly. Commonly used non-tunneled catheters include Quinton catheters. Tunneled catheters can be passed under the skin from the insertion site to a separate exit site, where the catheter and its attachments emerge from underneath the skin. The exit site can be typically located in the chest, making the access ports less visible than if they were to directly protrude from the neck. Passing the catheter under the skin helps to prevent infection and provides stability. Commonly used tunneled catheters include Hickman catheters and Groshong catheters. The peripheral venous catheter can be configured for insertion into a peripheral vein.

The catheter can be a dialysis catheter. The dialysis catheter can be configured to exchange blood to and from a hemodialysis machine to a subject, e.g., a human patient. The dialysis catheter can be a tunneled dialysis catheter or a non-tunneled dialysis catheter.

In some embodiments, in addition to a coating of the disclosure, the coated catheter can further comprise a hydrophilic surface coating. When immersed in water the hydrophilic surface coating can swell to a smooth, slippery film. The smooth, slippery film can render the catheter safer and more comfortable to insert.

The disclosure coatings may be applied to an electronic device. The electronic device may or may not be a hand-held device. Accordingly, the disclosure also provides an electronic device coated with a coating composition described herein. Electronic devices may be electronic equipment intended for everyday use (consumer electronic). An electronic device may be a device for entertainment, communications and office productivity. Examples of consumer electronic that may be coated with the protective coating of the disclosure include personal computers, telephones, MP3 players, audio equipment, televisions, calculators, GPS automotive electronics, digital sphygmomanometers, digital glucose meters, digital cameras and players and recorders using video media such as DVDs, VCRs or camcorders. More specifically the protective coatings of the present disclosure may be used on mobile devises for example on mobile phones including touchscreen phones, iPods, iPads and other tablet personal computers. The protective coating form the present disclosure may also be used on electronic devices intended for community use, for examples personal computers, key boards, mouse or televisions in public libraries.

In further embodiments, the disclosure coatings may be used on other house hold objects that exhibit microorganism and/or viral contamination. Non-limiting examples of such objects include buttons, handles, knobs, steering controls, toilets, etc. In further embodiments, the protective coatings of the present disclosure may be used on items that are both communal in nature and are intended for physical contact for example in public toilets and payphones.

EXAMPLES

General

Experiments noted as Examples 1 through 5 discussed below were performed using 1 mm thick DualMesh Biomaterial (Gore Medical). The material consisted of a porous side which surface consists of ridges and valleys and a smooth side, see FIG. 2. The valleys were cut (using a laser ablation) out of the bulk material which persisted in part as the ridges and was identical to that shown in FIG. 1b. Cut out valleys are shown in FIG. 2. The smooth surface consisted of a thin film of multidirectional pulled ePTFE which had been bonded on the thicker, porous portion, see FIG. 3.

Experiments noted as Examples 6 through 13 discussed below were performed using polypropylene mesh (part number PPKM601 (Textile Development Associoates, Inc.)). The mesh had a bulk density of 107 g/m$^2$ as determined by ASTM D-3776, 0.61 mm thickness as determined by ASTM D-1777, grab strength of 537 N/2.5 cm in machine direction and 454 N/2.5 cm in cross machine direction as determined by ASTM D-5034, percent elongation of 94 in machine direction and 123 in cross machine direction as determined by ASTM D-5034, and Mullen burst strength of 1210 kPa as determined by ASTM D-3786.

Example 1

Methacrylate Coating of an ePTFE Surface Formed by Multidirectional Pulling Using a 1:1 Mixture of Ethanol and Acetone as Solvent to Encourage the Casting System to Penetrate the ePTFE Microstructure In an attempt to overcome the surface build-up issues, a solvent system was designed which would be miscible with the various casting formulations, passively penetrate into the microstructure of the ePTFE shown in FIGS. 1 and 2 due to low viscosity and low surface tension, and evaporate within a relatively short amount of time due to having a relatively high vapor pressure.

A 1:1 v/v blend of ethanol and acetone was selected to fulfill this role. It was believed that filling the porosity of the ePTFE with an amount of the solvent system equivalent to the monomer casting system (containing an independent solvent system) to be used and then applying the casting system on the surface of the ePTFE this would allow the casting system-associated solvent, monomers, drugs, and initiator to penetrate into the ePTFE microstructure as the casting system (on top of the ePTFE) mixed with the solvent system (inside the ePTFE pores). Then once the majority of solvents (derived from both the new solvent system and the casting system formulation) had evaporated, the polymerization reaction was induced, resulting in the final drug delivery coating. FIG. 4 shows that build-up and pore clogging, although improved based on gross observation of traditional coating attempts, still persisted to an unacceptable extent. The results may be explained by assuming that the movement of solvent off of the surface with evaporation would pull the monomer, drugs, and the initiators to the outer surfaces. The other possible explanation may be that the mixing with the new solvent system which had penetrated into the depths of the microstructure never occurred to any appreciable extent and the monomer, drugs, and the initiators were left sitting on the surface.

Example 2

Methacrylate Coating of an ePTFE Surface Formed by Multidirectional Pulling with Use of a Pressure Differential Across the DualMesh with Casting Solution Applied to the High Pressure Side This Example pursued a physical means of assisting monomer, solvent, and drug casting solution penetration within the microstructure using a syringe. A circular DualMesh specimen with diameter less than the syringe bore was positioned within syringe barrel with the smooth side of DualMesh at the base of the barrel and facing the entrance to the port. With plunger removed and the port of the syringe facing down, the casting solution was applied to the upper valley/ridge side of the DualMesh. The plunger was then inserted into the barrel and pressure was applied. Pressure was relieved as the casting solution was forced through the ePTFE microstructure and air was released through the syringe port. The circular specimen was then removed from the syringe barrel and polymerization was induced via photoinitiator activation.

This method resulted in a great improvement over those of Example 1. FIG. 5 shows the rough side's ridge and valley formation of the coated DualMesh material. It can be see that although improved the coating still resulted in pore clogging and occasional large deposits. It is believed that upon initial application of the pressure and fluid flow the casting solution begins to penetrate into the microstructure of the ePTFE, but after a path for air flow has been established through the construct that air may flow with less resistance through this path (a path free of casting solution) air will preferentially take this route. This preferential air flow route theory may explain why there is still a larger portion of the coating material on the surface than is to be expected if it were evenly distributed throughout the microstructure.

Example 3

Methacrylate Coating of a Multidirectional Pulled ePTFE Surface Using Vacuum to Induce Fluid Flow Through Expansion and Evacuation of the Air within the ePTFE Microstructure Based on findings from the attempts discussed in Examples 1 and 2, the use of fluid flow seemed beneficial in terms of having the ability to incorporate the casting solution within the ePTFE microstructure, but the use of a pressure differential across the DualMesh with casting solution applied to the high pressure side did not completely alleviate coating buildup. This observation led to the concept of using vacuum to induce fluid flow through expansion of the air within the ePTFE microstructure.

DualMesh specimens were placed within an apparatus to which a vacuum may be generated (custom made using a microscope slide, parafilm, and modified syringe initially and vacuum desiccator equipped with a three-way venting stopcock later) with the rough side facing up. The drug-loaded casting solution was applied to the surface of the DualMesh. The vessel was sealed and a vacuum was applied. This resulted in the air within the microstructure expanding beyond the available volume of the ePTFE pores and exiting as bubbles in to the casting solution above. The act of bubbling and in some instances cycling of the vacuum application resulted in the casting solution evenly penetrating into the microstructure. After this DualMesh was removed from the chamber, a large amount of solvent was allowed to evaporate, and the coating was cured. FIGS. 6 and 7 show micrographs of an acceptable coating made using this method. Pores can be seen to remain largely open on all surfaces.

Example 4

Post Curing Loading of Drugs on Methacrylate Polymeric Coatings

Certain drugs, especially those which contain amine groups and unsaturated bonds, are susceptible to degradation in the presence of the free radical chain growth vinyl polymerization and activated photoinitiators due to the phenomenon of a chain transfer reaction known as hydrogen abstraction between carbon-hydrogen bonds and the living polymer's and activated photoinitiators radical end and reduction of unsaturated carbon-carbon bonds by the living polymer's and activated photoinitiator's radical centers. Polymerization may be terminated and the drug molecule may be degraded. This observation is not a surprise as amine groups and their neighboring carbons can participate in this chain termination reaction. We have developed a process to produce equivalent drug loading quantities in DualMesh Biomaterial through use of post cure loading as compared to that that which is achieved when the polymerization of the coating occurs with the drugs present. Although similar loading quantities are achieved, it is desirable to load post cure so that drug degradation products are not included within the resulting coating's polymer network.

An acetone:ethanol:BPDM solution:NTG-GMA solution in 1:1:1:1 volume ratio was used to coat DualMesh Biomaterial with drugs both present during the polymerization process and loaded into the polymer network after curing had been performed. Circular 0.785 $cm^2$ samples of DualMesh were coated. In the version were drugs were included in the casting solution, both minocycline hydrochloride and rifampin were incorporated at levels such if no degradation were to have occurred each drug would have been loaded at a bulk surface area density of 400 $\mu g/cm^2$. The post-cure loaded version was created by coating the DualMesh with the same amount of polymer coating, and then submerging the specimen in a 5 mL methanol bath containing each drug at 10 mg/mL overnight (~18 hours) at 4° C. After soaking in the methanol/drug solution, specimens were retrieved from the loading solution and allowed to air dry. Once dried they were passed through two rinse solutions using the following technique: forceps were used to hold specimens while contacting a minimal amount of the surface, vigorously shake the specimen in a 15 mL methanol rinse for 15 seconds, move specimen to a second 15 mL methanol bath and vigorously shake for an additional 15 seconds, and finally allow to air dry. Shaking was performed by moving the forceps back while holding the specimen submerged in the rinse.

Figure 8:
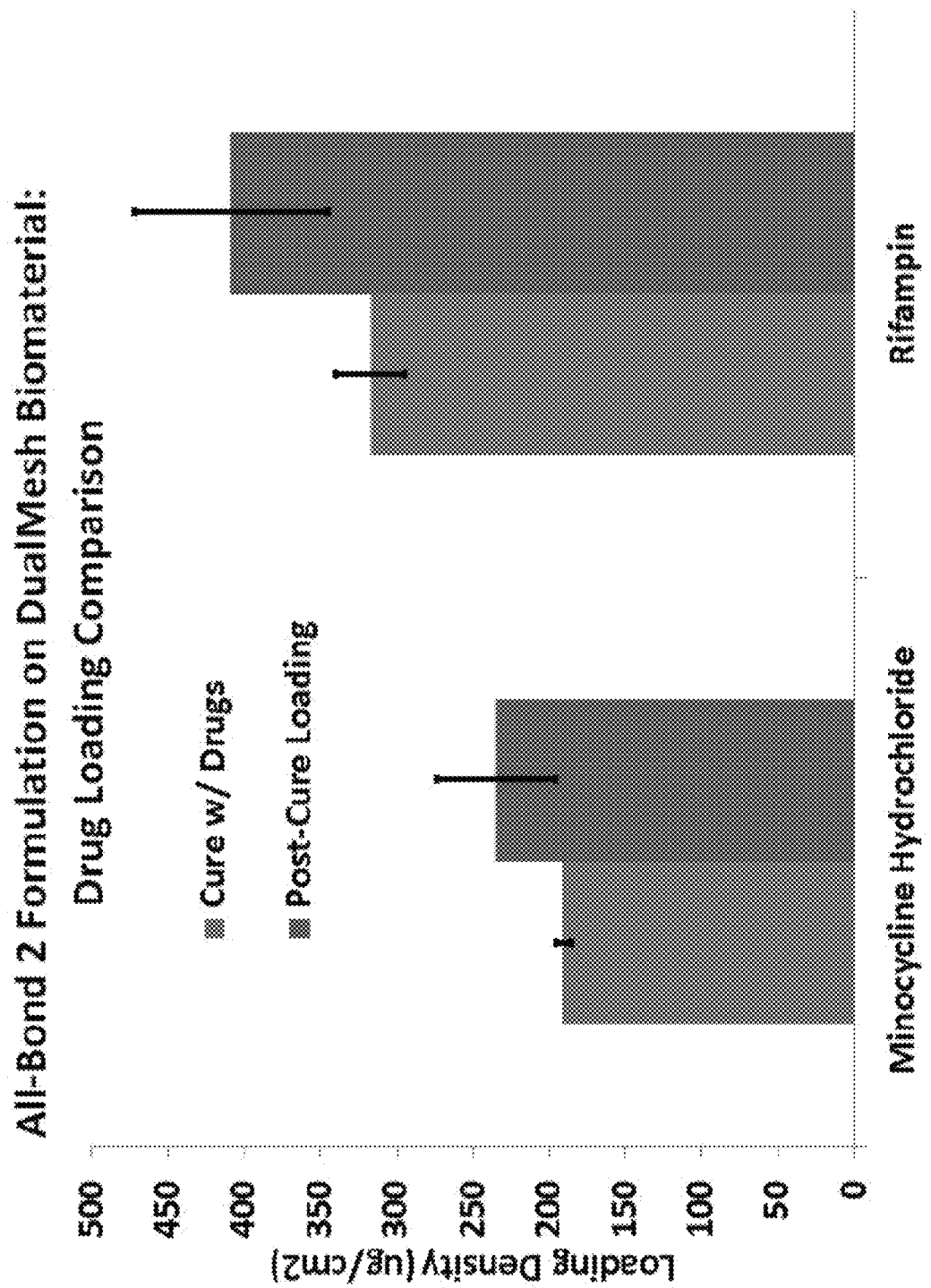
FIG. 8. Shows a comparison of minocycline and rifampin loading methods, as total quantity of extracts obtained from coatings polymerized with drug present and coatings which had drugs loaded post curing.

Drugs from each specimen were individually extracted in 1 mL of methanol at 4° C. overnight. Drug quantities within each extract were determined using HPLC, and results are presented in FIG. 8. The data demonstrates that average drug survival during the polymerization process was 48% and 79% for minocycline and rifampin, respectively. Additionally taking the target loading as 400 $\mu g/cm^2$, the post cure loading process currently used a methanol drug loading solution of 10 mg/mL of each drug which resulted in 59% and 102% of the target value for minocycline and rifampin, respectively. Raising the concentration of minocycline in the methanol loading solution would likely allow for a value more in line with the target value.

Example 5

Methanol Rinse

Figure 9:
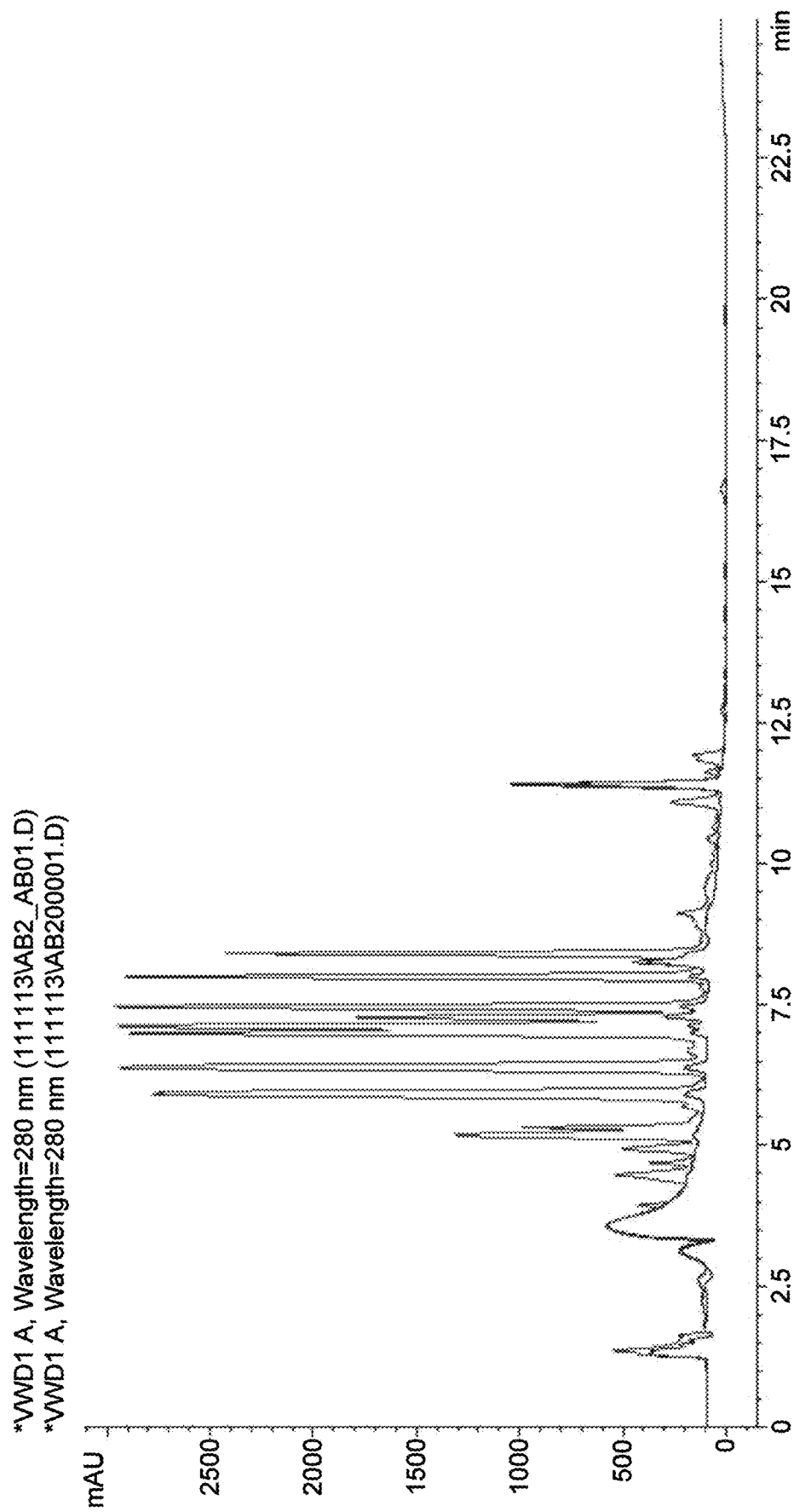
FIG. 9. Shows overlaid chromatographs demonstrating the removal of contaminants in the methanol rinse specimen (blue) as compared to the specimen that was not rinsed (red). The numerous large peaks shown in the red chromatograph are greatly reduced in the blue, demonstrating reduction of these components during the methanol rinse. Two black arrows have been added to show minocycline (left arrow) and rifampin (right arrow).
Figure 10:
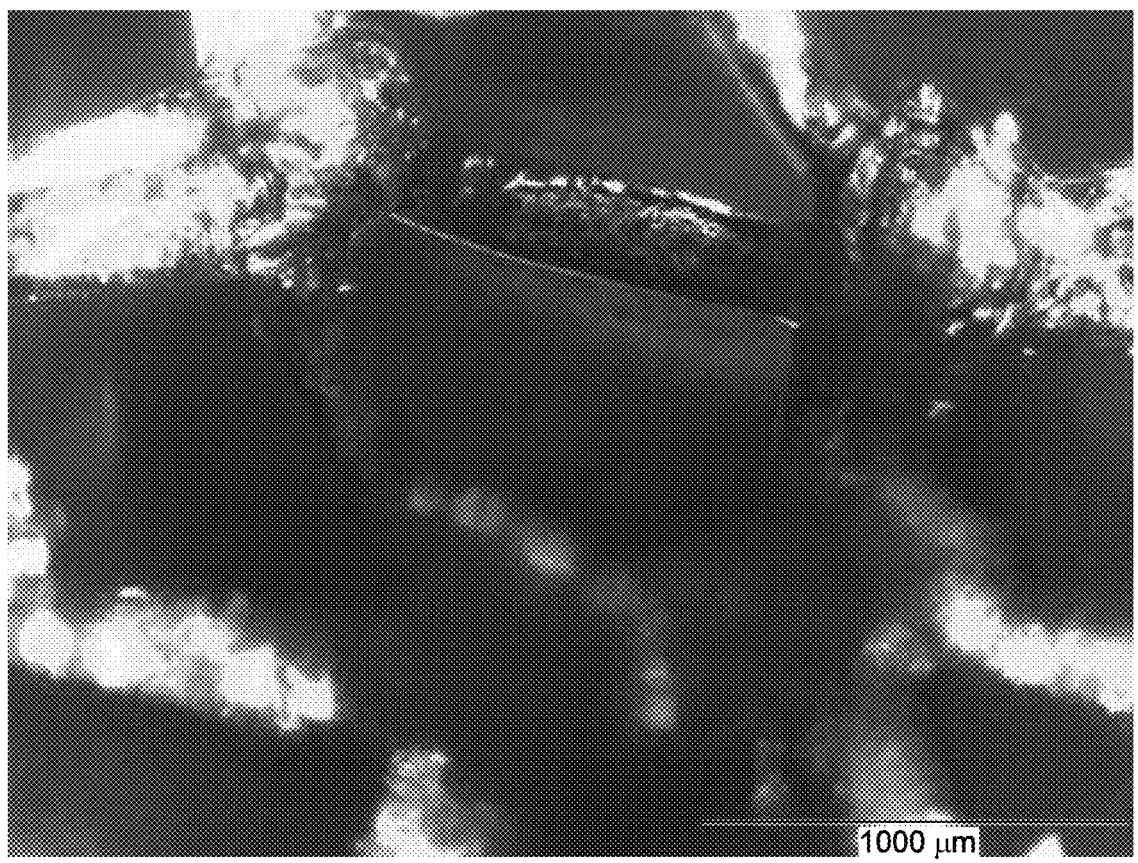
FIG. 10. Shows a representative image of polypropylene monofilament mesh coated with a thiol-ene polymer (40× OM). The thiolene polymer was loaded with minocycline hydrochloride and rifampin at a bulk mesh density of 200 µg/cm$^2$ for each drug.

Using the HPLC chromatographs from the Example 4 (Loading Drugs Post Curing), it was been demonstrated that subjected coatings to methanol rinses after curing results in much "cleaner" coating that contains less unreacted monomer, photoinitiator, or other byproducts (such as inhibitors or polymerization accelerators). The methanol rinse is inferred through the use of the 5 mL of 10 mg/mL drug loading solution. Further attempts may demonstrate that a methanol rinse can then be followed with a much smaller volume of drug loading solution, allowing for the minimization of drug solution waste and save on production costs. FIG. 9 shows the overlaid chromatographs demonstrating the removal of contaminants in the methanol rinse specimen (blue) as compared to the specimen that was not rinsed (red). The numerous large peaks shown in the red chromatograph are greatly reduced in the blue, demonstrating reduction of these components during the methanol rinse. Two black arrows have been added to show minocycline (left arrow) and rifampin (right arrow).

Example 6

Pentaerythritol Tetrakis(3-Mercaptopropionate) and Triallyl Isocyanurate Thiolene Coating with PTPO Initiator 1:1:8 weight ratio of monomer (67.22 wt % pentaerythritol tetrakis(3-mercaptopropionate), 32.73 wt % triallyl isocyanurate, and 0.05 wt % hydroquinone:tertbutyl cathetol (1:1 mixture by mole)):methanol:acetone containing minocycline hydrocholoride and rifampin at 50 mg/mL of each drug blend was made. PTPO (BASF P/N 56415733) was added at 0.1 wt %. Polymerization was induced using a halogen dental curing lamp through curing at a distance 2" from the light guide for 10 seconds on each side of the mesh. Six coats were applied to result in a theoretical loading of 0.2 mg/cm$^2$ of each drug. HPLC analysis of methanol extracts indicated 72% and 69% destruction of minocycline hydrochloride and rifampin, respectively. High degradation rates may be the result of the phosphine oxide initiator, which could destroy these drugs upon activation.

Example 7

Pentaerythritol Tetrakis(3-Mercaptopropionate) and Triallyl Isocyanurate Thiolene Coating, Proof-of-Principle for Irgacure® 2959 Initiator Functionality 1:1:8 weight ratio of monomer (67.22 wt % pentaerythritol tetrakis(3-mercaptopropionate), 32.73 wt % triallyl isocyanurate, and 0.05 wt % hydroquinone:tertbutyl cathetol (1:1 mixture by mole)):methanol:acetone containing minocycline hydrocholoride and rifampin at 50 mg/mL of each drug blend was made. Irgacure® 2959 (BASF P/N 55047962) was added at 0.1 wt %. Polymerization was induced using low output UV-C fluorescent lamp exposure for three minutes. Coatings cured based on touching with gloves and not seeing any monomer come off. No quantification of drugs performed. This formulation was pursued to demonstrate the ability to use the Irgacure® 2959 which is known to result in less drug degradation.

Example 8

Proof-of-Principle for Simple a Pentaerythritol Tetrakis(3-Mercaptopropionate) and Triallyl Isocyanurate Thiolene Coating System with High Levels of Minocycline Hydrochloride and Rifampin Incorporation 0.1 wt % Irgacure 2959 (BASF P/N 55047962) was added to 90:9:0.5:0.5 weight ratio methanol:monomer (67.22 wt % pentaerythritol tetrakis(3-mercaptopropionate), 32.73 wt % triallyl isocyanurate, and 0.05 wt % hydroquinone:tertbutyl cathetol (1:1 mixture by mole)):minocycline hydrochloride: rifampin. Curing was conducted under the UV-C lamps for three minutes. After the application of five coat, dry, and cure processes a drug density of 138 µg/cm$^2$ of the bulk mesh was obtained. Coatings cured based on touching with gloves and not seeing any monomer come off. No quantification of drugs performed. The formulation was pursed to demonstrate the ability to use a pure methanol solvent system in order to maximize drug solubility within the coating solution.

Example 9

Specimen Using a Pentaerythritol Tetrakis(3-Mercaptopropionate) and Triallyl Isocyanurate Thiolene Coating Formula Procedure:

Mesh was cut into three pieces, each approximate 4 cm$^2$. Each piece was weighed and it was made sure each piece was 50 mg as the actual area was, ca, 50.0 mg/(10.7 mg/cm$^2$)=4.7 cm$^2$. Thiolene formula (60 mg) (thiolene formula contains 67.22 wt % Pentaerythritol tetrakis(3-mercaptopropionate), 32.73 wt % Triallyl Isocyanurate, and 0.05 wt % Hydroquinone:tertbutyl cathetol (1:1 mixture by moles), density is, ca, 1.2 g/mL) was dissolved in acetone aiming for the concentration of 100 mg/mL. PTPO (4.5 mg) was dissolved in acetone aiming for the concentration of 10 mg/mL. 5 µL of the PTPO solution (contains 50 ug PTPO) and 100 µL of thiolene formula solution (contains 10 mg of thiolene formula) were mixed in a 1.5 mL centrifuge tube, so that the PTPO to thiolene monomer weight ratio was 0.5%. Took preweighed 157 µg of minocycline and 157 µg of rifampin, so the drug loading was about 0.04 mg/cm$^2$ for each drug. Made three specimens as shown Table 1. The solutions were transferred onto PP mesh using an automatic pipette while the meshes were held by a plastic clamp. Specimen 1 and 2 were subjected to curing while specimen 3 was chosen as uncured reference. The thiolene formula loading was set to 2.5 mg/cm$^2$ in this experiment.

TABLE 1

Formulations of the three specimens for Example 9

| Specimen 1 | Specimen 2 | Specimen 3 |
|---|---|---|
| 10 mg thiolene, 50 ug PTPO, 50 mg PP mesh | 10 mg thiolene, 50 ug PTPO, 50 mg PP mesh, 157 µg of minocycline and 157 µg of rifampin | 10 mg thiolene, 157 µg of minocycline and 157 µg of rifampin, 50 mg PP mesh |

The three specimens were dried using a gentle air blower; curing the specimens 1 and 2 with Norland Light Gun for one minute each side. Specimen 3 was left uncured as reference. The cured and uncured specimens were allowed to stand out under ambient conditions overnight and then soaked in 1 ml. MeOH overnight at 4° C. in the refrigerator. The order of procedure is: day 1: cure and stand out; day 2: soak in methanol; day 3, HPLC analysis.

The MeOH extract was subjected to reverse phase HPLC analysis. HPLC runs of each specimen extract from methanol were performed under the conditions below:

Channel A: 35 mM sodium phosphate monobasic, 1 vol % triethylamine, final pH=7.5 with phosphoric acid
Channel B: acetonitrile
Column temperature=30° C.
Column type: 3×150 mm with 3.5 μm phenyl phase packing
Measurement: absorbance at 280 nm
Solvent flow rate: 1 mL/min
Solvent profile: 0-10 minutes 0-50 vol % Channel B; 10-20 minutes 50 vol % Channel B; 20-25 minutes 50-0 vol % Channel B.

The concentration of minocycline hydrochloride and rifampin in specimen 2 after curing were determined using direct proportions of peak area integration of specimen 3.
a. Minocycline hydrochloride concentrations were based on peak area values at retention times of approximately 7.1 minutes. Integration of peak area was used.
b. Rifampin concentrations were based on peak area values at retention times of approximately 9.5 minutes.
c. So the antibiotics remaining after curing were calculated as:

{(Peak integration of specimen 2)/(peak integration of specimen 3)}×100%

Extract from specimen 1 was not analyzed by HPLC due to the fact no drug was loaded on the specimen. The three specimens were dried and weighed to determine how much mass was gained. For specimen 1 and 2, the mass gained was attributed to the polymer coated on PP mesh. For specimen 3, no mass was gained after methanol extraction. So the percentage of monomers reacted can be calculated as:

% of monomers reacted={(mass gain)/(total loading mass of 10 mg thiolene formula)}×100%

Figure 11:
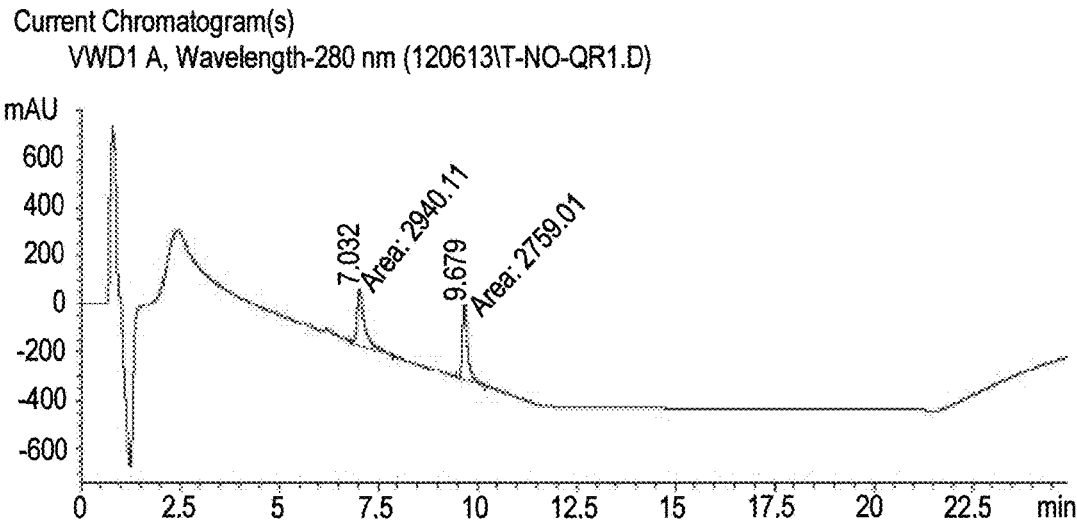
FIG. 11. Shows the HPLC chromatograms of the methanol extract solutions from thiolene coating of Example 9. The top chromatogram corresponds to specimen 3 and the bottom chromatogram corresponds to the cured specimen 2 with drug loading.
Figure 11:
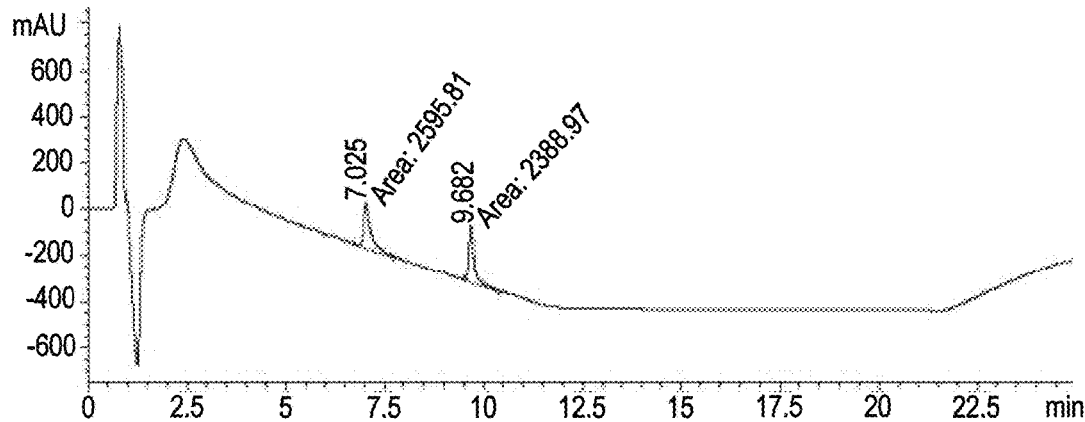

Results:
Antibiotics Retained after Curing
FIG. 11 shows the HPLC analysis of MeOH extract solution from thiolene coating. The top chromatogram corresponds to specimen 3 and the bottom chromatogram corresponds to the cured specimen 2 with drug loading. Minocycline and rifampin show up around 7.5 and 10 min, respectively, in HPLC analysis. Comparing the integration of the HPLC peaks of the two runs we could conclude how much antibiotics had remained after polymerization.

TABLE 2

Comparison of the cured and uncured drug retained after curing using area under the curve

| | Peak integration of specimen 3 | Peak integration of specimen 2 | Remaining after curing |
|---|---|---|---|
| Minocycline | 2940 | 2596 | 88% |
| Rifampin | 2759 | 2390 | 87% |

In this experiment, the PTPO was set to 0.5% weigh ratio of the monomers. It seemed 0.5% PTPO is an acceptable for thiolene coating due to the fact of that an acceptable amount of each antibiotic was retained after curing.

Percentage of Monomers Reacted
The drugs were retained after the curing process and confirmed by the HPLC analysis, however, the percentage of monomers reacted was not revealed merely based on the HPLC results. A simple method of determining the percentage of monomers reacted was using loss-mass method. In such method, the specimen was weighed before curing and after curing. The mass gain was associated with the polymer attached on the specimens. The claim here was based on the assumption that the MeOH washing would wash away all the free monomers and also the crosslink polymer did not dissolve in MeOH. Table 3 shows the percentage of monomers reacted for two different specimens as using the following calculation method. The total loading mass was 10 mg. PTPO and antibiotics were not counted simply because of too little amount. All specimens were weighed 3 times and an average value was presented.

% of monomers reacted={(mass gain)/(total loading mass)}×100%

TABLE 3

Comparison the mass difference after curing the specimens

| | Before loading chemicals | After loading and cured | Mass gain | % of monomers reacted |
|---|---|---|---|---|
| Specimen 1 (w/o drug) | 50.0 mg | 59.1 mg | 9.1 mg | 91% |
| Specimen 2 (w/drug) | 50.0 mg | 60.0 mg | 10.0 mg | 100% |

Therefore, we can conclude thiolene formula was suitable to coat polypropylene using PTPO UV curing method in the presence of antibiotics. The antibiotics survived well after the curing. Although the amount of drug retained is higher in the methods of Example 6, it must be considered that this experiment was carried out under different loadings for the specimens. The Following Table 4 is the summary of the difference between this experiment and the experiments using the protocol of example 6.

TABLE 4

Comparison of the methods and results of Example 6 and Example 9

| | Thiolene loading | Drug loading | Photoinitiator loading | Coating times | Drug retention |
|---|---|---|---|---|---|
| Example 6 | 5 mg/cm$^2$ | 0.2 mg/cm$^2$ | 1 wt % to thiolene | 5 | About 40% |
| Example 9 | 2.1 mg/cm$^2$ | 0.034 mg/cm$^2$ | 0.5 wt % to thiolene | 1 | About 85% |

Example 10

Specimen Using PEG DM Methacrylate Coating Formula

Procedure:
Three pieces, each approximate 4 cm$^2$, of polypropylene (PP) mesh (density d=107 g/m$^2$) were cut and weighed to make sure that each piece has same weight. The weight was 42.7 mg for each piece as the actual area was, ca, 42.7 mg/(10.7 mg/cm$^2$)=4 cm$^2$. Polyethylene glycol dimethacrylate (PEG DM) (60 mg) was weighed and dissolve the in acetone making the concentration as 100 mg/mL. PTPO (4.5 mg) was weighed and dissolve in acetone making the concentration as 10 mg/mL. 5 µL of PTPO solution (containing 50 ug PTPO) in step and 100 µL of PEG DM solution (containing 10 mg of PEG DM formula, described above) were mixed in a 1.5 mL centrifuge tube so that the PTPO to PEG DM weight ratio was 0.5%. Took preweighed 157 µg of minocycline and 157 µg of rifampin, so that the drug loading was about 0.04 mg/cm$^2$ in this experiment for each drug. Three specimens as shown in the Table 5 were prepared. The solutions were transferred onto PP mesh using an automatic pipette while the meshes were held by a plastic clamp. Specimen 4 and 5 were subjected to curing while specimen 6 was chosen as a reference. The thiolene formula loading was 2.5 mg/cm$^2$ in this experiment.

TABLE 5

Formulations for the specimens of Example 10

| Specimen 4 | Specimen 5 | Specimen 6 |
|---|---|---|
| 10 mg PEG DM, 50 ug PTPO, 50 mg PP mesh | 10 mg PEG DM, 50 ug PTPO, 50 mg PP mesh, 157 µg of minocycline and 157 µg of rifampin | 10 mg PEG DM, 157 µg of minocycline and 157 µg of rifampin, 50 mg PP mesh |

The three specimens were dried using a gentle air blower; curing the specimens 4 and 5 with Norland Light Gun for one minute each side. Specimen 6 was left uncured as reference. The cured and uncured specimens were allowed to stand out under ambient conditions overnight and then soaked in 1 mL MeOH overnight at 4° C. The order of procedure was:
day 1: cure and stand out; day 2: soak in methanol; day 3, HPLC analysis The MeOH extract from each specimen was subjected to HPLC analysis under the following conditions:
 a. Channel A: 35 mM sodium phosphate, 1 vol % triethylamine, pH=7.5 with phosphoric acid
 b. Channel B: acetonitrile
 c. Column temperature=30° C.
 d. Solvent profile: 0-10 minutes 0-50 vol % Channel B; 10-20 minutes 50 vol % Channel B; 50-0 vol % Channel B 20-50 min Using direct proportions of peak integration of specimen 6, the concentration of minocycline hydrochloride and rifampin in specimen 5 after curing was determined. Minocycline hydrochloride concentrations were based on peak area values at retention times of approximately 7.1 minutes. Integration of peak area was used. Rifampin concentrations were to be based on peak area values at retention times of approximately 9.5 minutes. The antibiotics remaining after curing were calculated as:

{(Peak integration of specimen 5)/(peak integration of specimen 6)}×100%

Extract from specimen 4 was not analyzed by HPLC due to the fact no drug was loaded on the specimen. The three specimens were dried and weighed to see how much mass was gained. For specimen 4 and 5, the mass gained was attributed to the polymer coated on PP mesh. For specimen 6, no mass was gained after methanol extraction. So the percentage of monomers reacted can be calculated as:

% of monomers reacted={(mass gain)/(total loading mass of 10 mg PEG DM formula)}×100%

Results:
Antibiotics Retained after Curing

Figure 12:
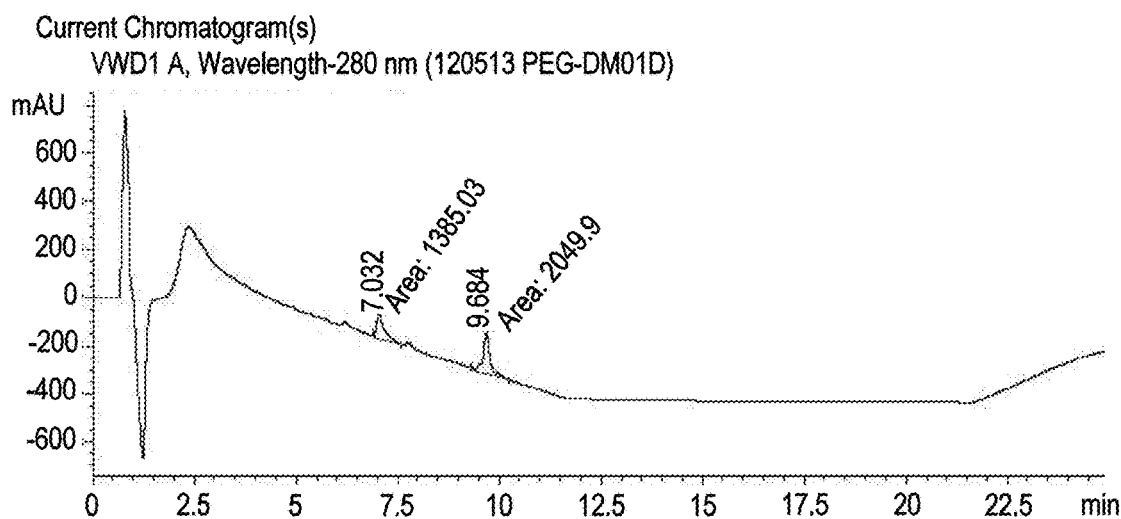
FIG. 12. Shows the HPLC chromatograms of the methanol extract solution from PEG DM coating of Example 10. The top chromatogram corresponds to uncured specimen 6 and the bottom chromatogram corresponds to the cured specimen 5 with drug loading.
Figure 12:
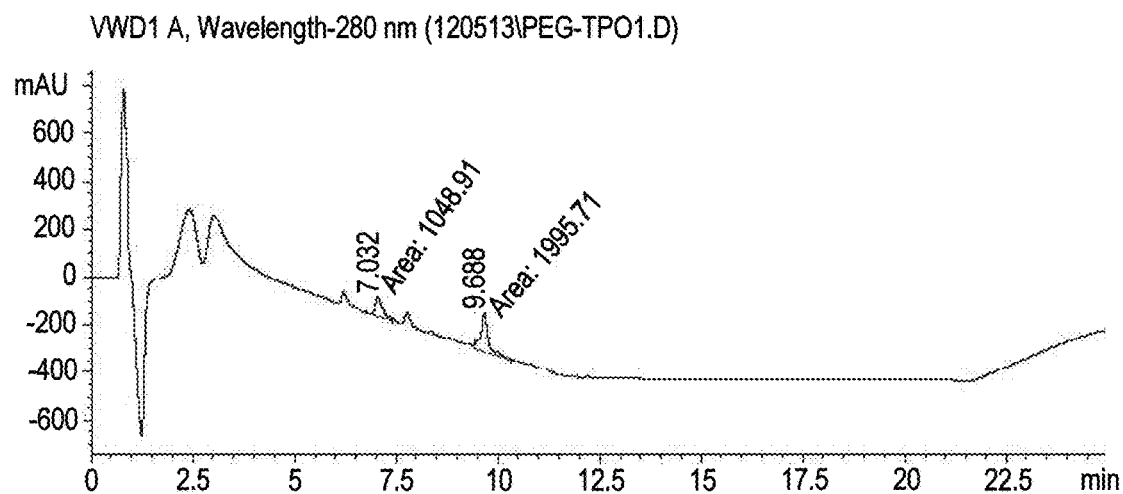

FIG. 12 shows the HPLC analysis of MeOH extract solution from PEG DM coating. The top chromatogram is the uncured specimen 6 and the bottom chromatogram is the cured specimen 5 with drug loading. Comparing the integration of the HPLC peaks of the two runs we could conclude how much antibiotics had remained after polymerization.

TABLE 6

Comparison of the cured and uncured drug retained in PEG DM coating method

| | Peak integration of specimen 6 | Peak integration of specimen 5 | Remaining after curing |
|---|---|---|---|
| Minocycline | 1386 | 1049 | 76% |
| Rifampin | 2049 | 1997 | 97% |

% of monomers reacted={(mass gain)/(total loading mass as 10 mg PEG DM)}×100%

TABLE 7

Comparison the mass difference after curing the specimens with PEG DM

| | Before loading chemicals | After loading and cured | Mass gain | % of monomers reacted |
|---|---|---|---|---|
| Specimen 4 (w/o drug) | 42.7 mg | 49.1 mg | 6.4 mg | 64% |
| Specimen 5 (w/drug) | 42.7 mg | 44.1 mg | 1.4 mg | 14% |

Comparing the thiolene coating and PEG DM coating, it can be see the thiolene coating works better in terms of polymerization conversion and drug retention. The PEG DM coating works fine without the antibiotics. However, the conversion of monomer to polymer decreased dramatically when the antibiotics were loaded. It is possible that the radicals are stolen by the drugs for PEG DM polymerization process.

Example 11

Specimen Using a Pentaerythritol Tetrakis(3-Mercaptopropionate) and Triallyl Isocyanurate Thiolene Coating Formula with 0.4 mg/cm$^2$ Drug Loading Procedure:
Three 35.3 mg, 3.24 cm$^2$ pieces of polypropylene mesh were cut. About 80 mg thiolene formula (67.22 wt % pentaerythritol tetrakis(3-mercaptopropionate), 32.73 wt % triallyl isocyanurate, and 0.05 wt % hydroquinone:tertbutyl cathetol (1:1 mixture by moles), density is, ca, 1.2 g/mL) was weighed and dissolve the formula in acetone aiming for the concentration of 200 mg/mL. Weighed about 2 mg PTPO and dissolved it in acetone aiming for the concentration of 10 mg/mL. Took 8.1 µL of solution of PTPO (which contained 81 ug PTPO) and 81 µL of the thiolene solution (which contained 16.2 mg of thiolene formula) and mixed them in a 1.5 mL centrifuge tube, so that the PTPO to monomer weight ratio was 0.005. The thiolene formula to PP mesh ratio was 5 mg/cm$^2$. Used preweighed 1.3 mg of minocycline and 1.3 mg of rifampin to create formulations as shown in Table 8. Drugs were dissolved in methanol and drug/methanol solutions were mixed with monomer/acetone solutions such that solvent ratios were at 2:1 acetone:methanol for drug containing specimens (Table 8). Those specimens not containing drug used pure acetone solvents in the coating formulation. Drug loading was about 0.4 mg/cm$^2$ in this experiment for each drug. The solutions were transferred onto polypropylene mesh using micropipette while the meshes were held by a plastic clamp. Specimen 7 and 8 were subjected to curing while specimen 9 was made as reference for HPLC analysis.

TABLE 8

Specimens generated in Example 11

| Specimen 7 | Specimen 8 | Specimen 9 |
|---|---|---|
| 16.2 mg thiolene formula, 81 ug PTPO, 35.3 mg PP mesh | 16.2 mg thiolene formula, 81 ug PTPO, 35.3 mg PP mesh, 1.3 mg of minocycline and 1.3 mg of rifampin | 1.3 mg of minocycline and 1.3 mg of rifampin |

The three specimens were dried using a gentle air blower. Specimens 7 and 8 were cured with Norland Light Gun for one minute each side. Specimen 9 was used as reference. The cured specimens were allowed to stand out under ambient conditions overnight and then the specimens were soaked in 1 mL methanol overnight at 4° C. in the refrigerator. The order of procedure was: day 1, cure and stand out, day 2, soak in methanol and day 3, HPLC analysis.

The MeOH extract of specimens 8 to HPLC analysis under the following conditions.
Channel A: 35 mM sodium phosphate, 1 vol % triethylamine, pH=7.5 with phosphoric acid
Channel B: acetonitrile
Column temperature=30° C.
Solvent profile: 0-10 minutes 0-50 vol % Channel B; 10-20 minutes 50 vol % Channel B; 50-0 vol % Channel B 20-25 min.

The concentration of minocycline hydrochloride and rifampin in specimen 8 was determined using direct proportions of peak area integrations and taking of specimen 8 as 100% drug control. Minocycline hydrochloride concentrations were based on peak area values at retention times of approximately 7.1 minutes. Integration of peak area was used. Rifampin concentrations were based on peak area values at retention times of approximately 9.5 minutes. The antibiotics remaining after curing was calculated as:

{(Peak integration of specimen 8)/(peak integration of specimen 9)}×100%

The two cured specimens after were dried and weigh to see how much mass was gained. For specimen 7 and 8, the mass gained was attributed to the polymer coated on the polypropylene mesh. So the percentage of monomers reacted could be calculated as:

% of monomers polymerized={(mass gain)/(total loading mass of 16.2 mg thiolene formula)}×100%

Figure 13:
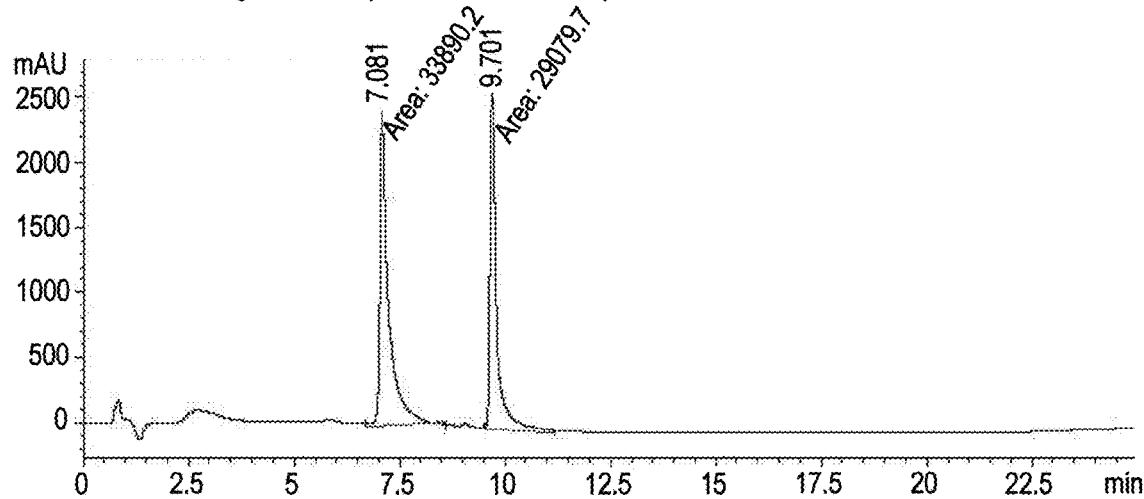
FIG. 13. Shows the HPLC chromatograms of the methanol extract solution from thiolene coating of Example 11. The top chromatogram corresponds to uncured specimen 9 and the bottom chromatogram corresponds to the cured specimen 8 with drug loading FIG. 14. Shows the HPLC chromatograms of the methanol extract solution from PEG DM coating of Example 12. The top chromatogram corresponds to uncured specimen 9 and the bottom chromatogram corresponds to the cured specimen 11 with drug loading FIG. 15. Shows the HPLC chromatograms of methanol extract solution from PEG DM coating with drug loading of Example 13, the reference was the same specimen 9 shown in Examples 11 and 12.
Figure 13:
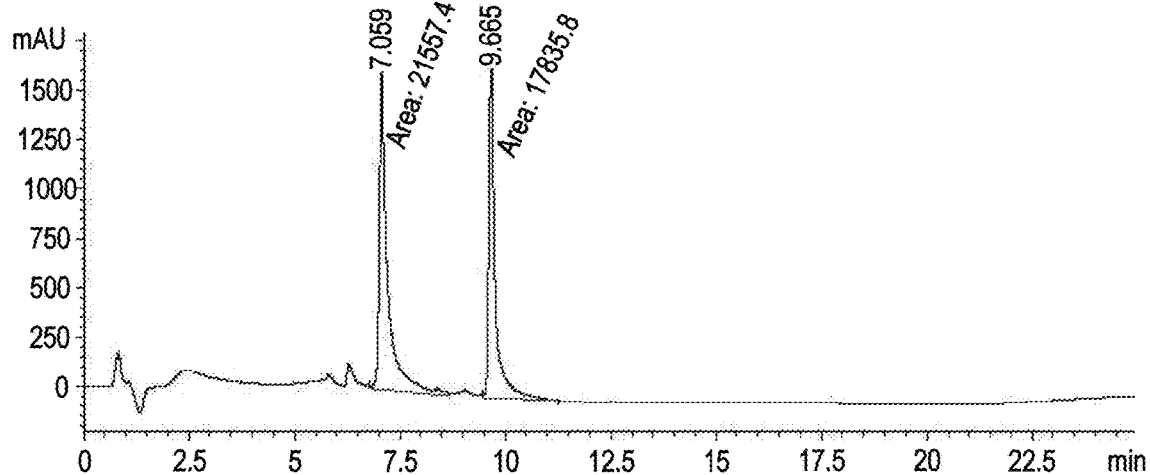

Results:
Antibiotics Retained after Curing
FIG. 13 shows the HPLC analysis of MeOH extract solution from thiolene coating. The top is specimen 9 and the bottom is the cured specimen 8 with drug loading. How much antibiotics remained after polymerization was calculated by comparing the integration of the chromatograph peaks of interest the two HPLC chromatograms.

TABLE 9

HPLC peak integration of drugs using peak area for the specimens of Example 11

| | Peak integration of specimen 8 | Peak integration of specimen 9 | Remaining after curing |
|---|---|---|---|
| Minocycline | 21,554 | 33,890 | 64% |
| Rifampin | 17,838 | 29,097 | 61% |

Percentage of Monomers Reacted

% of monomers polymerized={(mass gain)/(total loading mass)}×100%

TABLE 10

Weight percentage of monomer polymerized data

| | Before loading chemicals | After loading, curing, and washing | Mass gain | wt % of monomers polymerized |
|---|---|---|---|---|
| Specimen 7 (w/o drug) | 35.3 mg | 43.7 mg | 8.4 mg | 52% |
| Specimen 8 (w/drug) | 35.3 mg | 50.0 mg | 14.7 mg | 90% |

Example 12

Specimen Using a Pentaerythritol Tetrakis(3-Mercaptopropionate) and PEG DM Thiolene Coating Formula with 0.4 mg/Cm$^2$ Drug Loading Procedure All procedures were same as Example 11 except that the thiolene formula was replaced by the following formula (10 g of pentaerythritol tetrakis(3-mercaptopropionate) (from Sigma Aldrich, P #381462, lot #80896TMV) and 21.4 g of polyethylene glycol dimethacrylate (from Sigma Aldrich, P #409510, lot # MKBP0253V) (EXP12-formula). The curing time was set to 10 mins. The two specimens used in curing are shown in the following Table 11. Specimen 9 as discussed in Example 11 was used as a standard.

TABLE 11

Specimens generated using PEG DM coating formula

| Specimen 10 | Specimen 11 |
|---|---|
| 16.2 mg EXP12-formula coating formula, 81 ug PTPO, 35.3 mg PP mesh | 16.2 mg EXP12-formula coating formula, 81 ug PTPO, 35.3 mg PP mesh, 1.3 mg of minocycline and 1.3 mg of rifampin |

Figure 14:
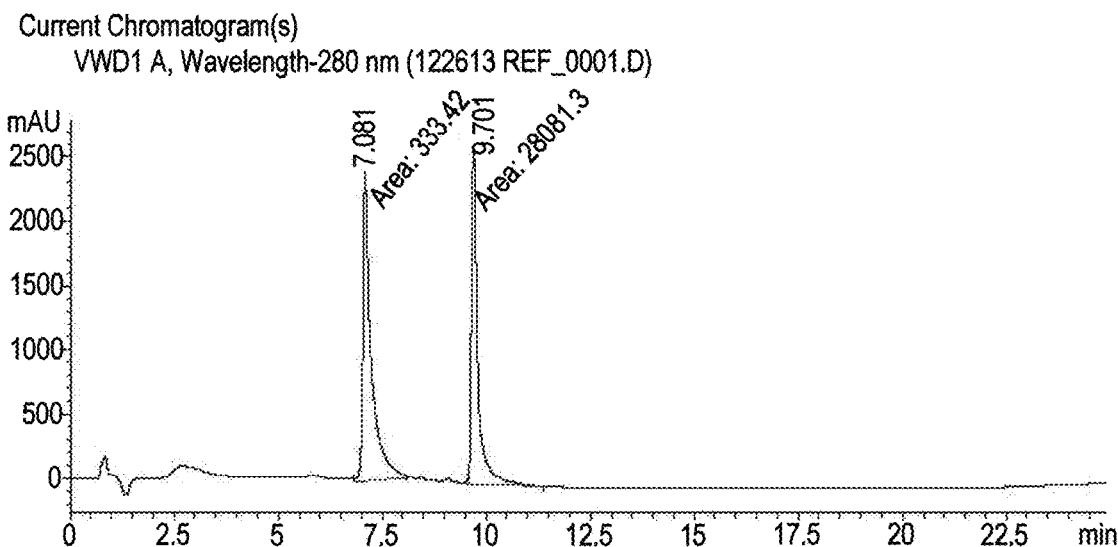
Figure 14:
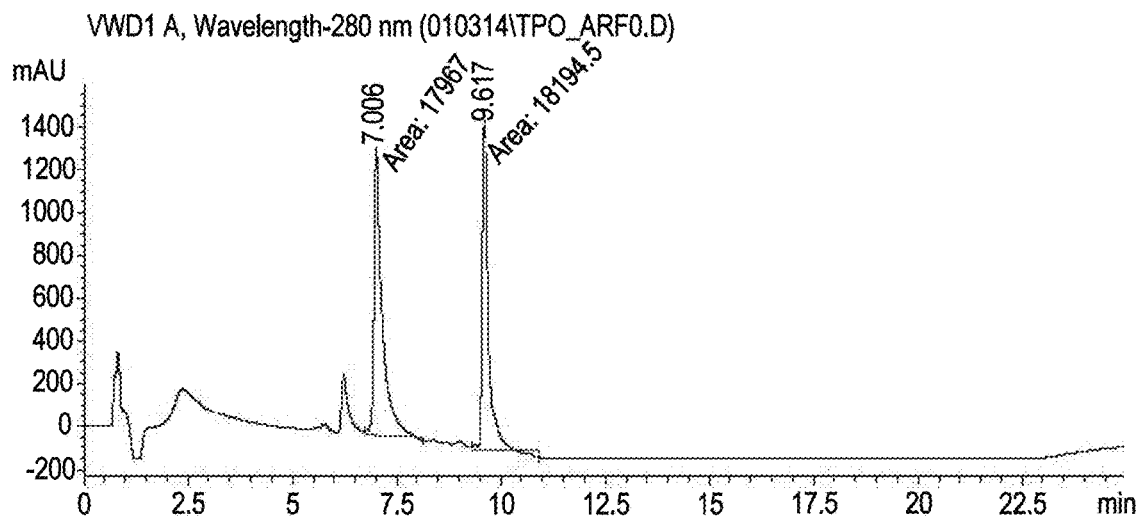

Results:
Antibiotics Retained after Curing
FIG. 14 shows the HPLC analysis of MeOH extract solution from EXP12-formula. The top is specimen 9 and the bottom is the cured specimen 11 with drug loading.

TABLE 12

Cured and uncured drug retaining data by HPLC peak integration method based on 100% drug standard of sample 3.

|  | Peak integration of specimen 11 | Peak integration of specimen 9 | Remaining after curing |
|---|---|---|---|
| Minocycline | 17,967 | 33,342 | 54% |
| Rifampin | 16,195 | 28,081 | 58% |

% of monomers polymerized={(mass gain)/(total loading mass as 16.2 mg PEG DM coating formula)}×100%

TABLE 13

Weight percentage of monomer polymerized data.

|  | Before loading chemicals | After loading, curing, and washing | Mass gain | Wt % of monomers polymerized |
|---|---|---|---|---|
| Specimen 10 (w/o drug) | 35.3 mg | 40.8 mg | 5.5 mg | 34% |
| Specimen 11 (w/drug) | 35.3 mg | 49.4 mg | 14.1 mg | 87% |

Example 13

Specimen Using a Pentaerythritol Tetrakis(3-Mercaptopropionate) and PEG DM Thiolene Coating Formula and Irgacure 2959 as Photoinitiator All procedures are same as Example 12 except the PTPO is replaced by Irgacure 2959. The curing time was set to 10 mins. The UV source was Ariste UV-C chamber. So the two specimens used in curing are shown in following table. Once again, the specimen 3 was used as reference for calculating how much antibiotics was remained after curing.

TABLE 13

Specimens created using Irgacure 2959 as photoinitiator

| Specimen 12 | Specimen 13 |
|---|---|
| 16.2 mg EXP12-formula coating formula, 81 ug Irgacure 2959, 35.3 mg PP mesh | 16.2 mg EXP12-formula coating formula, 81 ug Irgacure 2959, 35.3 mg PP mesh, 1.3 mg of minocycline and 1.3 mg of rifampin |

Figure 15:
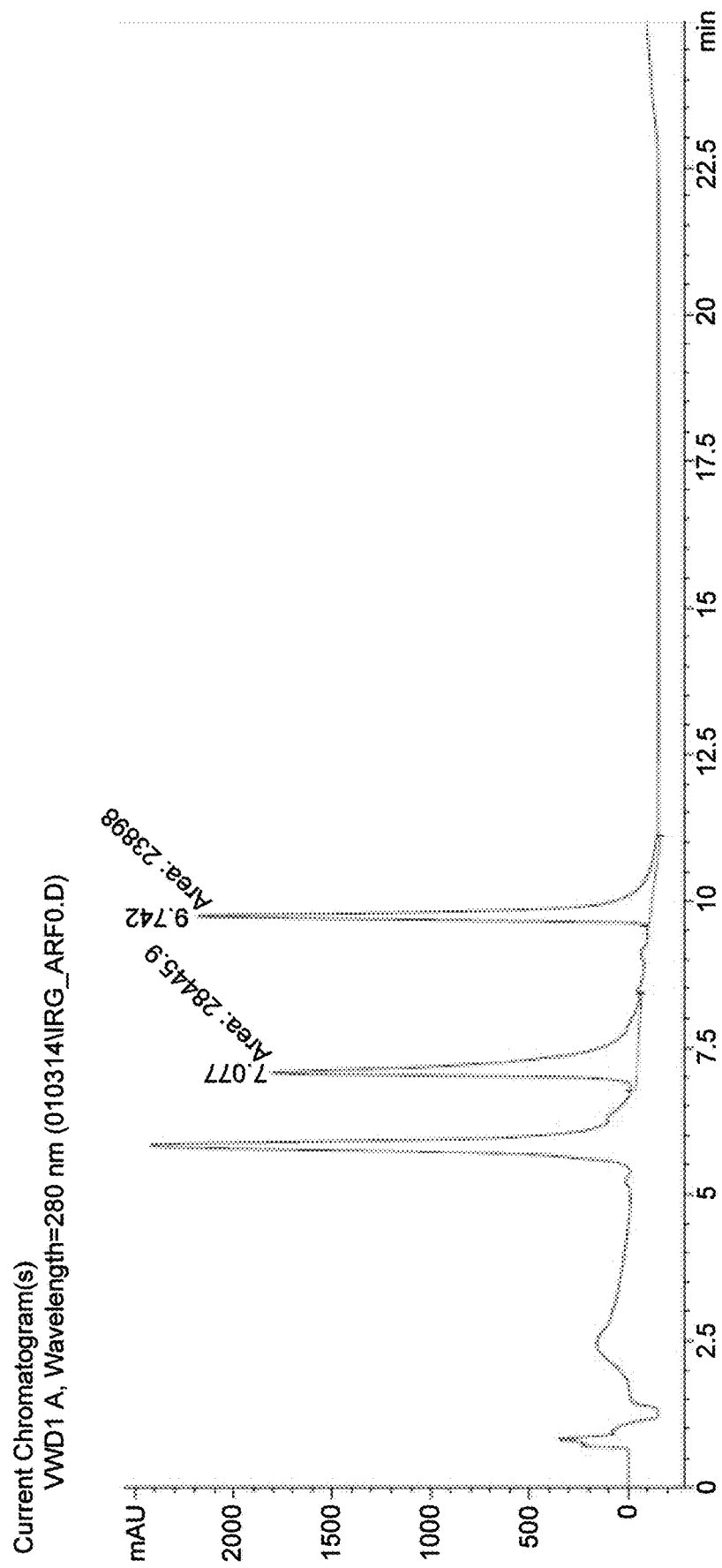

Results:
Antibiotics Retained after Curing
FIG. 15 shows the HPLC analysis of MeOH extract solution from EXP12-formula coating formula cured specimen 13 with drug loading and its reference was the same specimen 9 shown in Examples 11 and 12.

TABLE 14

Cured drug retaining data by HPLC peak integration method

|  | Peak integration of specimen 12 | Peak integration of specimen 9 | Remaining after curing |
|---|---|---|---|
| Minocycline | 28,445 | 33,342 | 85% |
| Rifampin | 23,898 | 28,081 | 85% |

% of monomers polymerized={(mass gain)/(total loading mass as 16.2 mg PEG DM coating formula)}×100%

TABLE 15

Weight percentage of monomer polymerized for specimens 12 and 13.

|  | Before loading chemicals | After loading, curing, and washing | Mass gain | % of monomers reacted |
|---|---|---|---|---|
| Specimen 12 (w/o drug) | 35.3 mg | 51.2 mg | 15.9 mg | 98% |
| Specimen 13 (w/drug) | 35.3 mg | 35.3 mg | 0 mg | 0% |

The zero percent monomer conversion indicated the Irgacure 2959 was not able to initiate the polymerization in presence of the drugs, while PTPO was able to initiate the polymerization and about 34% monomer was reacted as shown in Example 12.

Example 14

Post Curing Loading of Drugs on Methacrylate Polymeric Coatings

Certain drugs, especially those which contain amine groups and unsaturated bonds, are susceptible to degradation in the presence of the free radical chain growth vinyl polymerization and activated photoinitiators due to the phenomenon of a chain transfer reaction known as hydrogen abstraction between carbon-hydrogen bonds and the living polymer's and activated photoinitiators radical end and reduction of unsaturated carbon-carbon bonds by the living polymer's and activated photoinitiator's radical centers. Polymerization may be terminated and the drug molecule may be degraded. This observation is not a surprise as amine groups and their neighboring carbons can participate in this chain termination reaction. We have developed a process to produce equivalent drug loading quantities in DualMesh Biomaterial through use of post cure loading as compared to that that which is achieved when the polymerization of the coating occurs with the drugs present. Although similar loading quantities are achieved, it is desirable to load post cure so that drug degradation products are not included within the resulting coating's polymer network.

A 1:1:1:1 acetone:ethanol:BPDM solution:NTG-GMA solution in 1:1:1:1 volume ratio was used to coat DualMesh Biomaterial with drugs both present during the polymerization process and loaded into the polymer network after curing had been performed. Circular 0.785 cm$^2$ samples of 0.005" silicone-backed ePTFE were coated. In the version were drugs were included in the casting solution, both minocycline hydrochloride and rifampin were incorporated at levels such if no degradation were to have occurred each drug would have been loaded at a bulk surface area density of 400 μg/cm$^2$. The post-cure loaded version was created by coating the 0.005" silicone-backed ePTFE with the same amount of polymer coating, and then placing the silicone-backed ePTFE on an elevated piece of silicone, above a pool of methanol within a sealable vessel whose gaseous contents was largely methanol vapor. 60 μl of a methanol/drug solution (1.31 mg/ml of each minocycline hydrochloride and rifampin) was then applied flooded within polymer coated ePTFE microstructure. The vessel was capped and left undisturbed for 24 hours. After 24 hours the specimen was retrieved and methanol allowed to evaporate in air. The coated specimen had then been loaded with each drug at 0.1 mg/cm$^2$.

What is claimed is:

1. A method of coating a medical device surface, the method comprising:
providing the medical device, said medical device having a microstructure;
exposing a surface of the medical device to a coating formulation comprising:
0.005-80 wt % of a thiol monomer comprising a polythiol;
0.005-80 wt % of an unsaturated monomer, wherein the unsaturated monomer is triallyl isocyanurate or polyethylene glycol dimethacrylate; and
a therapeutic agent; and
inducing polymerization of the coating formulation to obtain a coated device surface that elutes the therapeutic agent.

2. The method of claim 1, wherein the therapeutic agent is selected from rifampicin, minocycline, minocycline hydrochloride, minocycline hyclate, or any combination thereof.

3. The method of claim 1, wherein the polythiol comprises pentaerythritol tetrakis(3-mercaptopropionate).

4. The method of claim 1, wherein the thiol monomer is selected from: glyceryl 1,3-dithioglycolate, glycol dimercaptoacetate, ethoxylated-trimethylolpropan tri(3-mercaptopropionate), trimethylolpropane tris (3-mercaptopropionate), 4-mercaptomethyl-3,6-dithia-1,8-octanedithiol, pentaerythritol tetrakis (3-mercaptoacetate), trimethylolpropane tris (3-mercaptoacetate), 4-t-butyl-1,2-benzenedithiol, bis(2-mercaptoethyl)sulfide, 4,4'-thiodibenzenethiol, benzenedithiol, glycol dimercaptopropionate ethylene bis(3-mercaptopropionate), polythylene glycol dimercaptoacetate, polythylene glycol di(3-mercaptoacetate), (tetrahydrothiophene-2,5-diyl)dimethanethiol, bis(2-mercaptoethyl)sulfide, tris-(3-mercaptopropyl)isocyanurate, 1,2,3-trimercaptopropane, 2,2-bis(mercaptomethyl)-1,3-propanedithiol, 2,5-dimercaptomethyl-4-dithiane, 1,2,4-trimercaptomethyl benzene, 4,8-bis(mercaptomethyl)-3,6,9-trithia-1,11-undecanedithiol, 2-mercaptomethyl-2-methyl-1,3-propanedithiol, 1,8-dimercapto-3,6-dioxaoctane; 2,2',2"-(2,4,6-trioxo-1,3,5-triazinane-1,3,5-triyl)tris(ethane-2,1-diyl) tris(3-mercaptopropanoate), or any combination thereof.

5. The method of claim 1, wherein the coating formulation further comprises a radical scavenger selected from hydroquinone, tertbutyl cathetol, or a combination thereof.

6. The method of claim 1, wherein the polythiol is pentaerythritol tetrakis (3-mercaptoacetate).

7. The method of claim 1, wherein the polythiol is pentaerythritol tetrakis (3-mercaptoacetate) and the unsaturated monomer is triallyl isocyanurate.

8. The method of claim 1, wherein the polythiol is pentaerythritol tetrakis (3-mercaptoacetate) and the unsaturated monomer is polyethylene glycol dimethacrylate.

9. The method of claim 1, further comprising eluting the therapeutic agent from the coated device surface.

10. A method of coating a medical device surface, the method comprising:
providing the medical device, said medical device having a microstructure;
exposing a surface of the medical device to a coating formulation comprising:
0.005-80 wt % of pentaerythritol tetrakis (3-mercaptoacetate); and
0.005-80 wt % of an unsaturated monomer, wherein the unsaturated monomer is triallyl isocyanurate or polyethylene glycol dimethacrylate; and
inducing polymerization of the coating formulation to obtain a coated medical device surface that elutes a therapeutic agent.

11. The method of claim 10, wherein the coating formulation further comprises the therapeutic agent.

12. The method of claim 10, further comprising physically assisting the coating formulation to enter the microstructure of the medical device by applying an external force prior to inducing polymerization of the coating formulation.

13. The method of claim 12, wherein the external force is a negative pressure.

14. The method of claim 12, wherein the external force is a positive pressure.

15. The method of claim 10, further comprising exposing the medical device to a solution comprising the therapeutic agent.

16. The method of claim 15, wherein the exposing of the medical device to the solution comprising the therapeutic agent is performed at a reduced temperature from −50° C. to 0° C.

* * * * *